(12) United States Patent
Falchuk

(10) Patent No.: US 6,902,881 B2
(45) Date of Patent: Jun. 7, 2005

(54) COMPOUNDS AND METHODS FOR REGULATING CELL DIFFERENTIATION

(75) Inventor: Kenneth H. Falchuk, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 203 days.

(21) Appl. No.: 10/008,356

(22) Filed: Nov. 13, 2001

(65) Prior Publication Data

US 2002/0169201 A1 Nov. 14, 2002

Related U.S. Application Data

(63) Continuation-in-part of application No. 09/977,866, filed on Oct. 15, 2001.
(60) Provisional application No. 60/264,814, filed on Jan. 29, 2001, provisional application No. 60/262,233, filed on Jan. 17, 2001, provisional application No. 60/247,299, filed on Nov. 10, 2000, and provisional application No. 60/240,497, filed on Oct. 13, 2000.

(51) Int. Cl.$^7$ ............................ A01N 1/00; A01N 43/38; C12N 5/02; A61K 31/409
(52) U.S. Cl. ........................ 435/1.1; 435/325; 514/359; 514/422
(58) Field of Search .................. 435/1.1, 325; 514/359, 514/422

(56) References Cited

U.S. PATENT DOCUMENTS

| | | | |
|---|---|---|---|
| 5,229,500 A | 7/1993 | Barde et al. | 514/12 |
| 5,635,533 A | 6/1997 | Samid | 514/538 |
| 5,849,777 A | 12/1998 | Scallen et al. | 514/400 |
| 6,066,618 A | 5/2000 | Holick | 514/12 |
| 6,174,905 B1 | 1/2001 | Suzuki et al. | 514/346 |
| 6,242,471 B1 | 6/2001 | Yasuma et al. | 514/375 |

FOREIGN PATENT DOCUMENTS

| | | |
|---|---|---|
| JP | 3047166 | 2/1991 |
| JP | 6183969 | 7/1994 |
| WO | WO 93/09229 | 5/1993 |
| WO | WO 95/18856 | 7/1995 |
| WO | WO 96/17924 | 6/1996 |
| WO | WO 01/82932 | 11/2001 |
| WO | WO 01/96345 | 12/2001 |

OTHER PUBLICATIONS

Janes et al. "Role of hyperbilirubinemia . . . " J. Clin. Invest. 1995 95(6): 2581–6.*
Haga et al. "Intracellular accumulation . . . " Digest. Diseases Sci. 1996 41(7): 1468–74.*
Rhine et al. "Bilirubin toxicity . . . " J. Perinatol. 1999 19(3): 206–211.*
Nakajima et al. "Erythroid differentiation–inducing . . . " Biochem. Biophys. Res. Comm. 1994 198(2): 720–7.*
Notter et a. "Differential sensitivity . . . " Exp. Neurol. (Dec. 1986) 94(3): 670–82.*
Sima et al. "The suppressive effect . . . " Folia Microbiologica 1980 25(6) 483–90.*
Webster's II New Riverside Dictionary 1984, Houghton–Mifflin: Boston, pp. 762–990.*
Anderson et al., "The structural basis of lipid interactions in lipovitellin, a soluble lipoprotein," *Structure*, 6(7):895–909, 1998.
Bjeldanes et al., "Aromatic hydrocarbon responsiveness–receptor agonists generated from indole–3–carbinol in vitro and in vivo: comparisons with 2,3,7,8–tetrachlorodibenzo–p–dioxin," *Proc. Nat'l. Acad. Sci., USA*, 88:9543–9547, 1991.
Blauer and Wagniere, "Conformation of Bilirubin and Biliverdin in Their Complexes with Serum Albumin," *Am. Chem. Soc.*, 97(7):1949–1954, 1975.
Bligh and Dyer, "A Rapid Method of Total Lipid Extraction and Purification," *Canadian J. of Biochem. and Phys.*, 37:911–917, 1959.
Brand–Saberi et al., "The ventraliziing effect of the notochord on somite differentiation in chick embryos," *Anat. Embryol.*, 188:239–245, 1993.
Byrne, "The Evolution of Egg Yolk Proteins," *Prog. Biophys. Mol. Biol.*, 53:33–69, 1989.
Carr et al., "The Variable Transformation in Metastases from Testicular Germ Cell Tumors: The Need for Selective Biopsy," *J. Urol.*, 126:52–54, 1981.
Chen et al., "Human Breast Cancer Cells and Normal Mammary Epithelial Cells: . . . ," *Cancer Res.*, 57:4642–4651, 1997.
Collins et al., "Terminal Differentiation of Human Promyelocytic Leukemia Cells Induced by Dimethyl Sulfoxide and other Polar Compounds," *Proc. Natl. Acad. Sci. USA*, 75: 2458–2462, 1978.
Danilchik and Gerhart, "Differentiation of the Animal–Vegetal Axis in *Xenopus laevis* Oocytes . . . ," *Dev. Biol.*, 122:101–112, 1987.
Davidson, "How embryos work: a comparative view of diverse modes of cell fate specification," *Development*, 108:365–389, 1990.
Dexter DL, "NN–Dimethylformamide–induced Morphological Differentiation and Reduction of Tumorgenicity in Cultured Mouse Rhabdomyosarcoma Cells," *Cancer Res.* 37:3136–3140 (1977).
Dolphin et al., Studies on the Induction and Biosynthesis of Vitellogenin, an Oestrogen–Induced glycolipophosphoprotein, *Biochem. J.*, 124:751–758, 1971.

(Continued)

*Primary Examiner*—Jean C. Witz
*Assistant Examiner*—Susan Hanley
(74) *Attorney, Agent, or Firm*—Banner & Witcoff, Ltd.

(57) ABSTRACT

The present invention makes available methods and reagents for inhibiting cell growth or promoting cell differentiation comprising contacting the cell with a differeguline in a sufficient amount to inhibit cell proliferation or promote cell differentiation.

7 Claims, 18 Drawing Sheets

OTHER PUBLICATIONS

Donehower et al., "Nedd Deficient for p53 Are Developmentally Normal but Susceptible to Spontaneous Tumors," *Nature* 356: 215–221, 1992.

Donehower, "The p53–deficient Mouse: A model for basic and applied cancer studies," *Cancer Biol.* 7:269–278, 1997.

Dumont, "Oogenesis in *Xenopus laevis* . . . ," *J. Morphol.*, 136:153–179, 1972.

Ezquieta and Vallejo, "Lipovitellin Inhibition of Artemia Trypsin–Like Proteinase: . . . ," *Arch. Biochem. Biophys.*, 250(2):410–417, 1986.

Fagotto and Gumbiner, "β–catenin localization during Xenopus embryogenesis: . . . ," *Development*, 120:3667–3679, 1994.

Fainsod, Steinbeisser and Robertis, On the function of BMP-4 in patterning the marginal zone of the Xenopus embryo, *EMBO J.*, 13(21)5015–5025, 1994.

Heyman et al., "9–Cis Retinoic Acid Is a High Affinity Ligand for the Retinoid X Receptor." *Cell*, 397–406, 1992.

Huberman et al., "Induction of terminal differentiation in human promyelocytic leukemia cells by tumor promoting agents," *Proc. Natl. Acad. Sci, USA*, 76(3):1293–1297, 1971.

Ishizawa et al., "Induction of Heme Oxygenase in Rat Liver," *J. Biol. Chem.*, 258(7):4220–4225, 1983.

James et al., "The Role of Vitamin D Derivatives and Retinoids in the Differentiation of Human Leukaemia Cells," *Biochem. Pharmacol.*, 54:625–634, 1997.

Jellinck et al., Ah Receptor Binding Properties of Indole Carbinols and Induction of Hepatic Estradiol Hydroxylation, *Biochem. Pharmacol.*, 45(5):1129–1136, 1993.

Jessell et al., Diffusible Factors in Vertebrate Embryonic Induction, *Cell* 68:257–270, 1992.

Jones et al., "DVR–4 (Bone Morphogenetic Protein–4) as a posterior–ventralizing factor in Xenopus mesoderm induction," *Development*, 115:639–647, 1991.

King and Brown, "The Mechanism of Haem Catabolism," *J. Biochem.*, 174:103–109, 1978.

Kleman et al., "Regulation of Human Dioxin Receptor Function by Indolocarbazoles, Receptor Ligands of Dietary Origin," *J. Biol. Chem.*, 269(7):5137–5144, 1994.

La Fleur et al., "*Fundulus heteroclitus* Vitellogenin: . . . ," *J. Mol. Evol.*, 41:505–521, 1995.

Lagueux et al., "Ecdysteroids Are Bound to Vitellin Newly Laid Eggs of Locusta," *Mol. Cell. Endocrin.*, 24:325–338, 1981.

Landers and Bunce, "The Ah receptor and the mechanism of dioxin toxicity," *Biochem J.*, 276:273–287, 1991.

Lange et al., "Lipovitellin–Phosvitin Crystals with Orthorhombic Features: . . . ," *J. Ultrastruct. Res.*, 83:122–140, 1983.

Falchuk et al., "Zinc Uptake and Distribution in *Xenopus laevis* Oocytes and Embryos," *Biochemistry* 34:16524–16531, 1995.

Fearon et al., "Differentiation of Leukemia Cells to Polymorphonuclear Leukocytes in Patients with Acute Nonlymphocytic Leukemia," *N. Eng. J. Med.* 315: 15–24, 1986.

Fibach et al., "Effect of Hexamethylene bis acetamide on the Commitment to Differentiation of Murine Erythro Cells," *Cancer Res.*, 37:440–444, 1977.

Freed et al., "Neocartilage formation in vitro and in vivo using cells cultured on synthetic biodegradable polymers," *J. Biomed. Mater. Res.* 27: 11–23 (1993).

Friend et al., "Hemogloblin Synthesis in Murine Virus Induced Leukemia Cells In Vitro: Stimulation of Erythroid Differentiation by Dimethyl Sulfoxide," *Proc. Natl. Acad. Sci. USA*, 69:378–382, 1971.

Gamet et al., "Effects of Short–Chain Fatty Acids on Growth and Differentiation of the Human Colon–Cancer Cell Line HT29," *Int. J. Cancer*, 52:286–289, 1992.

Gasiewicz and Rucci, "α–Naphthoflavone Acts as an Antagonist of 2,3,7,8–Tetrachlorodibenzo–p–Dioxin by Forming an Inactive Complex with the Ah Receptor," *Mol. Pharmacol.*, 40:607–612, 1991.

Grande et al., "The Repair of Experimentally Produced Defects in Rabbit Articular Cartilage by Autologous Chondrocyte Transplantation," *J. Orthop. Res.*, 7:208–218 (1989).

Gum et al., "Effect of Sodium Butyrate on Human Colonic Adenocarcinoma Cells: Induction of Placental–like Alkaline Phosphate," *J. Biol. Chem.*, 262: 1092–1097, 1987.

Gurdon, "The Generation of Diversity and Pattern in Animal Development," *Cell*, 68: 185–199, 1992.

Hausen and Riebesell, *The Early Development of Xenopus laeva*. Springer–Verlag, Berlin Heidelberg New York: Plates 7–10, 1991.

Leid et al., "Multiplicity Generates Diversity in the Retinoic Acid Signaling Pathways," *TIBS*, 427–433, 1992.

Leonard et al., "Amphibian Yolk Platelet Ultrastructure Visualized by Freeze–Etching," *J. Ultrastruct. Res.*, 40:1–24, 1972.

Lewis et al., "Morphological and Biochemical Changes in the Hepatic Endoplasmic Reticulum . . . ," *Mol. and Cell. Endocrin.*, 4:311–329, 1976.

Lu et al., "Identification of 3'–Methoxy–4'–nitroflavone as a Pure Aryl Hydrocarbon (Ah) Receptor . . . ," *Arch. Biochem. Biophys.*, 316(1):470–477, 1995.

Ma et al., "Protein Tyrosine Phosphorylation as an Indicator of 2,3,7,8–Tetrachloro–p–Dioxin Exposure In Vivo and In Vitro," *Biochem. Biophys. Res. Commun.*, 189(1):59–65, 1992.

Ma and Babish, "Acute 2,3,7,8–Tetrachlorodibenzo–p–Dioxin Exposure Results in Enhanced Tyrosylphosphorylation . . . ," *Biochem. and Biophys. Res. Commun.*, 197(3):1070–1077, 1993.

Marks et al., "Induction of Transformed Cells to Terminal Differentiation and the Modulation of Gene Expression," *Cancer Res.*, 47:659–666, 1987.

Merchant and Safe, "In Vitro Inhibition of 2,3,7,8–Tetrachlorodibenzo–p–Dioxin–Induced Activity by α–naphthoflavone . . . ," *Biochem. Pharmacol.*, 50(5):663–668, 1995.

Mintz and Ilmensee, "Normal genetically mosaic mice produced from malignant teratocarcinoma cells," *Proc. Natl. Acad. Sci. USA*, 72(9):3585–3589, 1975.

Montorzi et al., "*Xenopus laevis* Vitellogenin Is a Zinc Protein," *Biochem. Biophys. Res. Commun.*, 200(3):1407–1413, 1994.

Montorzi et al., "Vitellogenin and Lipovitellin: Zinc Proteins of *Xenopus laevis* Oocytes," *Biochemistry*, 34:10851–10858, 1995.

Morikawa et al., "Influence of Organ Environment on the Growth, Selection, and Metastasis of Human Colon Carcinoma Cells in Nude Mice," Cancer Res. 48:6863–6871, 1988.

Mueller et al., "Terminal Differentiation of Human Breast Cancer through PPARγ," Mol. Cell, 1:465–470, 1998.

Nominzu et al., "Zinc, Iron and Copper Contents of Xenopus laevis oocyte and Embryos," Mol. Reprod. Develop., 36:419–423, 1993.

Ockner et al., "Hepatic uptake of albumin–bound substances: . . . ," Am. J. Physiol., 245(1):G13–G18, 1983.

Ohlendorf et al., "Lipid and Polypeptide Components of the Crystalline Yolk System from Xenopus laevis," J. Biol. Chem., 252(22):7922–8001, 1977.

Ohlendorf et al., "Three–dimensional structure of the lipovitellin–phosvitin complex from amphibian oocytes," 272:28–32, 1978.

Olson et al., "A Monoclonal Antibody to Human Antiogenin Suppresses Tumor Growth in Athymic Mice," Cancer Research, 54:4576–4579, 1994.

Opresko and Wiley, "Receptor–Mediated Endocytosis in Xenopus Oocytes. I. Characterization of the Vitellogenin Receptor System," J. Biol. Chem., 262(5):4109–4115, 1987.

Opresko and Wiley, "Receptor–Mediated Endocytosis in Xenopus Oocytes. II. Evidence for Two Novel Mechanisms of Hormonal Regulation," J. Biol. Chem., 262(5):4116–4123, 1987.

Perdew and Hollenback, "Analysis of Photoaffinity–Labeled Aryl Hydrocarbon Receptor Heterogeneity by Two–Dimensional Gel Electrophoresis," Biochemistry, 29(26):6210–6214, 1990.

Pfhal, "Retinoids: Concepts for Separation of Desirable and Undesirable Effects in the Treatment or Prevention of Cancer," Hormones and Cancer, Ed. Vederlds, Birkhauser, Boston. pp. 127–146, 1996.

Phelan et al., "Activation of the Ah Receptor Signal Transduction Pathway to Bilirubin and Biliverdin," Archives of Biochemistry and Biophysics, 357:155–163, 1998.

Pierce and Speers, "Tumors as Caricatures of the Process of Tissue Renewal: Prospects for Therapy by Directing Differentiation," Cancer Res., 48:1996–2004, 1988.

Placzek et al., "Orientation of commissural axons in vitro in response to a floor plate–derived chemoattractant," Development, 110:19–30, 1990.

Placzek et al., "Induction of floor plate differentiation by contact–dependent, homeogenetic signals," Development, 117:205–218, 1993.

Poland et al., "Stereospecific, High Affinity Binding of 2,3,7,8–Tetrachlorodibenzo–p–dioxin by Hepatic Cytosol . . . ," J. Biol. Chem., 251(16):4936–4946, 1976.

Porquie et al., "Control of dorsoventral patterning of somitic derivatives by notochord and floor plate," Proc. Natl. Acad. Sci. USA, 90:5242–5246 (1993).

Preflow et al., "Transplantation of Human Prostatic Carcinoma into Nude Mice in Matrigel," Cancer Res., 51:3814–3817, 1991.

Redshaw and Follett, "The Crystalline Yolk–Platelet Proteins and their Soluble Plasma Precursor in an Amphibian, Xenopus laevis," Biochem. J., 124:759–766, 1971.

Sarraf et al., "Differentiation and reversal of malignant changes in colon cancer through PPARγ," Nature Medicine, 4:1046–1052, 1998.

Saunders and Gasseling, "Ectodermal–Mesodermal Interactions in the Origin of Limb Symmetry," Epithelial–Mesenchymal Interaction, Eds. Fleischmajer and Billingham, Williams and Wilkins, Baltimore, MD., Chapter 5, pp. 78–97, 1968.

Saxen, "Neural induction," Int. J. Dev. Biol., 33:21–48, 1989.

Schubert et al., "Induced Differentiation of a Neuroblastoma," Dev. Biol., 25:514–546, 1971.

Seifried and Gaylor, "Investigation of Microsomal Oxygenases of Biosynthetic Processes," J. Biol., Chem., 251(23):7468–7473, 1976.

Sergeev et al., "Role of Estrogens in Phenobarbitone–Sodium Salt Induction of Microsomal Enzymes of the Liver," Biulleten Ekspermentalnoi Biologii i Meditsiny (Bulletin of Experimental Biology and Medicine), 80(9):43–45, 1975.

Slaughter and Triplett, "Amphibian embryo protease inhibitor . . . ," Cell. Differ., 4:429–440, 1976.

Smith and Harland, Cell, "Injected Xwnt–8 RNA Acts Early in Xenopus Embryos to Promote Formation of a Vegetal Dorsalizing Center," 67:753–765, 1991.

Sokol et al., "A Mouse Macrophage Factor Induces Head Structures and Organizes a Body Axis in Xenopus," Science, 249:561–564, 1990.

Spemann H & Mangold H, "Induction of Embryonic Primordia by Implantation of Organizers from a Different Species," in B.R. Willier and J.M. Oppenheimer eds.), Foundations of Experimental Embryology. Hafner, New York, pp. 144–194, 1924.

Stephenson et al., "Metastatic Model for Human Prostate Cancer Using Orthotopic Implantation in Nude Mice," J. Cancer Inst., 84(12):951–957, 1992.

Stifani et al., "Vitellogenesis in Xenopus laevis and Chicken . . . ," J. Biol. Chem., 265(2):882–888, 1990.

Stone et al., "Collagen–Based Prostheses for Meniscal Regeneration," Clin. Orthop. Relat. Red., 252:129–135, 1990.

Strickland and Mahdavi, "The Induction of Differentiation in Teratocarcinoma stem cells by retinoic acid," Cell, 15:393–403, 1978.

Takigawa et al., "Chondrocytes Dedifferentiated by Serial Monolayer Culture From Cartilage Nodules in Nude Mice," Bone Miner., 2:449 (1987).

Tanabe and Kotani, "Relationship between the amount of the 'germinal plasm' and the number of primordial germ cells in Xenopus laevis," J. Embryol. Exp. Morphol., 31(1):89–98, 1974.

Tanaka et al., "Induction of Erythroid Differentiation in Murine Virus Infected Erythroleukemia Cells by Highly Polar Compounds," Proc. Natl. Acad. Sci. USA, 72: 1002–1006, 1975.

Tenhunen et al., "Microsomal Heme Oxygenase . . . ," J. Biol. Chem., 244(23):6388–6394, 1969.

Tickle et al., "Positional signaling and specification of digits in chick limb morphogenesis," Nature 254:199–202, 1981.

Timmins et al., "The Location of Bound Lipid in the Lipovitellin Complex," Science, 257:652–655, 1992.

Tontonoz et al., "Terminal Differentiation of Human Liposarcoma Cells Induced by Ligands for Peroxisome Proliferator–Activated Receptor and . . . ," Proc. Natl. Acad., Sci., USA, 94:237–241, 1997.

Vacanti et al., "Synthetic Polymers Seeded with Chondrocytes Provide a Template for New Cartilage Formation," Plast. and Reconstr. Surgery, 88:753–759, (1991).

van Straaten et al., "Effect of the notochord on the differentiation of a floor plate area in the neural tube of the chick embryo," *Anat. Embryol.*, 177:317–324 (1988).

Venugopal and Kumar, "Role of juvenile hormone in the synthesis and sequestration of vitellogenins in the red cotton stainer, *Dysderecus koenigii*," *Comp. Biochem. Physiol. Part C*, 127:153–163, 2000.

von Schroeder et al., "The use of polylactic acid matrix and periosteal grafts for the reconstruction of rabbit knee articular defects," *J. Biomed. Mater. Res.*, 25:329–339 (1991).

Wakitani et al., "Repair of Rabbit Articular Surfaces with Allograft Chondrocytes Embedded in Collagen Gel," *J. Bone and Joint Surgery*, 71B:74–80 (1989).

Wall, "The intracellular fate of vitellogenin in Xenopus oocytes is determined by its extracellular concentration during endocytoses," *J. Biol. Chem.*, 262:14779–14789, 1987.

Wallace, "Studies on Amphibian Yolk: IX. *Xenopus vitellogenin*," *Biochim. Biophys. Acta.*, 215:176–183, 1970.

Whitlock et al., "Cytochromes P450 5: induction of cytochrome P4501A1: . . . " *FASEB J.*, 10(8):809–818. Review, 1996.

Wiley et al., "The Structure of Vitellogenin. Multiple Vitellogenins in *Xenopus laevis* Give Rise to Multiple Forms of the Yolk Proteins," *J. Biol. Chem.*, 256(16):8626–8634, 1981.

Wolpert, "Positional Information and the Spatial Pattern of Cellular Differentiation," *Theor. Biol.*, 25:1–47, 1969.

Wooley et al., "Comparison of a Microneutralization Test in Cell Culture and Virus Neutralization Test in Embryonated Eggs for Determining Infectious Bronchitis Virus Antibodies," *J. Clin. Microbiol.*, 3(2):149–156, 1976.

Yamada et al., "Control of Cell Pattern in the Developing Nervous System: . . . ," *Cell*, 64:635–647, 1991.

Zacharewski et al., "Induction of Cytochrome P450-Dependent Monooxygenase Activities in Rat Hepatoma H–4–IIE Cells in Culture by 2,3,7,8-Tetrachlorodibenzo-p-Dioxin and Related Compounds: Mechanistic Studies Using Radiolabeled Congeners," *Arch. Biochem. Biophys.*, 272(2):344–355, 1989.

Janes et al., "Bilirubin Inhibits Proliferation in Cultured Normal Human Osteoblast–Like Cells: . . . ," abstract from *Gastrointerology*, 102(4) part 2, p. A827, #XP00801667 (1992).

Peters and Wiley, "Evidence that Murine Preimplantation Embryos Express Aryl Hydrocarbon Receptor," *Toxicology and Applied Pharmacology*, 134:214–221 (1995).

Phelan et al., "Activation of the Ah Receptor Signal Transduction Pathway by Bilirubin and Biliverdin," *Arch. Biochem. and Biophys.*, 357(1):155–163 (1998).

Thaler, "Bilirubin Toxicity in Hepatoma Cells," *Nature: New Biology*, 230(15):218–219 (1971).

Vassilopoulou–Sellin et al., "Bilirubin as an Inhibitor of Cartilage Metabolism: Effect on Avian Chondrocyte Proliferation in Cell Culture," *J. Bone and Mineral Res.*, 5(7):769–774 (1990).

Zaher et al., "The Involvement of Aryl Hydrocarbon Receptor in the Activation of Transforming Growth Factor–$\alpha$ and Adoptosis," *Mol. Pharm.*, 54:313–321 (1998).

Zhou et al., "Photosensitization of bilirubin on proliferation and DNA synthesis in ascitic hepatoma cells," *Acta Pharm. Sinica*, 17(2):164–166 (1996).

Zucker et al., "Inhibition of Breast Cancer Cell Proliferation by Unconjugated Bilirubin . . . ," abstract from *Hepatology*, 30(4) part 2, p. 498A, XP008016620 (1999).

English abstract of Chinese Patent No. CN 1185956 (XP–002240175).

English abstract of Chinese Patent No. JP 53081611 (XP–002240174).

English abstract of Japanese Patent No. JP 3047166 (XP–002240176).

English abstract of Japanese Patent No. JP 6183969 (XP–002240177).

* cited by examiner

COMPOUNDS AND METHODS FOR REGULATING CELL DIFFERENTIATION

This application claims the benefit of the filing date of provisional application No. 60/247,299 filed Nov. 10, 2000, provisional application No. 60/262,233 filed Jan. 17, 2001, provisional application No. 60/264,814 filed Jan. 29, 2001 and this application is a continuation-in-part of application No. 09/977,866 filed Oct. 15, 2001 which claims the benefit of provisional application No. 60/240,497 filed Oct. 13, 2000 each application of which is hereby incorporated by reference in its entirety for all purposes.

BACKGROUND OF THE INVENTION

Pattern Formation

Many types of communication take place among animal cells. These vary from long-range effects, such as those of rather stable hormones circulating in the blood and acting on any cells in the body that possess the appropriate receptors, however distant they are, to the fleeting effects of very unstable neurotransmitters operating over distances of only a few microns. Of particular importance in development is the class of cell interactions called embryonic induction; this includes influences operating between adjacent cells or in some cases over greater than 10 cell diameters (Saxen et al. (1989) Int J Dev Biol 33:21–48; and Gurdon et al. (1987) Development 99:285–306). Embryonic induction is defined as in interaction between one (inducing) and another (responding) tissue or cell, as a result of which the responding cells undergo a change in the direction of differentiation. This interaction is often considered one of the most important mechanism in vertebrate development leading to differences between cells and to the organization of cells into tissues and organs. Adult organs in vertebrates, and probably in invertebrates, are formed through an interaction between epithelial and mesenchymal cells, that is, between ectoderm/endoderm and mesoderm, respectively.

The effects of developmental cell interactions are varied. Typically, responding cells are diverted from one route of cell differentiation to another, by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) Cell 68:185–199).

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diversive cell types during tissue differentiation (Davidson, E., (1990) Development 108:365–389; Gurdon, J. B., (1992) Cell 68:185–199; Jessell, T. M. et al., (1992) Cell 68:257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) Cell 68:185–199).

The origin of the nervous system in all vertebrates, for example, can be traced to the end of gastrulation. At this time, the ectoderm in the dorsal side of the embryo changes its fate from epidermal to neural. The newly formed neuroectoderm thickens to form a flattened structure called the neural plate which is characterized, in some vertebrates, by a central groove (neural groove) and thickened lateral edges (neural folds). At its early stages of differentiation, the neural plate already exhibits signs of regional differentiation along its anterior posterior (A-P) and mediolateral axis (M-L). The neural folds eventually fuse at the dorsal midline to form the neural tube which will differentiate into brain at its anterior end and spinal cord at its posterior end. Closure of the neural tube creates dorsal/ventral differences by virtue of previous mediolateral differentiation. Thus, at the end of neurulation, the neural tube has a clear anterior-posterior (A-P), dorsal ventral (D-V) and mediolateral (M-L) polarities (see, for example, Principles in Neural Science (3rd), eds. Kandel, Schwartz and Jessell, Elsevier Science Publishing Company: NY, 1991; and Developmental Biology (3rd), ed. S. F. Gilbert, Sinauer Associates: Sunderland Mass., 1991). Inductive interactions that define the fate of cells within the neural tube establish the initial pattern of the embryonic vertebrate nervous system. In the spinal cord, the identity of cell types is controlled, in part, by signals from two midline cell groups, the notochord and floor plate, that induce neural plate cells to differentiate into floor plate, motor neurons, and other ventral neuronal types (van Straaten et al. (1988) Anat. Embryol. 177:317–324; Placzek et al. (1993) Development 117:205–218; Yamada et al. (1991) Cell 64:035–647; and Hatta et al. (1991) Nature 350:339–341). In addition, signals from the floor plate are responsible for the orientation and direction of commissural neuron outgrowth (Placzek, M. et al., (1990) Development 110:19–30). Besides patterning the neural tube, the notochord and floorplate are also responsible for producing signals which control the patterning of the somites by inhibiting differentiation of dorsal somite derivatives in the ventral regions (Brand-Saberi, B. et al., (1993) Anat. Embryol. 188:239–245; Porquie, O. et al., (1993) Proc. Natl. Acad. Sci. USA 90:5242–5246).

Another important signaling center exists in the posterior mesechyme of developing limb buds, called the Zone of Polarizing Activity, or "ZPA." When tissue from the posterior region of the limb bud is grafted to the anterior border of a second limb bud, the resultant limb will develop with additional digits in a mirror-image sequence along the anteroposterior axis (Saunders and Gasseling, (1968) Epithelial-Mesenchymal Interaction, pp. 78–97). This finding has led to the model that the ZPA is responsible for normal anteroposterior patterning in the limb. The ZPA has been hypothesized to function by releasing a signal, termed a "morphogen", which forms a gradient across the early embryonic bud. According to this model, the fate of cells at different distances from the ZPA is determined by the local concentration of the morphogen, with specific thresholds of the morphogen inducing successive structures (Wolpert, (1969) Theor. Biol. 25:1–47). This is supported by the finding that the extent of digit duplication is proportional to the number of implanted ZPA cells (Tickle, (1981) Nature 254:199–202).

In principle, induction means any process in which the developmental pathway of one cell population is controlled by signals emitted from another. For instance, embryonic inductive signals are key regulatory proteins that function in vertebrate pattern formation, and are present in important signaling centers known to operate embryonically to define the organization of the vertebrate embryo. For example, these signaling structures include the notochord, a transient structure which initiates the formation of the nervous system and helps to define the different types of neurons within it. The notochord also regulates mesodermal patterning along the body axis. Another distinct group of cells having apparent signaling activity is the floorplate of the neural tube (the precursor of the spinal cord and brain) which also signals the differentiation of different nerve cell types. It is also generally believed that the region of mesoderm at the bottom of the buds which form the limbs (called the "Zone of Polarizing Activity" or "ZPA") operates as a signaling center by secreting a morphogen which ultimately produces the correct patterning of the developing limbs. Moreover, inductive signals are required for cell differentiation and morphogenesis throughout vertebrate development. Thus, in addition to initiating differences between cells in early development, inductive signals are also involved in formation and maintenance of most, if not all, adult organs and tissues.

Growth factors are substances, such as polypeptide hormones, which affect the growth of defined populations of animal cells in vivo or in vitro, but which are not nutrient substances. Proteins involved in the growth and differentiation of tissues may promote or inhibit growth, and promote or inhibit differentiation, and thus the general term "growth factor" includes cytokines, trophic factors, and their inhibitors. Among growth, or neurotrophic, factors presently known are the transforming growth factors (TGF-alpha, TGF-beta, TGF-gamma). Transforming growth factor-beta appears to elicit a variety of responses in many different cell types.

Widespread neuronal cell death accompanies normal development of the central and peripheral nervous systems. Studies of peripheral target tissues during development have shown that neuronal cell death results from the competition among neurons for limiting amounts of survivor factors ("neurotrophic factors"). The earliest identified of these, nerve growth factor ("NGF"), is the most fully characterized and has been shown to be essential for the survival of sympathetic and neural crest-derived sensory neurons during early development of both chick and rat. Barde et al., U.S. Pat. No. 5,229,500, issued Jul. 20, 1993, describe nucleic acid sequences encoding brain derived neurotrophic factor ("BDNF"), as well as the BDNF protein. BDNF is suggested for treating Parkinson's Disease and Alzheimer's Disease. Additional uses (quite recently performed successfully) are for the identification of homologous regions between BDNF and NGF so as to identify and isolate additional members of the NGF family, and also to generate immunogen by antibodies directed toward BDNF or fragments.

Among TGF-beta members are the bone morphogenetic proteins (BMP). The BMPs have been indicated as useful in wound healing, tissue repair, and to induce cartilage and/or bone growth. For example, PCT Application 9309229, inventors Israel and Wolfman, published May 13, 1993, describes uses of proteins with bone stimulating activity such as bone fracture healing and possibly the treatment of periodontal disease and other tooth repair processes.

BMPs have potent effects during embryogenesis. One member, BMP-4, has been shown to have potent ventralizing effects in Xenopus embryos, leading to the differentiation of blood and mesenchyme and inhibiting the formation of dorsal tissues such as notochord, muscle, and nervous system. (See, e.g., Jones et al., Development, 115, pp. 639–647, 1991.) BMP-4 is expressed ventrally in the Xenopus embryo and its expression is increased by ventralizing treatments such as irradiation with ultraviolet light (UV), see Steinbeisser et al., EMBO J., in press, November 1994 issue. An inhibitor of ventralizing BMPs could have dorsalizing effects on tissue differentiation. There are precedents for such inhibitory interactions in the TGF-beta family, since activin, a dorsalizing factor, can be inhibited by a specific inhibitory protein designated inhibin in the Xenopus embryo (see, e.g., Hemmati-Brivanlou et al., Cell, 77, pp. 283–295, 1994).

Another family of neurotropic factors are the Wnts, which have dorsal axis-inducing activity. Most of the Wnt protein are bound to cell surfaces (see, e.g., Sokol et al., Science, 249, pp. 561–564, 1990). One member of the family, Xwnt-8, was described as to dorsal axis-inducing activity in Xenopus embryos by Smith and Harland in 1991, Cell, 67, pp. 753–765. The authors described using RNA injections as a strategy for identifying endogenous RNAs involved in dorsal patterning to rescue dorsal development in embryos that were ventralized by UV irradiation.

UV ventralization is useful to probe the normal response of a gene to dorsal/ventral cell identity because UV treated embryos reproducibly lack obvious dorsal structures (e.g., somites, notochord, and neural plate). In addition, gastrulae that has become extreme ventralized tadpoles form a radial blastopore lip at the time of normal ventral blastopore lip formation. This suggests that the mesoderm is behaving as though it is ventral in identity. Lithium chloride treatment respecifies the fate of cells along the anterior-posterior axis of the early embryo by contrast to UV irradiation, which causes centralization of embryos.

Identification of new proteins, polypeptides or compounds capable of modulating embryonic patterning and cellular differentiation would aid in the development of therapeutic treatments for a wide variety of conditions involving aberrant cellular proliferation.

The Aryl Hydrocarbon Receptor

The Aryl Hydrocarbon (Ah) receptor is an intracellular cytosolic protein found in higher vertebrates in several epithelial tissues. The effects of Ah receptor ligands are known almost entirely in regards to their effects on P4501A1 induction, an enzyme system that metabolizes certain xenobiotics (Landers and Bunce, 1991). The Ah receptor was discovered by Poland and co-workers and studied first as a high affinity binding protein for aryl hydrocarbons of toxicological importance, most notably 2,3,7,8-tetrachlorodibenzo-p-dioxin (TCDD) (Poland et al., 1976).

Dioxins or dioxin-like compounds are environmental pollutants produced as unwanted byproducts of common industrial processes such as paper bleaching, incineration and chemical manufacturing.

Dioxins or dioxin-like compounds are a loosely defined family of organochlorine molecules with close structural and chemical similarities. Additionally, these compounds, by virtue of their similar structure and chemistry, share a common mechanism of toxicity. The prototypical dioxin, and the best studied, is 2,3,7,8 Tetrachlorodibenzo-P-Dioxin (sometimes called 2,3,7,8-TCDD or TCDD or dioxin).

Besides 2,3,7,8 Tetrachlorodibenzo-P-Dioxin, this group of compounds include not only the dibenzo-p-dioxins, but also dibenzofurans, azobenzenes, dibenzo-ethers, certain polychlorinated biphenyls, certain polyaromatics and other compounds. Toxicity of these compounds is dependent on a planar, polyaromatic structure with lateral halogen substitutions.

The biochemical and physiological basis of dioxin toxicity has been the subject of intense scientific scrutiny. Animals vary in their susceptibility to dioxins and in their symptoms. In guinea pigs, as little as 600 ng per kg produces a lethal wasting syndrome. In humans, toxic responses to dioxin exposure include several proliferative aberrations such as hyperkerotinosis and hyperplasia. Despite much research in the area, the biochemical and physiological events that produce toxicity are poorly understood.

Although the ultimate physiological events that produce toxicity are poorly understood, it is generally agreed that toxicity of these chemically and structurally related dioxin-like compounds is due to their ability, by virtue of their chemical and structural properties, to bind to the intracellular Ah receptor. Although the ability of a compound to be a ligand of the Ah receptor is a requirement for dioxin-like toxicity, these compounds must also be able to promote transformation of the receptor to a DNA-binding form subsequent to ligand binding in order to be toxic. The transformation of the Ah receptor comprises a series of poorly understood events that include dissociation of the inactive receptor from a complex of proteins that include one or more molecules of the chaperonin HSP90, the formation of a new complex that includes HSP90-dissociated Ah receptor plus bound dioxin and the nuclear protein Aryl Hydrocarbon Nuclear Translocator (ARNT), and the binding of the Ah receptor/ARNT complex to specific DNA sequences.

These sequences, called Dioxin-Response Elements (DREs) or Xenobiotic-Response Elements (XREs), lie upstream of the promoter regions of certain genes, the most studied being the P4501A1 gene. The binding of the transformed Ah receptor and associated protein(s) to the DREs enhance transcription of the associated genes. The inappropriate expression of these genes are thought to be the early events in the pleiotropic response to dioxins. It is fundamental that dioxins, in order to be toxic, must be able to both bind to the Ah receptor and transform it into an active form, and that this binding/transformation couplet is the central and only defined biochemical event in the toxic effects of dioxins.

Different dioxin-like compounds, although they share a common mechanism of toxicity, have different toxic potencies that can differ by several orders of magnitude. The toxicity of an unknown mixture of dioxin-like compounds can vary considerably depending on the identity and concentrations of the congeners present. Thus, the concept of Toxic Equivalency Factors (TEFs) and Toxic Equivalence (TEQs) have been advanced by some scientists. TEFs are the fractional toxicity of a dioxin-like compounds compared to the most toxic, prototypical 2,3,7,8-TCDD. Published TEFs are arbitrarily assigned values based on consensus toxicity's in the scientific literature. TEQs are the estimated toxic potential of a mixture of these compounds calculated by adding their respective TEFs with adjustment for their respective concentrations. TEFs and TEQs have been promoted by the EPA in order to facilitate their risk and hazard assessment of these compounds when they occur as mixtures.

The sequence of known events when an agonist or Ah ligand binds to the Ah receptor can be summarized as follows. The Ah receptor in the unbound state is found bound to the chaperonin HSP90 and another poorly understood protein or proteins (Perdew and Hollenback, 1990). Agonists of the Ah receptor such as TCDD, upon binding to the receptor, alter the receptor (commonly referred to as "transformation") so that the liganded Ah receptor separates from the chaperonin complex, translocates to the nucleus, binds to the ARNT protein, binds to specific DNA sequences upstream of the P4501A1 gene sequence as the Ah receptor: ARNT complex, and enhances transcription of P4501A1.

Antagonists and inhibitors of the Ah receptor have not been well-studied. Research interest has focused on potent, toxic agonists of the Ah receptor such as TCDD. Research interest on antagonists of the Ah receptor has focused on understanding the biochemistry of the Ah receptor, interactions among man-made toxins, and as inhibitors of estrogen-mediated gene expression. Known antagonists of the Ah-receptor include some flavone derivatives (Gasiewicz and Rucci, 1991; and Lu et al., 1995) and synthetic aryl hydrocarbons (Merchant and Safe, 1995).

Ah receptor agonists and antagonists of plant and dietary origin are known (Kleman et al., 1994; Bjeldanes et al., 1991; and Jellinck et al., 1993). Interestingly, these compounds are thought to be anti-carcinogens, tumor promoters, or both, however, mechanisms of action remain unknown.

The biochemical effects of agonists of the Ah receptor are generally thought to be Ah receptor-dependent, that is, the potency of the toxic response is proportional to their ability transform the Ah receptor (Wheelock et al., 1996), or induce P4501A1 (Zacharewski et al., 1989). However, the induction of P4501A1 itself is probably not connected with most of the physiological effects of Ah receptor ligands. Ah receptor ligands can act as anti-estrogenic tumor dependent agents by virtue of the ability of the Ah receptor: ARNT complex to interfere with estrogen receptor-mediated transcription. TCDD effects on both cellular proliferation, and apoptosis may occur via perturbation of intracellular signal transduction systems involved with cellular proliferation and apoptosis, as evidenced with by intracellular protein phosphorylation (Ma, 1992), induction of protein-tyrosine kinases, and cyclin dependent kinases (Ma and Babish, 1993).

The natural function of the Ah receptor is unknown, however, deletion of the Ah receptor results in liver abnormalities and immune system impairment. Furthermore, the identification of any endogenous ligand has remained elusive, and how Ah receptor-mediated signaling interacts with cell cycle and apoptotic control is poorly understood, and a direct connection has not been established.

SUMMARY OF THE INVENTION

The present invention makes available methods and reagents for inhibiting cell proliferation or promoting cell differentiation comprising contacting the cell with a differeguline in a sufficient amount to inhibit cell proliferation or promote cell differentiation. Embodiments of the present invention are further directed to a method of regulating, modulating or altering cell differentiation comprising contacting a target cell or cells with a compound of the present invention in a manner to regulate, modulate or alter differentiation of the cell or cells from a present state to a differentiated state. Methods of the present invention include in vitro and in vivo methods.

The present invention further makes available methods for a number of applications, including the in vivo modulation of lipid metabolism; in vivo modulation of skin related processes (e.g., acne, psoriasis, aging, wrinkling, and the like); in vivo modulation of programmed cell death (apoptosis); in vivo modulation of malignant cell development, such as occurs, for example, in acute promyelocytic leukemia, mammary cancer, prostate cancer, lung cancer, cancers of the aerodigestive pathway, skin cancer, bladder cancer, and sarcomas; in vivo modulation of premalignant lesions, such as occurs with oral leukoplakia and the like; in vivo modulation of auto-immune diseases such as rheumatoid arthritis; in vivo modulation of fatty acid metabolism; and the like. Such applications can be expected to allow the modulation of various biological processes with reduced occurrence of undesirable side effects such as teratogenic effects, skin irritation, mucosal dryness, lipid disturbances, and the like. In vivo applications can be employed with a wide range of subjects, such as, for example, humans, rodents, sheep, pigs, cows, dogs, and the like.

DETAILED DESCRIPTION OF THE INVENTION

I. Overview

Figure 1:
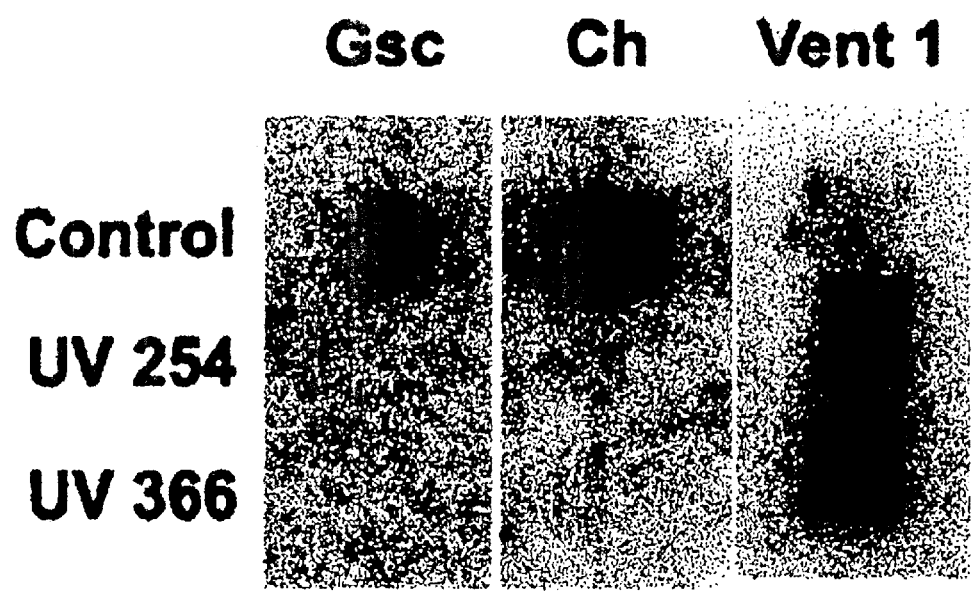
FIG. 1. Northern blots of RNA from UV irradiated stage 10.5 embryos. The dorsal markers goosecoid (gsc) and chordin (ch) and ventral one Vent 1 are present in control RNA. The two dorsal mRNAs are absent while the ventral marker, Vent 1, is present in both 254 and 366 nm-irradiated embryos.

The process of differentiation is fundamental to all biological organisms. It takes place at all stages of development from the embryo to the adult, the embryo is the product of a single cell, the egg, that is fertilized by a single sperm. The resultant embryonic cell then undergoes a series of divisions that produce many daughter cells with distinct and powerful properties. These cells are the primordial germ lines that are committed to form the three distinct categories of tissues: ectodermal, mesodermal and endodermal. The differentiation of these germ lines results in the establishment of multiple tissues that organize into organs. The adult preserves some precursor, undifferentiated cells that retain the capability to form committed stem cells that terminally differentiate. These cells serve to replenish the ones that have undergone the normal aging process and died, for example in bone marrow, gonads, bowel, skin cells, and others. Periodically, therefore, these precursor cells initiate the normal process of ordered change from a primitive to a mature cell through progressive differentiation that results in the formation of a terminally differentiated white blood cell, brush border intestinal cell, etc.

The normal differentiation process of these cells can be altered for diverse reasons during carcinogenesis. Thus, exposure to radiation, chemical carcinogens, viral infections, etc., can interrupt and block the differentiation events resulting in the accumulation of partially differentiated cancer cells, as for example, in leukemia. The pathology can be localized to any level in the differentiation process resulting in histological and biochemical phenotypes characteristic of that stage.

Reversal of the pathology described above is a feasible objective encompassed by the term cancer differentiation therapy and reviewed in 1986 (Pierce B G, Speers W C, *Cancer Res.* 48:1996–2004, 1988). The neoplastic phenotype is usually stable within an adult animal. For example, mouse teratocarcinoma cells implanted into adult mice will maintain their malignant phenotype for hundreds of passages. However, exposure of these, and other, cancer cells to particular chemical environments, such as those found in the early embryo, can reverse the neoplastic process. Thus, when teratocarcinoma cells from a black mouse are injected into the blastula of a white mouse, a chimeric animal is formed that is composed of normal black and white cells (Mintz B, Ilmensee J D, *Proc. Natl. Acad Sci. USA* 72:3585–3589,1975). The same teratocarcinoma cells, as well as acute promyelocytic leukemia cells, can be induced to terminally differentiate by all-trans retinoic acid (Strickland S, Mahdavi V, *Cell* 15:393–403, 1978). Similarly, erythroleukemias and other forms of leukemia cells (Tanaka M. et al., *Proc. Natl. Acad Sci. USA* 72:1002–1006, 1975; Fibach E. et al., *Cancer Res.* 37:440 –444, 1977; Friend C. et al., *Proc. Natl. Acad. Sci. USA* 69: 378–382, 1971; Huberman, E. et al., *Proc. Natl. Acad. Sci. USA* 76:1293–1297, 1971; Collins S J et al., *Proc. Natl. Acad. Sci.* USA 75: 2458–2462, 1978; Marks P A et al., *Cancer Res.* 47:659–666, 1987; Feakon E R et al., *N. Eng. J. Med.* 315:15–24, 1986), neuroblastoma cells (Schubert D S et al., *Dev. Biol.* 25:514–546, 1971), mammary cancer cells (Grubbs C J et al., *Cancer Res.* 37:599–602, 1977) and rhabdomyosarcoma, cells (Dexter D L, *Cancer Res.* 37: 3136–1140) 1977) have been shown to differentiate by exposure to chemicals such as hexamethylenebisacetamide, dimethyl sulfoxide, retinyl methyl ether, and N,N-dimethylformamide. Metastases to the lung of embryonal carcinoma have differentiated into mature teratomas following cytotoxic chemotherapy (Carr B I et al., *J. Urol.* 126:52–54, 1981). More recently, liposarcoma, colon (Tontonoz P et al., *Proc. Natl. Acad, Sci. USA* 94:237–241, 1997; Schwartz B et al., *Mol Cell Biochem.* 188:21–301, 1993; Sarref P et al., *Nature Medicine* 4:1046–1052. 1998; Gum J R et al., *J. Biol. Chem.* 262:1092–1097, 1987; Gamet L et al., *Int. J. Cancer* 52:286–289, 1992), and breast cancer cells (Mueller E et al., *Mol. Cell* 1:465–470,1998) were found to terminally differentiate when exposed to troglitazone (liposarcoma, colon and breast cancers) or butyric acid (colon cancer cells), These findings, therefore, indicate that in a suitable chemical environment, including that found in the embryo but usually not the adult, cancer cells are not stable and can be directed to differentiate into normal cells.

The above considerations make it apparent that the reversal of pathological conditions of differentiation that result in a progression of a cancer cell to a fully differentiated benign state is a major challenge whose achievement will be clearly aided by understanding the molecular processes that regulate as well as those that interrupt or alter differentiation itself.

Molecular messages and specific gene products are thought to participate in the differentiation processes in both the embryo and adult. Many of the pertinent molecules and genes have been identified. These include molecules believed to be components of the classical "organizer" (Spemann H & Mangold H, Induction of Embryonic Primordia by Implantation of Organizers from a Different Species. In B. R Willier and J. M. Oppenheimer (eds.), Foundations of Experimental Embryology. Hafner, N.Y., pp. 144–194, 1924) or to be directed by them, such as Vg1, activin, Wnt, Liml, Gsc, Xnot HNF3, chordin, noggin, follistatin (Smith W C et al., *Cell* 70:829–840, 1992; Hemmati-Brivanlou A et al., *Cell* 77:283–295,1994; Sasai Y et al., *Cell* 79:779–790,1994; Takada S et al., *Genes Dev* 8:174–189, 1994; Ang S L et al., *Cell* 79:561–574, 1994; Weinstein D C et al., *Cell* 78:575–588, 1994; and Dawid J B, *J. Biol. Chem.* 269:6259–6262, 1994), as well as Hox, Kr, Krox20, scratch, castor, spalt, cKr2, zic, etc. (Roark M et al., *Genes Dev.* 9:2384–2390,1995; Mellerick D M et al., *Neuron* 9:799–903, 1992; Kuhnlein R P et al., *EBB J.* 13:168–179,1994; Swiatek P J, et al., *Genes Dev.* 7:2071–2084, 1993; Bernard O et al., *Cell Growth Differ.* 5:1159–1171,1994; Schutz B et al., *Gene* 148:227–236, 1994; Nagai T et al., *Dev Biol.* 182:299–313, 1997; Kostich W A et al., *Dev. Biol.* 202:145–152, 1995; Mevel-Ninio M et al., *EMBO J* 10:2259–2266, 1991; Redeman N et al., *Nature London* 332:90–92,1988; Perrotti D et al., *Mol. Cell. Biol.* 15:6075–6097, 1995; Krishnaraju K et al., *Mol. Cell Biol.* 15:5499–507, 1995). However, most of these molecules are not available in sufficient quantities, if at all, to test their capability to induce terminal differentiation of cancer cells. Moreover, many of these molecules are themselves products of other pleiotropic, master signals such as the retinoids and other hormone ligands of the nuclear receptor superfamily of proteins (Leid M et al., *TIBS*:427–433, 1992; Pfhal, M, Retinoids: Concepts for Separation of Desirable and Undesirable Effects in the Treatment or Prevention of Cancer. In: Hormones and Cancer. Ed. M V Vederlds, birkhauser, Boston. pp. 127–146, 1996). Therefore, these master switch molecules, differegulines, are the ones that act at the earliest, decisive steps in differentiation and are most likely to act on cancer cells to drive their differentiation forward. If these master chemical signals did exhibit such properties with neoplastic cells and could be obtained in large quantities, they could serve as agents useful in the area of cancer treatment.

The oocyte is considered to be a source of these master switches. The choice of organisms for obtaining oocytes and identifying their differeguline content and metabolism are driven by a number of practical considerations. Mammalian eggs are unsuitable because they cannot be obtained in sufficient quantities, thus limiting the supply of available differegulines. Amphibian eggs are not limited in terms of quantity. Large numbers can be obtained and fertilized to obtain equally large numbers of embryos undergoing embryogenesis. Since the pertinent differegulines are present in both mammalian and nonmammalian organisms and are likely to be highly conserved through evolution, they would be the same (or very similar) in all species and could then be isolated from more accessible and available animals, tested and used with other cells.

It requires two to three years for *X. laevis* to produce mature eggs capable of being fertilized (Grant P, *J. Exp. Zool.* 124: 513–543, 1953). In marked contrast, and evidently as a direct consequence, once fertilization takes place, a tadpole with a full complement of organs derived from all three germ lines is formed in less than 3–4 days (Nieuwkoop, P D and Faber, J. Normal Table of *Xenopus laevis* (Daudin). 2nd edition. Amsterdam: North Holland Publ.Co. 1967). This means that it takes nearly 900-fold longer to mature a single egg cell than to make an entire multicellular, multi organ tadpole. To achieve this biological feat, *X. laevis* oocytes must produce and store the chemical signals required for differentiation and organogenesis and use them later during the period of rapid embryogenesis. These chemical signals, acting singly or in combination, commit the single primordial fertilized oocyte cell into the three germ lines whose stem cells are subsequently directed along specific differentiation paths. Ultimately this activity results in the formation of tissues and organs. Thus, *X. laevis* oocytes are an excellent system for isolation and identification of these master chemical signals while the embryo itself provides the means to test their function(s).

We have now discovered that biliverdin is the dorsalizing cytoplasmic determinant in *X. laevis* oocytes. The present invention therefore relates to compositions of biliverdin, or derivatives thereof as defined by Formula I, which modulate cell growth, such as by modulating cell proliferation and cell differentiation. The present invention is also directed to methods for inhibiting cell proliferation or promoting cell differentiation to regulate the repair and/or functional performance of a wide range of cells, tissues and organs. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein). Additionally, the subject methods may be performed on stem cells to promote or regulate a differentiated state in cultured cells.

While not wishing to be bound by any theory, the compounds described herein may act by binding to an aryl hydrocarbon receptor, such as described by Phelan et al., *Archives of Biochemistry and Biophysics* 1998, 357, 155–163. Aryl hydrocarbon receptors include proteins such as those whose sequences are known, for example, by GenBank Accession Nos. NP_037281, NP_033839, NP_001612, AAF70373, P35869, P41738, P30561, S58375, S59514, A46266, AAF15281, AAF15280, AAF15279, AAF15278, AAF01342, AAC59696, AAC60334, AAC95336, AAC95335, AAD15838, AAC60338, AAC60337, AAC60336, AAC60335, AAC35169, AAC35168, AAC35170, AAC35940, 2105366A, BAA19930, AAA92082, AAA92083, AAA92084, or a naturally occurring homolog of any of these receptors, e.g., having a sequence at least 90% identical, or at least 95% identical to any of the foregoing receptors. For additional insight into possible modes of action, see also Peitsch et al., *New Biology* 1990, 2, 197–206. Accordingly, the present invention contemplates modulating the proliferation and/or differentiation of a cell by treating the cell with a compound which binds to an aryl hydrocarbon receptor. Compounds which modulate cell differentiation or cell proliferation may also be included in pharmaceutical preparations, as described below, and administered to an animal to treat a condition as described in further detail below.

In another preferred embodiment, the subject method can be used as part of a treatment regimen for unwanted proliferation of transformed cells. For example, a differeguline may be useful for terminal differentiation therapy of a cancerous growth.

In another aspect, the present invention provides pharmaceutical preparations comprising, as an active ingredient, a differeguline such as described herein, formulated in an amount sufficient to inhibit, in vivo, proliferation or promote cell differentiation.

The subject treatments using differegulines can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II. Definitions

For convenience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Bum wounds" refer to cases where large surface areas of skin have been removed or lost from an individual due to heat and/or chemical agents.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "differeguline" refers to an agent which is capable of modulating cell proliferation or cell differentiation. Preferred differegulines are biliverdin, bilirubin and substituted derivatives thereof.

An "effective amount" of, e.g., a differeguline, with respect to the subject method of treatment, refers to an amount of the differeguline in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from 0.07–1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

The terms "epithelia", "epithelial" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

As used herein, "immortalized cells" refers to cells which have been altered via chemical and/or recombinant means such that the cells have the ability to grow through an indefinite number of divisions in culture.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

As employed herein, the phrase "members of the steroid/thyroid superfamily of receptors" (also known as "nuclear receptors" or "intracellular receptors") refers to hormone binding proteins that operate as ligand-dependent transcription factors. Furthermore, this classification includes identified members of the steroid/thyroid superfamily of receptors for which specific ligands have not yet been identified (referred to hereinafter as "orphan receptors"). All members of the intracellular receptor superfamily have the intrinsic ability to bind to specific DNA sequences. Following binding, the transcriptional activity of a target gene (i.e., a gene associated with the specific DNA sequence) is modulated as a function of the ligand bound to the receptor. Also, see Heyman et al., Cell, 68: 397–406 (1992), incorporated herein by reference.

The term "nail" refers to the horny cutaneous plate on the dorsal surface of the distal end of a finger or toe.

A "patient" or "subject" to be treated by the subject method can mean either a human or non-human animal.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidernolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "heteroatom" as used herein means an atom of any element other than carbon or hydrogen. Preferred heteroatoms are boron, nitrogen, oxygen, phosphorus, sulfur and selenium.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$–$C_{30}$ for straight chains, $C_3$–$C_{30}$ for branched chains), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thiofornate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aryl" as used herein includes 5-, 6-, and 7-membered single-ring aromatic groups that may include from zero to four heteroatoms, for example, benzene, pyrrole, fliran, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle," as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

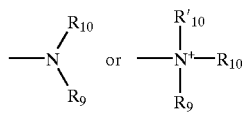

wherein $R_9$, $R_{10}$ and $R'_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The term "acylamino" is art-recognized and refers to a moiety that can be represented by the general formula:

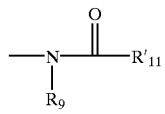

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art-recognized as an amino-substituted carbonyl and includes a moiety that can be represented by the general formula:

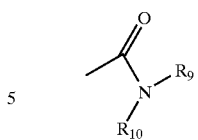

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethylthio, and the like.

The term "carbonyl" is art-recognized and includes such moieties as can be represented by the general formula:

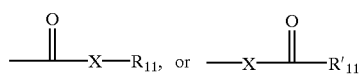

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiocarbonyl" group. Where X is a sulfur and R$_{11}$ or R'$_{11}$ is not hydrogen, the formula represents a "thioester." Where X is a sulfur and R$_{11}$ is hydrogen, the formula represents a "thiocarboxylic acid." Where X is a sulfur and R$_{11'}$ is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O-(CH$_2$)$_m$—R$_8$, where m and R$_8$ are described above.

The term "sulfonate" is art-recognized and includes a moiety that can be represented by the general formula:

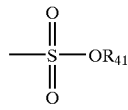

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

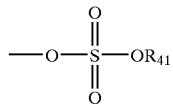

in which $R_{41}$ is as defined above.

The term "sulfonamido" is art-recognized and includes a moiety that can be represented by the general formula:

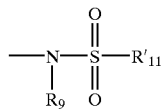

in which $R_9$ and $R'_{11}$ are as defined above.

The term "sulfamoyl" is art-recognized and includes a moiety that can be represented by the general formula:

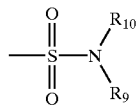

in which $R_9$ and $R_{10}$ are as defined above.

The terms "sulfoxido" or "sulfinyl", as used herein, refers to a moiety that can be represented by the general formula:

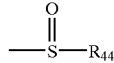

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

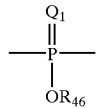

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

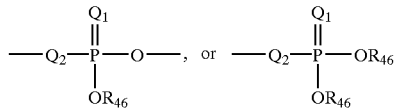

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

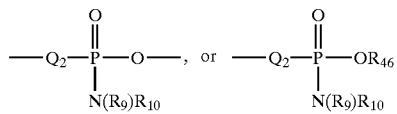

wherein $R_9$ and $R_{10}$ are as defined above, and $Q_2$ represents O, S or N.

A "phosphonamidite" can be represented in the general formula:

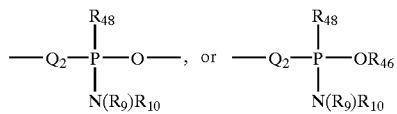

wherein $R_9$ and $R_{10}$ are as defined above, $Q_2$ represents O, S or N, and $R_{48}$ represents a lower alkyl or an aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se-$(CH_2)_m$—$R_8$, m and $R_8$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, tautomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit cell proliferation or promote cell differentiation), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: N.Y., 1991).

The term "ED$_{50}$" means the dose of a drug which produces 50% of its maximum response or effect. Alternatively, "ED$_{50}$" may mean the dose which produces a predetermined response in 50% of test subjects or preparations.

The term "LD$_{50}$" means the dose of a drug which is lethal in 50% of test subjects.

The term "therapeutic index" refers to the therapeutic index of a drug defined as LD$_{50}$/ED$_{50}$.

III. Exemplary Compounds of the Invention.

As described in further detail below, it is contemplated that the subject methods can be carried out using a variety of different small molecules which can be readily identified, for example, by such drug screening assays as described herein. For example, compounds useful in the subject methods include bilins. Bilins are a class of compound which include at least 3, optionally 4 or 5, substituted or unsubstituted nitrogen-containing five-membered rings, each ring separated from the next by a single carbon, wherein the carbons in the five-membered rings, and optionally some or all of the carbons which connect two rings, are unsaturated. Thus, bilins include compounds represented by general formula (I):

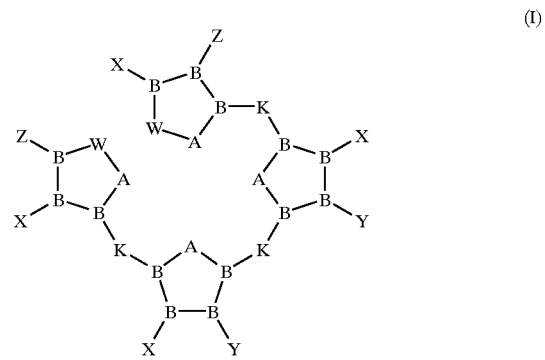

wherein
W, independently for each occurrence, represents —CE$_2$—, —C(=O)—, —C(=S)—, —C(=NH)—, or =CE—, preferably —C(=O)—, =CE—, —C(=NH)—, or —C(=S)—, even more preferably —C(=O)—, or —C(=S)—;

X, independently for each occurrence, represents a substituted or unsubstituted alkyl, alkenyl, or alkynyl group, preferably a lower alkyl group such as methyl, ethyl, etc.

Y, independently for each occurrence, represents a substituted or unsubstituted alkyl, alkenyl, or alkynyl group, optionally substituted with a carboxylic acid, amide, or thioacid moiety or derivative thereof, such as -alkylene-C(=V)OE, -alkenylene-C(=V)OE, -alkynylene-C(=V)OE, -alkylene-C(=V)SE, -alkenylene-C(=V)SE, -alkynylene-C(=V)SE, -alkylene-C(=V)NE$_2$, -alkenylene-C(=V)NE$_2$, -alkynylene-C(=V)NE$_2$, etc.;

V represents O, S, or NH, preferably O;

Z represents a substituted or unsubstituted alkyl, alkenyl, or alkynyl group, preferably a lower alkyl group such as vinyl, propenyl, butenyl, etc.;

A, independently for each occurrence, represents —NH— or —N=;

B, independently for each occurrence, represents a trisubstituted, sp$^2$-hybridized carbon atom;

K, independently for each occurrence, represents =CL— or —CL$_2$—; and

E, independently for each occurrence, represents H or lower alkyl, preferably H.

In certain embodiments, X, independently for each occurrence, represents a lower alkyl group, preferably having fewer than four carbon atoms.

In certain embodiments, Z, independently for each occurrence, represents a lower alkenyl group, preferably having fewer than four carbon atoms.

In certain embodiments, Y, independently for each occurrence, represents a carboxy-substituted lower alkyl group, such as carboxymethylene, carboxyethylene, carboxypropylene, etc. In certain embodiments, at least one occurrence of Y includes a carboxyl group, while in other embodiments, both occurrences of Y include a carboxyl group. In embodiments wherein Y includes an acidic moiety, such as a carboxyl group, a pharmaceutically acceptable salt of the compound may be used in the methods and preparations described herein.

In certain embodiments, the compound is biliverdin. In certain other embodiments, the compound is bilirubin.

In another aspect, compounds which may be useful in the methods of the present invention include bilin-like compounds, which bind to an aryl hydrocarbon receptor or otherwise promote differentiation or inhibit proliferation of a cell, having a structure of Formula II:

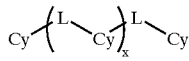

wherein, as valence and stability permit,

Cy, independently for each occurrence, represents a substituted or unsubstituted carbocyclic or heterocyclic ring, optionally including polycyclic systems;

L, independently for each occurrence, is absent or represents a linking group comprising from 1–3 units selected from —O—, —S—, —Se—, —NR$_8$—, —CE$_2$—, —CE=, —C(=V)—, such that L does not include two adjacent units selected from —O—, —S—, and —Se—, stated differently, at least 2 of —O—, —S—, and —Se— are nonadjacent;

E, independently for each occurrence, represents H or lower alkyl, preferably H;

X represents an integer in the range of 0 to 2;

V represents O, S, or NH, preferably O;

R$_8$ represents, independently for each occurrence, H or substituted or unsubstituted alkyl, alkenyl, alkynyl, cycloalkyl, cycloalkylalkyl, heterocyclyl, heterocyclylalkyl, aryl, aralkyl, heteroaryl, or heteroaralkyl.

In certain preferred embodiments, at least one occurrence of Cy, preferably two or even all occurrences, represents a substituted or unsubstituted aryl or heteroaryl ring, which may optionally be polycyclic. In certain embodiments, at least one occurrence of Cy includes a Lewis-basic atom, such as O, S, or N, either in the ring or on a substituent of the ring other than L, preferably in the ring, preferably two or even all occurrences of Cy. In certain preferred embodiments, at least one occurrence of Cy represents a substituted or unsubstituted heteroaryl ring, preferably two or even all occurrences. In preferred embodiments, at least one, two, or all occurrences of Cy represent a nitrogen-containing heteroaryl, such as imidazolyl, pyridyl, pyrrolyl, oxazolyl, thiazolyl, pyrazolyl, etc.

In certain preferred embodiments, two occurrences of L attached to an occurrence of Cy are bound to Cy in a 1,3-relationship, e.g., a meta relationship, i.e., the ring atoms of Cy to which the occurrences of L are attached are separated by exactly one ring atom.

In certain embodiments, any occurrence of Cy may be substituted with 1–5 substituents, such as halogen, lower alkyl, lower alkenyl, lower alkynyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$alkyl, —(CH$_2$)$_p$alkenyl, —(CH$_2$)$_p$alkynyl, —(CH$_2$)$_p$aryl, —(CH$_2$)$_p$alkyl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R$_8$, —(CH$_2$)$_p$SH, —(CH$_2$)$_p$S-lower alkyl, —(CH$_2$)$_p$S-lower alkenyl, —S(CH$_2$)$_n$R$_8$, —(CH$_2$)$_p$N(R$_8$)$_2$, —(CH$_2$)$_p$NR$_8$-lower alkyl, —(CH$_2$)$_p$NR$_8$-lower alkenyl, —NR$_8$(CH$_2$)$_n$R$_8$, and protected forms of the above.

In certain preferred embodiments, the subject inhibitors inhibit cell proliferation or promote cell differentiation with an ED$_{50}$ of 1 mM or less, more preferably of 1 μM or less, and even more preferably of 1 nM or less.

In certain embodiments, compounds of the present invention may be used in conjunction with apoptosis-inducing compounds thereby increasing their effect.

IV. Exemplary Applications of Method and Compositions

Another aspect of the present invention relates to a method of modulating a differentiated state, survival, and/or proliferation of a cell by contacting the cell with a differeguline according to the subject method and as the circumstances may warrant.

For instance, it is contemplated by the invention that, in light of the findings of an apparently broad involvement of differegulines in the formation of ordered spatial arrangements of differentiated tissues in vertebrates, the subject method could be used as part of a process for generating and/or maintaining an array of different vertebrate tissue both in vitro and in vivo. The differeguline, whether inductive or anti-inductive with respect to proliferation or differentiation of a given tissue, can be, as appropriate, any of the preparations described above.

For example, the present method is applicable to cell culture techniques. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a differeguline of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motorneurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be effected by contact with differegulines of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a differeguline.

Progenitor cells are thought to be under a tonic inhibitory influence which maintains the progenitors in a suppressed state until their differentiation is required. However, recent techniques have been provided which permit these cells to be proliferated, and unlike neurons which are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, in particular during epilepsy surgery, and more particularly during temporal lobectomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to allow outgrowth of specific cell types from a tissue. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6–8, more preferably close to pH 7, even more particularly about pH 7.4. Cells should be cultured at a temperature close to physiological temperature, preferably between 30° C.–40° C., more preferably between 32° C.–38° C., and most preferably between 35° C.–37° C.

Cells can be grown in suspension or on a fixed substrate, but proliferation of the progenitors is preferably done in suspension to generate large numbers of cells by formation of "neurospheres" (see, for example, Reynolds et al. (1992) *Science* 255:1070–1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3–4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3–10 days in vitro, the proliferating clusters (neurospheres) are fed every 2–7 days, and more particularly every 2–4 days by gentle centrifugation and resuspension in medium containing growth factor.

After 6–7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be controlled in culture by plating (or resuspending) the cells in the presence of a differeguline.

To further illustrate other uses of the subject differegulines, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of differegulines employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The differegulines can be used alone, or can be used in combination with other neurotrophic factors which act to more particularly enhance a particular differentiation fate of the neuronal progenitor cell.

In addition to the implantation of cells cultured in the presence of the subject differegulines, yet another aspect of the present invention concerns the therapeutic application of a differeguline to regulate the growth state of neurons and other neuronal cells in both the central nervous system and the peripheral nervous system.

As appropriate, the subject method can also be used in generating nerve prostheses for the repair of central and peripheral nerve damage. In particular, where a crushed or severed axon is intubulated by use of a prosthetic device, differegulines can be added to the prosthetic device to regulate the rate of growth and regeneration of the dendridic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the differeguline can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that differegulines are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising differegulines can also be utilized for both cell culture and therapeutic methods involving generation and maintenance of non-neuronal tissue.

In one embodiment, the present invention makes use of differegulines for controlling the development of stem cells responsible for formation of the digestive tract, liver, lungs, and other organs which derive from the primitive gut. Therefore, for example, differegulines of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of differegulines can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising differegulines can be utilized in liver repair subsequent to a partial hepatectomy.

The generation of the pancreas and small intestine from the embryonic gut depends on intercellular signaling between the endodermal and mesodermal cells of the gut. In particular, the differentiation of intestinal mesoderm into smooth muscle has been suggested to depend on signals from adjacent endodermal cells. In the context of the present invention, it is contemplated therefore that the subject differegulines can be used to control or regulate the proliferation and/or differentiation of pancreatic tissue both in vivo and in vitro.

There are a wide variety of pathological cell proliferative and differentiative conditions for which the differegulines of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject differegulines. For instance, it is contemplated by the invention that, in light of the apparent involvement of differegulines in the formation of ordered spatial arrangements of pancreatic tissues, the subject method could be used as part of a technique to generate and/or maintain such tissue both in vitro and in vivo. For instance, differegulines can be employed in both cell culture and therapeutic methods involving generation and maintenance of β-cells, and possibly also for non-pancreatic tissue, such as in controlling the development and maintenance of tissue from the digestive tract, spleen, lungs, and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. The subject differegulines, therefore, may be used to enhance regeneration of the tissue after anti-tumor therapy. Moreover, differegulines may be useful as part of a strategy for reshaping/repairing pancreatic tissue both in vivo and in vitro. Such physiopathologies are, in particular, type II diabetes, as well as cardiovascular diseases such as, for example, hypertension and atherosclerosis. The insulin-resistance disease state in a patient may be detected conventionally via the glucose tolerance test, and the treatment according to the invention may be initiated as soon as this test proves positive, even before any clinical manifestation of an onset of disease (preventive treatment). In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by a differeguline, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature β-cells can be observed. By utilizing the subject differegulines, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, the use of differegulines to affect tissue differentiation can be utilized as a means of maintaining graft viability.

The present method may be used to regulate regeneration of lung tissue, e.g., in the treatment of emphysema. The subject method can be used as part of a treatment of lung carcinoma and adenocarcinomas, and other proliferative disorders involving the lung epithelia.

Many other tumors may be affected by treatment with the subject compounds. Such tumors include, but are by no means limited to, basal cell carcinoma, medulloblastoma, meningioma, hemangioma, rhabdomyosarcoma, glioblastoma, sarcoma, renal carcinoma, thyroid carcinoma, bone cancer, lung cancer, chondrosarcomas, and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising differegulines can be used in the in vitro generation of skeletal tissue, such as from skeletogenic stem cells, as well as the in vivo treatment of skeletal tissue deficiencies. The present invention particularly contemplates the use of differegulines to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g., whether as a result of surgical intervention, removal of tumor, ulceration, implant, fracture, or other traumatic or degenerative conditions.

The methods and compositions of the present invention may be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a differeguline to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject agonists may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red*252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as a function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a differeguline during certain stages of the culturing process in order to manage the rate of differentiation of chondrocytes and the formation of hypertrophic chrondrocytes in the culture.

In another embodiment, the implanted device is treated with a differeguline in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. For instance, administration of a differeguline of the present invention can be employed as part of a method for regulating the rate of bone loss in a subject. For example, preparations comprising differegulines can be employed, for example, to control endochondral ossification in the formation of a "model" for ossification.

In yet another embodiment of the present invention, a differeguline can be used to regulate spermatogenesis. In a preferred embodiment, the differeguline can be used as a contraceptive. In similar fashion, differegulines of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a differeguline effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts,) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors.

According to the present invention, a treatment for such ulcers which includes application of a differeguline can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimrnmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of differegulines can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a differeguline preparation into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface. The subject method may also be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g., hypertrichosis. In an exemplary embodiment, differegulines can be used to manage hirsutism, a disorder marked by abnormal hairiness. The subject method can also provide a process for extending the duration of depilation.

The subject method can also be used in the treatment of folliculitis, such as folliculitis decalvans, folliculitis ulerythematosa reticulata or keloid folliculitis. For example, a cosmetic preparation of a differeguline can be applied topically in the treatment of pseudofolliculitis, a chronic disorder occurring most often in the submandibular region of the neck and associated with shaving, the characteristic lesions of which are erythematous papules and pustules containing buried hairs.

Regarding the in vivo modulation of lipid metabolism referred to above, apolipoprotein A-1 ("apoA1") is a major protein component of plasma high density lipoprotein (HDL) cholesterol. The circulating level of HDL in humans has been shown to be inversely correlated to the risk of atherosclerotic cardiovascular disease (ASCVD), the leading cause of morbidity and mortality in the United States, with a 3–4% increase in ASCVD for every 1% decrease in HDL cholesterol. Gordon et al., New Engl. J. Med., 321: 1311 (1989). While there are currently no good therapeutic regimes that increase HDL cholesterol, it can be expected that regulating synthesis of apoA1 can be utilized to affect plasma concentrations of HDL cholesterol and to decrease the risk of ASCVD. Reuben et al., Nature, 353: 265 (1991).

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a differeguline, e.g., which promotes quiescence or differentiation can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative preparation of the subject invention can be used to reverse the pathological epidermal activation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a differeguline composition in amounts sufficient to inhibit hyperproliferation of epidermal/epidermoid cells of the lesion.

Acne represents yet another dermatologic ailment which may be treated by the subject method. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative differeguline, particularly topical preparations, may be useful for preventing the transitional features of the ducts, e.g., hypercornification, which lead to lesion formation. The subject treatment may further include, for example, antibiotics and/or antiandrogens.

The present invention also provides a method for treating various forms of dermatitis. Dermatitis is a descriptive term referring to poorly demarcated lesions which are either pruritic, erythematous, scaley, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the subject method are disorders specific to non-humans, such as mange.

Thus, in another embodiment, the subject method can be used in the treatment of human cancers, particularly basal cell carcinomas and other tumors of epithelial tissues such as the skin. For example, differegulines can be employed, in the subject method, as part of a treatment for basal cell nevus syndrome (BCNS), and other human carcinomas, adenocarcinomas, sarcomas and the like.

In one embodiment, the subject method is used as part of a treatment or prophylaxis regimen for treating (or preventing) basal cell carcinoma (BCC). The subject method can also be used to treat patients with BCNS, e.g., to prevent BCC or other effects of the disease. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts of the skin and jaws, and in the central nervous system, medulloblastomas and meningiomas. The subject method can be used to prevent or treat such tumor types in BCNS and non-BCNS patients.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety of hyperplastic or neoplastic conditions affecting platelets. In certain embodiments, pharmaceutical preparations may be non-pyrogenic, i.e., the preparation does not elevate the body temperature of the treated patient.

The differegulines for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which maybe appropriate for the desired route of administration of the pharmaceutical preparation. The use of such media for pharmaceutically active substances is known in the art. Except insofar as any conventional media or agent is incompatible with the activity of the differeguline, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the differegulines suitable for veterinary uses, e.g., for the treatment of live stock or domestic animals, e.g., dogs.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a differeguline at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradernal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular differeguline employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutic effects of the first administered one is not entirely disappeared when the subsequent is administered.

V. Pharmaceutical Compositions

While it is possible for a compound of the present invention to be administered alone, it is preferable to administer the compound as a pharmaceutical formulation (composition). The differegulines according to the invention may be formulated for administration in any convenient way for use in human or veterinary medicine.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgrnent, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject differeglines from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present differegulines may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", J. Pharm. Sci. 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxyrnethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, $\beta$- and $\gamma$-cyclodextrin, dimethyl-$\beta$cyclodextrin and 2-hydroxypropyl-$\beta$-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active differeguline.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the differegulines in the proper medium. Absorption enhancers can also be used to increase the flux of the differegulines across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Ore., U.S.A., 1977).

VI. Synthetic Schemes and Identification of Active Differegulines a. Combinatorial Libraries The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of compounds represented above, can be screened rapidly in high throughput assays in order to identify potential differeguline lead compounds, as well as to refine the specificity, toxicity, and/or cytotoxic-kinetic profile of a lead compound.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

A variety of techniques are available in the art for generating combinatorial libraries of small organic molecules such as the subject differegulines. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject differegulines can be synthesized and screened for particular activity or property.

In an exemplary embodiment, a library of candidate differeguline diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate agonists or a substituent of a synthetic intermediate. According to the Still et al. technique, the library is synthesized on a set of beads, each bead including a set of tags identifying the particular diversomer on that bead. The bead library can then be "plated" with cells for which a differeguline is sought. The diversomers can be released from the bead, e.g., by hydrolysis.

The structures of the compounds useful in the present invention lend themselves readily to efficient synthesis. The nature of the structures, as generally described by formula I, allows the assembly of such compounds using combinatorial strategies. For example, the scheme below depicts formation of the cyclohexene core by a Robinson annulation wherein the enone is bound to a solid support. Alternatively, X or W may be used to tether the cyclohexene to the solid support. Many methods are known in the art for synthesizing polyalkenes, including condensations of phosphorous ylids (Wittig) or phosphonate anions (Horner-Emmons) with aldehydes, although many additional methods are known in the art. The strategy depicted below utilizes a thioester as an aldehyde precursor (Fukaiyama) to permit rapid, iterative extension of the polyene. An alkyllithium or other nucleophilic species, including hydride, may be added to the final polyunsaturated aldehyde in preference to the unsaturated ketone, and the resulting alcohol may then be acylated with an acid chloride or other acylating agent to afford a differeguline.

potentiate or antagonize differegulin function, e.g., modulation of cellular differentiation and/or proliferation. The antagonist therapeutics of the invention are those therapeutics which antagonize, or inhibit, a differegulin function. Such antagonist therapeutics are most preferably identified by the assays described herein or by use of known convenient in vitro assays, e.g., based on their ability to modulate and/or inhibit the interaction between a differegulin, such as biliverdin or a derivative thereof as defined by Formula I, and a receptor therefore, such as an aryl hydrocarbon receptor. In a preferred embodiment, the antagonist therapeutic is a biliverdin or a derivative thereof as defined by Formula I. It should be noted that in certain instances, an antagonist therapeutic may alternatively act as an agonist therapeutic, depending on the developmental history of the tissue being exposed to the therapeutic; preferably, suitable 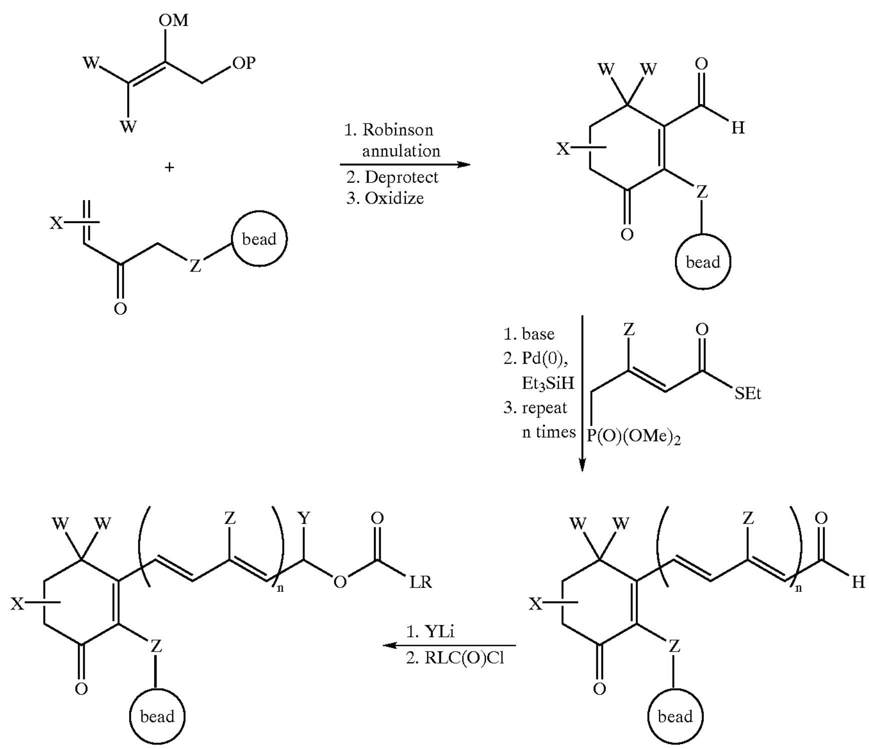 Many variations on the above and related pathways permit the synthesis of widely diverse libraries of compounds which may be tested as differegulines.

b. Screening Assays

There are a variety of assays available for determining the ability of a compound to inhibit cell proliferation or promote cell differentiation, many of which can be disposed in high-throughput formats. In many drug screening programs which test libraries of compounds and natural extracts, high throughput assays are desirable in order to maximize the number of compounds surveyed in a given period of time. Thus, libraries of synthetic and natural products can be sampled for other compounds which are differegulines. In addition to cell-free assays, test compounds can also be tested in cell-based assays. In one embodiment, cells can be contacted with a test agent of interest, with the assay scoring for, e.g., inhibition of proliferation of the cell in the presence of the test agent.

Broadly, in one embodiment, this invention provides agonist and antagonist therapeutics, which can either mimic, in vitro or in vivo assays, as described herein, may be utilized to determine the effect of a specific therapeutic and whether its administration is indicated for treatment of the affected tissue.

The agonist therapeutics of the invention, as described herein, promote, mimic, or potentiate the action of a diffegulin or the interaction between a differegulin and a receptor therefore. Such agonist therapeutics include, but are not limited to, biliverdin or derivatives thereof as defined by Formula I.

In vitro assays which can be used to determine whether administration of a specific agonist therapeutic or antagonist therapeutic is indicated, include in vitro cell culture assays in which a patient tissue sample is grown in culture, and exposed to or otherwise administered a therapeutic, and the effect of such therapeutic upon the tissue sample is observed. In one embodiment, where the patient has a malignancy, a sample of cells from such malignancy is plated out or grown in culture, and the cells are then exposed to a therapeutic. A therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. In a specific aspect, the malignant cell cultures are separately exposed to (1) an agonist therapeutic, and (2) an antagonist therapeutic; the result of the assay can indicate which type of therapeutic has therapeutic efficacy.

In another embodiment, a therapeutic is indicated for use which exhibits the desired effect, inhibition or promotion of cell growth, upon a patient cell sample from tissue having or suspected of having a hyper- or hypoproliferative disorder, respectively. Such hyperproliferative disorders include a wide variety of cancers such as colorectal, endometrial, gastric, hepatocellular, kidney (e.g., Wilm's tumor), medulloblastoma, melanoma, ovarian, pancreatic tumors, prostate, thyroid, uterine, etc. but are not limited to those described herein. Hypoproliferative disorders include diseases or conditions associated with insufficient cell proliferation, such as stimulation of tissue repair, tissue regeneration, wound healing, neovascularization, etc. but are not limited to those described herein.

In various specific embodiments, in vitro assays can be carried out with representative cells of cell types involved in a patient's disorder, to determine if a therapeutic has a desired effect upon such cell types.

In another embodiment, cells of a patient tissue sample suspected of being pre-neoplastic are similarly plated out or grown in vitro, and exposed to a therapeutic. The therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The translation of in vitro observations to in vivo conditions is greatly facilitated by a number of animal models that are currently in use to evaluate the efficacy of agents in the treatment of cancer. Some use animals that are immunodeficient (athymic) and others, ones with a fully functional immune system. The former allows for xenogeneic and syngeneic tumors to be grown and tested while the latter are best for syngeneic tumors grown under conditions where the animal's immunological system participates in the response to therapy (Olson Y A et al., Cancer Research 54, 45764579, 1994; Donehower L A et al., Nature 356: 215–221, 1992; Donchower L A et al., Cancer Biol 7:269–278, 1996). These animal models can be used to test the capability of candidate differegulin, such as those defined by Formula I, to induce terminal differentiation of a variety of tumors (Olson Y A et al., Cancer Research 54, 45764579,1994; Preflow T et al., CancerRes 51:3814–3817,1991; Morikawa et al., Cancer Res. 48, 6863–6871, 1988; Stephenson R A et al., J. Cancer Inst. 94:951–957,1992).

In another embodiment, compounds of the invention may be evaluated for the ability to induce cellular differentiation and/or proliferation using UV irradiated embryos from X. laevis. Briefly, in vitro fertilized embryos are exposed for ~30 minutes to a light source emitting at ~366 nm. After exposure, the embryos are contacted with a test compound of the invention and allowed to develop until the control group (unexposed embryos) reach stages ~35–40. The dorsoanterior index of the embryos can then be scored using standard published criteria (Kao, K R and Ellinson, R P, Dev. Biol. 127: 64–77 (1988)). Normal development is scored as a 5 and progressive ventral dominance is scored from 4 to 0, wherein 0 is undifferentiated and exhibits no dorsal structures. Alternatively, certain scoring scales are known where normal development is scored as a 0, progressive ventral dominance is scored from 0 to 4, wherein 5 is undifferentiated and exhibits no dorsal structures.

The invention now being generally described, it will be more readily understood by reference to the following examples which are included merely for purposes of illustration of certain aspects and embodiments of the present invention, and are not intended to limit the invention.

EXAMPLE I

Identification of Biliverdin as the Dorsalizing Cytoplasmic Determinant

The primary evocator of embryogenesis is an operational concept that describes the interaction between dorsalizing cytoplasmic determinants (DCD) and subcortical determinants prior to the first mitosis. These chemically uncharacterized partners switch on formation of downstream signals after the mid-blastula transition to evoke the dorsal axis. DCD is stable in organic solvents and destroyed by ultraviolet (UV) light. We have now discovered that biliverdin is the UV-sensitive molecule from Xenopus laevis oocytes that fulfills criteria for the long sought DCD. Stage 1 embryos exposed to either standard 254 or 366 nm UV light during 0.3 to 0.4 time fraction of their first cycle inactivates the cytoplasmic determinant. At either wavelength, the embryos are depleted of biliverdin and are fated to develop dorsal axis deficiency. In contrast, UV-irradiated embryos subsequently incubated with oocyte or commercially available biliverdin in $\mu$M amounts recover to form dorsal axial structures. In contrast, incubation with either in vitro photo transformed biliverdin or biliverdin IX$\alpha$ dimethyl ester does not induce recovery.

In 1924, Spemann and Mangold reported that gastrula tissue from the dorso-equatorial region induces an ectopic axis when transplanted into a recipient embryo. They named this axis-inducing region the organizer. This seminal finding established the significance of inductive signals to normal dorsal axis formation and morphogenesis, and stimulated the search for the identity of the responsible chemical substance (s).

Many molecules are now recognized to participate in this complex embryological process. Two broad categories of signals are now recognized. The first group is distributed initially to the vegetal cortex and cytoplasm of the egg and stage 1 embryo. Subsequently, they localize to the dorso-vegetal zone. They act early in the period following fertilization but before the first cleavage. The action of these early determinants is essential for the formation and/or activation of many molecules of the second group formed downstream after the mid blastula transition in the dorsal equitorial zone of the embryo. The latter ones have been extensively studied and include molecules formed and/or activated in both the dorsal (e.g., wnt, β-catenin, activin, siamois, XANF-1, goosecoid, Xnr3, noggin, chordin, TGF β, follistatin, xSOX3) and ventral (e.g., BMP4, FGF, Vent 1) zones of the embryo. However, the chemical identities of the first set have not been characterized. In fact, for over sixty years they have been described purely operationally as "cytoplasmic and subcortical determinants" since the actual number of molecules or their chemical nature remains unknown. A number of properties differentiate the two determinants. In contrast to the subcortical determinant, the cytoplasmic component is soluble and stable in organic solvents and its dorsalizing activity is lost following exposure of the mature, stage VI egg or stage 1 embryo to Uv light. The loss results in failure by the embryo to form a dorsal axis and derived structures, e.g., brain, eyes, spinal cord, among other organs. Reconstitution of Uv-exposed stage 1 embryos with oocyte cytoplasm or with many of the downstream dorsal signals synthesized after the mid-blastula transition described above rescues the embryos from dorsal axis deficiency. In addition, stage 1 embryos do not develop a normal dorsal axis when their vegetal-dorsal cortex is ablated, their vegetal hemisphere is irradiated by 54 nm UV light prior to their first mitosis, they are exposed to a cold temperature shock, incubated with colchicine or their cytoplasm is removed. The molecules of the embryo vegetal cytoplasm inactivated by irradiating with UV light can be reconstituted by transferring the cytoplasm from a non-irradiated egg/embryo into the irradiated one. The recipient irradiated embryo then recovers its capacity to form a dorsal axis.

Two "molecules" have been proposed to be the targets affected when oocytes, eggs and/or embryos are irradiated with UV light. Microtubules are proposed to carry out rotation of cortical determinants after fertilization. This phenomenon appears to be obviated following exposure to UV light. The latter is believed to destabilize microtubules leading to failure to place cortical determinants in the dorso-equatorial zone and, thereby, result in dorsal axis deficiency. Therefore, tubulin has been considered to be a target molecule for UV-irradiation. The other proposed target "molecule" is a cytoplasmic constituent first identified after irradiating oocytes instead of eggs. The affected target is distinct from tubulin since when the irradiated oocytes are subsequently fertilized, the resultant embryos develop a dorsal axis deficient phenotype yet still exhibit normal cortical rotation. The irradiated embryo's dorsalizing capacity is reconstituted by transferring cytoplasm from a donor, control stage 1 embryo. The presence of the latter target molecule can also be detected in stage 1 embryos by direct removal of their cytoplasm. This intervention results in dorsal axis deficient morphology without inhibiting cortical rotation. Thus, in both latter cases, the determinant present in the vegetal cortex is properly localized but the cytoplasmic factor is either inactivated by UV light or physically removed.

We have initiated studies aimed at identifying the chemical nature of this latter cytoplasmic factor of eggs and stage 1 embryos. The sequence of events described above demonstrates it acts in stage 1 embryos to affect MRNA synthesis detected later after the midblastula transition and into gastrula. This sequence of an early action followed by downstream effects on transcription is reminiscent of a ligand-receptor signaling system.

This conceptual insight together with the distinction between the two possible targets of UV light allowed us to design an experimental extraction procedure with organic solvents aimed at small, ligand-type molecule(s) that excludes proteins, such as tubulin. We were greatly aided by discovering that the cytoplasmic molecule(s) in question is inactivated not only with 254 but also with 366 nm UV light. This susceptibility to longer wavelength UV light allowed for discrimination between the target molecules described above since 366 nm UV light should not affect protein or nucleic acid constituents of the egg or embryo. According to the present invention, the UV sensitive cytoplasmic factor is biliverdin. It is present in the oocyte, egg and embryo cytoplasm, is photo transformed by both short and long wave UV light and may be essential for embryo dorsal axis development.

Embryo Irradiation with Either Short or Long Wavelength UV Lights

The source of the short wavelength emission (254 nm) was a UV G 11 lamp while the long wave emission (366 nm) was a UV SL 58 lamp (UVP, Inc., Upland, Calif.). For exposure to 254 nm, the embryos were placed on a quartz plate that transmits all UV G 11 lamp emissions. For exposure to 366 nm, the embryos were placed in polystyrene petri dishes that block transmission of light below 300 nm to avoid possible effects of shorter wavelengths.

Several hundred spawned eggs were fertilized in vitro and incubated at 16 to 18° C. The first mitosis at this ambient temperature of incubation occurred between 100–120 min after fertilization. The vegetal surfaces of some of these embryos were irradiated with one or the other sources of UV light within 10 min of fertilization for 20–30 min. Therefore, the UV-light exposure was applied well within the period of maximum effectiveness of UV light, in this case between $T_{fm}$=0.3–0.4 ($T_{fm}$ is the normalized time scale with a value of 1 representing the period from fertilization to the first mitosis). The embryos were not disturbed, touched or tipped from the moment of fertilization, during UV irradiation or for the duration of development. After control embryos had reached stages 30–35, the dorsal axis development of all experimental embryos was scored using standard morphological criteria defining their dorsal anterior index (DAI). A score of 5 defines a normal dorsal axis, 4 a microcephalic, 3 a cyclopic, 2 an anoptic, 1 an acephalic and 0 an adorsal embryo.

Purification of an UV-sensitive Molecule

An UV-sensitive species was localized to the cytoplasmic yolk platelets. Therefore, yolk platelets were isolated and used as starting material. Platelets were homogenized in one vol. of PBS, 5 mg/ml and in ascorbic acid and EDTA, adjusted to pH 7.3 with potassium hydroxide. The homogenate was extracted with acetone, dried and then dissolved in water. The pH was adjusted to 8 and nonpolar contaminants were removed by ethyl acetate extraction. The desired material was extracted into 1-butanol after saturation of the aqueous layer with sodium chloride. The product was dried and suspended in methanol and applied to a 0.9×17 cm Sephadex LH-20 column. Elution from the column with absolute methanol yielded a yellow-orange fraction at 0.3–0.5, a yellow fraction at 0.6–1.0 and a dark blue-green product at 1.4 to 1.7 column volumes. The fractions were dried by flash evaporation.

Each extract was dissolved in 1 ml of solvent A (3 mM ammonium acetate, pH 4.5, 20% in acetonitrile), and 250 μl aliquots were injected into a Phenomenex Jupiter 5μ $C_{18}$ HPLC column (300 Å, 250×4.6 mm). The column was connected to a Waters Alliance Chromatography System (Waters 2690 Separations Module interfaced with a Waters 996 Photodiode Array Detector). Solvent B was 100% acetonitrile. The gradient design was: 0% B from 0 to 5 min, 0–100% B linear gradient from 5 to 45 min, 100% B from 45 to 60 min. The eluate absorbance was recorded at a range of wavelengths from 250 to 550 nm by means of a diode array.

The cytoplasmic yolk platelet fraction that was photo transformed by UV light was identified in extracts of about 250 embryos irradiated with 366 nm UV light. The chromatogram of irradiated embryo extracts was compared to that of the non-irradiated ones to identify the photo transformed fraction. Once the retention time of the UV sensitive fraction was determined, the parent chemical species was isolated from control egg extracts. To confirm its UV sensitivity, an aliquot of the pertinent HPLC fraction in 44% acetonitrile and 3 mM ammonium acetate, pH 4.5, was irradiated in a cuvette in a Varian-Cary Bio 50 spectrophotometer at 366 nm. The pH was chosen to approximate that of intact yolk platelets. The wavelength was selected on the basis of the absorption spectra of the target fraction. The absorbance change was monitored at 375 nm. The resultant photo transformation product was then re-chromatographed by HPLC. For comparison, a separate aliquot of the intact molecule was irradiated with a monochromatic source at 254 nm from the spectrophotometer and similarly chromatographed.

Physical-chemical Characterization of the UV-sensitive Molecule

TLC sheets were silica gel 60F. Absorption spectra were obtained with a Varian Cary Bio 50 Spectrophotometer. Mass spectral analysis was performed in positive ion mode on a ThermoQuest LCQ Classic electro spray ionization/ion trap instrument. Aliquots incubated in 99.95-atom % methyl $d_3$ alcohol-d (Aldrich) were similarly analyzed to determine the number of exchangeable protons in the molecule. All NMR experiments were run at 25° C. on a Varian Unity Inova 500 spectrometer equipped with a 5 mm triple resonance IH{13C, 15N} probe head. The spectra were processed on a Silicon Graphics O2 workstation using VNMR software (Varian Instruments, version 6.1B). The details are described in Supporting Information.

Biological Activity of the UV-sensitive Molecule

The UV-sensitive fraction in the extracts studied is shown here to be biliverdin IXα, a substance that can be obtained commercially. Therefore, it was possible to analyze its biological activity with a fraction purified from oocytes or its commercially available counterpart and compare them to the effects of biliverdin photo transformed in vitro or of biliverdin dimethyl ester hydrochloride with its modified propionic side chains. Biliverdin IXα and derivatives were obtained from Porphyrin Products, Inc (Logan, Utah). Commercially available biliverdin IXα was subjected to the above extraction and chromatographic procedure beginning with the ethyl acetate step. The dimethyl ester required only HPLC purification. Photo transformed biliverdin was obtained by irradiating an aliquot of embryo culture solution containing biliverdin at the targeted concentration with 366 nm UV light for 12 h. The photo transformation of the biliverdin was verified spectrophotometrically by loss of the 375 nm absorption peak.

The biological activities of biliverdin and its derivatives were tested by adding each of them to the incubation solution of embryos after the termination of the UV light exposure to either 254 or 366 nm UV light and at selected time periods between $T_{ffm}$=0.4–2.5. Final concentrations of biliverdin ranged from 0.05 to 5 μM in less than 1% ethanol. The in vitro photo transformed biliverdin or the biliverdin dimethyl ester hydrochloride were added at a final concentration of 2.2 and 3.7 μM, respectively. An extinction coefficient of 51,000 was utilized to calculate their concentrations. All petri dishes were covered with aluminum foil to avoid light exposure. The extent of dorsal axis formation was analyzed by the morphological criteria described above.

The presence or absence of dorsal and ventrolateral markers was determined by northern blot analysis of RNA from control, 254 or 366 nm UV irradiated embryos. Goosecoid, chordin and Vent-1 cDNAs were labeled with $^{32}$P and used as hybridizing probes.

Additional studies were conducted as follows.

Extraction, Chromatography and Identification of the DCD

All procedures involving ovary manipulation, gradient loading, fraction collection and lipid extraction were carried out under subdued amber light or covered in aluminum foil when not possible. All samples were kept on ice to minimize exposure to heat. The dorsalizing cytoplasmic determinant was purified from ovaries of mature 6–7 cm female frogs. Ovaries from 30 frogs were suspended in one vol. of ice-cold stabilizing buffer (5 mg/ml ascorbic acid, 5 mg/ml EDTA in PBS, pH 7.3). The suspension was homogenized gently for about 5 min with a polytron homogenizer. Thirty five ml aliquots of the mixture was placed in plastic tubes layered onto 5 ml sucrose pellet (1.30 g/ml) to avoid damage to the platelets during centrifugation at 2000×g for 10 min. The supernatant was removed and discarded and the yolk platelets were washed with deionized water ×2. The platelets were suspended in three volumes of acetone, triturated and then stirred for fifteen min. at room temperature. The resultant slurry was filtered on a Buchner funnel using a 5 cm Whatman number 41 filter paper. The filter cake was washed with 35 ml acetone and then resuspended in the same volume of acetone as initially used. The extraction was repeated and the filtrates combined. The filtrates were placed at −20° C. for 1 hr, clarified through Whatman number 40 paper and concentrated to dryness by flash evaporation. The dry acetone extract was dissolved in 20 ml of water and the pH adjusted to 8 with saturated aqueous sodium bicarbonate. The resultant solution was extracted three times with 20 ml ethyl acetate. The yellow ethyl acetate extracts were discarded. The aqueous layer was saturated with sodium chloride and extracted 3 times with 15 ml of 1-butanol. The combined 1-butanol extracts were evaporated to dryness and then dissolved in 5 ml absolute methanol. The methanol solution was chromatographed on Sephadex LH-20 (0.9×18 cm) column. One ml fractions were collected and their UV absorbance monitored. The fractions with characteristic absorbance maximum at 379 nm were pooled, dried and suspended in 10% acetonitrile solution. The constituents were separated by HPLC using a Jupiter 5μ C18 300A 250×4.6 column (Phenomenex) and chromatography station (Waters) equipped with an automatic injector, in line vacuum pump, automatic gradient controller and absorbance detector. Buffer A was composed of 10% acetonitrile in ammonium acetate 3 mM, pH 6.5. Buffer B was acetonitrile 100%. The elution was carried out with the following gradient: 0 to 100% buffer B lineal increase in 45 min, 100% buffer B for 15 min, solvent flow 1 ml per minute, temperature 22° C. The eluted fractions were collected in the dark by encasing the fraction collector in an aluminum foil covered box to prevent exposure to the light. The dorsalizing determinant was identified by its retention time. Its absorption spectrum was obtained using a Varian Cary UV/Visible Spectrophotometer. The sample was scanned from 250 nm to 900 nm. The pertinent fractions were dried and stored at $-80°$ C.

The purified molecule was dissolved in 75:25 acetonitrile:water containing 1 nm ammonium acetate. It subjected to mass spectra analysis in positive ion mode on Thermo-Quest LCQ Classic electro spray ionization/ion trap mass spectrometer. Samples were infused into a 100 $\mu$m ID capillary with a 10 $\mu$m orifice. It was also subjected to analysis in negative ion mode and in the presence of deuterated methanol to determine the number of exchangeable protons.

A number of NMR experiments also were carried out. The NMR spectra were recorded in a Varian spectrometer equipped with a $^1H\{^{13}C, ^{15}N\}$ triple resonance probe head. The sample temperature was 25 degrees centigrade. All proton dimensions were acquired with a spectral width of 4227 HZ. All 2 dimensional spectra were acquired in phase sensitive mode using the States-TPPI method. $^1H$-$^1H$ TOCSY experiments were acquired at two mixing times, 25 and 75 milliseconds. 512 complex FID's were acquired with 16 scans and 3200 points per FID. The $^1H$-$^{13}C$ HMQC spectrum was acquired with a $^{13}C$ spectral width of 21361 Hz, 600 complex FID's with 64 scans and 1024 points per FID. The H:MBC spectrum was acquired with a $^{13}C$ spectral window of 27644 Hz, 600 complex FID's with 192 scans and 2048 points per FID. The delay for long range coupling was set to 55 milliseconds. The DEPT-HMQC spectrum was acquired using the method of Kessler et al with an editing pulse of 180 degrees to designate between methyl, methylene and methine carbons 512 complex FID will be acquired with 128 scans and 1024 points per FID. All other parameters were as in the HMQC spectrum.

Dorsalizing Activity of Candidate DCD

Stage 1 embryos were exposed to UV-light source emitting at 366 nm (Mineralight UVSL-58, Ultraviolet Products, Inc., San Gabriel, Calif.) as described and then incubated in the presence of pure candidate DCD or commercially available biliverdin (Sigma-Aldrich, St. Louis, Mo.) at final concentrations from 0.05 to 1.2 $\mu$M in less than 1% ethanol. The concentrations were calculated using a molar extinction coefficient of 51,000. One group of embryos was not exposed to UV light but was incubated in the presence of 0.5 $\mu$M of candidate DCD.

Additional experimental protocols were conducted or as identified as follows.

Emission Spectra of Ultraviolet Lamps

The emission spectra of several ultraviolet lamps, that are commonly used in the laboratory and described in the pertinent literature, were analyzed with an SX.18MV Emission Photomultiplier (Applied PhotoPhysics, Surrey UK) at a capture time of 50 ms. The manufacturer of the lamps (UVP Inc., Upland, Calif.) categorized the lamps in short/254 nm and long/366 nm wavelengths that indicate the presumed predominant emission wavelength and peak. The factory filter attached to the lamps was removed in some measurements. In others, the spectra was obtained after interposing either a polystyrene petri dish similar to the one used for the irradiation of embryos in this report, or a quartz slab similar to the those used by other experimenters. The plots represent the relative intensity of the emitted wavelengths. The lamp model is indicated on the side of each graph. Band peaks are marked in nanometers. The short wavelength/254 nm series lamps emit with a polychromatic spectrum that include a band that peaks at 254, 313 and 366 nm. Quartz allows the transmission of all the wavelengths. In some lamps the predominant emission wavelength was not 254 nm but longer ones were measured. The long wavelength/366 nm series lamps emit a more monochromatic spectrum with a broad band that peaks at 366 nm. When the factory filter is removed, other longer wavelengths are registered. Polystyrene allows the transmission of the broad band. The range of the emission bands of the lamps is comparable to those provided by the manufacturer, although we found variable relative intensities in different lamps. In the models UV SL 25 and UV SL 58 (a) the intensity of the band peaking at 254 nm (often assumed to represent the predominant wavelength) is either lower or equivalent to the other bands.

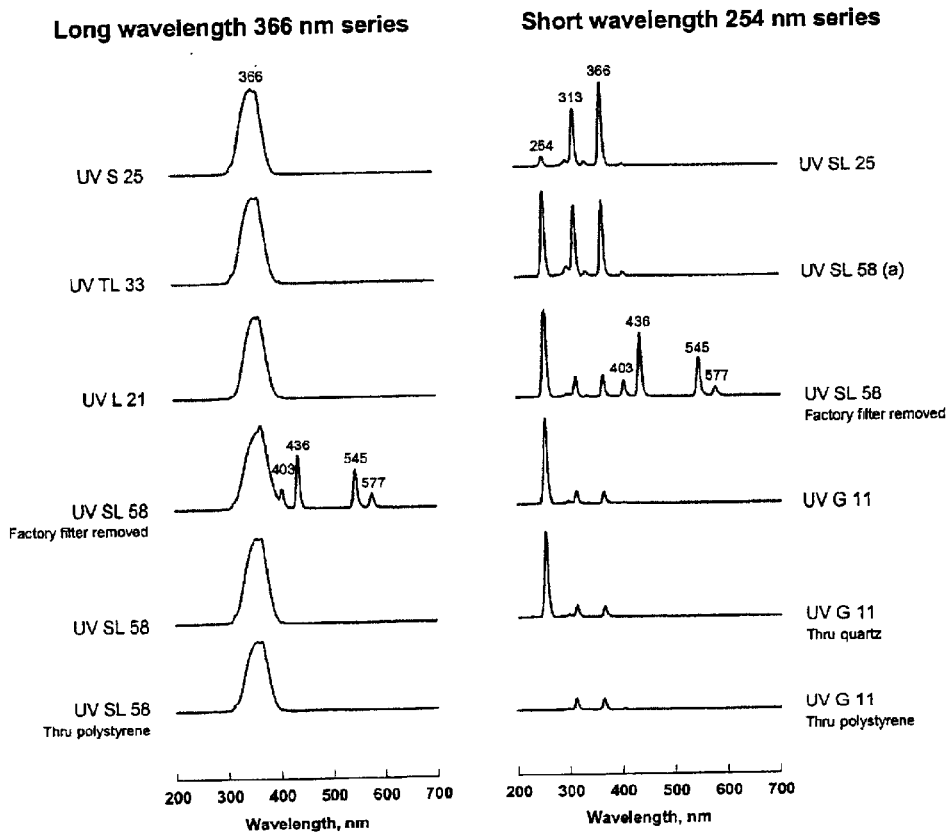

*Xenopus laevis* stage I embryos were placed in polystyrene petri dishes and exposed to 366 nm ultraviolet light using a UV SL 58 lamp (UVP Inc., Upland, CA). The petri dishes were analyzed for wavelength absorption with a Varian-Cary Bio 50 Spectrophotometer. Air was used as a baseline. The emission spectrum of the ultraviolet lamp is overlaid. The polystyrene petri dish has a high absorbance below 300 nm (cut off) and allows full transmission of the UV lamp band that peaks at 366 nm. The graded gray area represents the wavelength range to which the embryos were exposed.

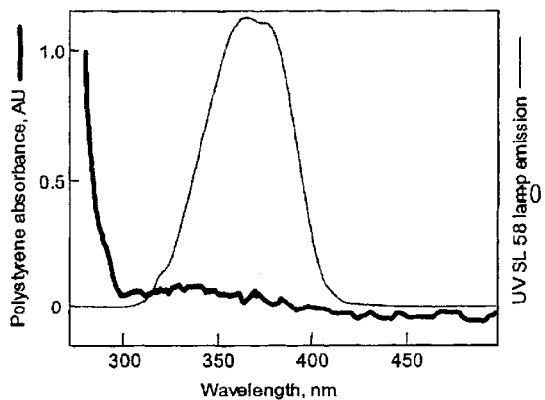

The selection of the 366 nm UV lamp was based on several observations: a) the monochromatic emission spectrum of the $UV_{366\ nm}$ lamp, b) the teratogenic effect of $UV_{366\ nm}$ light on embryos as we demonstrate in this report, c) the advantage of using convenient plastic petri dishes for manipulation and simultaneous irradiation of a large number of embryos, d) the wavelength transmission cut-off value of the polystyrene petri dishes at 300 nm avoids irradiation at shorter wavelengths to other potentially photosensitive molecules, e) the photosensitivity of biliverdin to 366 nm as we demonstrate in this report and f) the presence of this particular wavelength in the emission spectrum of the "254 nm short wave" series UV lamps that has been used by other investigators in teratogenic experiments as indicated in the literature.

Purification of a Photo Sensitive Molecule

Procedures involving ovary, oocyte, egg or embryo manipulation, gradient loading, fraction collection and extraction with organic solvents were carried out under subdued amber light or light protection with aluminum foil. Solvents were HPLC grade. The cytoplasmic substance was purified from ovaries or spawned eggs of mature frogs. Initially, the ovary of one 9-cm pigmented female frog, or its spawned eggs, was suspended in one vol of ice-cold stabilizing buffer (PBS, 5 mg/ml in ascorbic acid and EDTA, adjusted to pH 7.3 with sodium hydroxide) and homogenized with a Dounce tissue grinder. The homogenate was extracted with 2 vol of extraction buffer ethyl acetate:methyl acetate 8:1 with 50 µg/ml of butylated hydroxytoluene. The samples were placed on a rotator for 20 min at 4° C., centrifuged at 1000×g for 10 min and the organic layer removed and stored on ice. The extraction procedure was repeated and the organic layers were pooled. The product was dried with a stream of UHP nitrogen in the dark (procedure A).

The cytoplasmic yolk platelets are the sole location of the UV-sensitive species. Therefore, yolk platelets were used as starting material for an improved method of isolation (procedure B), which yielded sufficient pure material for chemical and biological characterization. The ovaries of 4 frogs, 92 ml, were suspended in 0.75 vol of the above ice-cold stabilizing buffer and the suspension was homogenized at low speed at 0° C. for 5 min with a Polytron (Brinkmann). Thirty-five ml aliquots of the mixture were layered onto 5-ml sucrose pellets (1.30 g/ml) in plastic tubes to avoid damage to the platelets during centrifugation at 2000×g for 10 min. The supernatant was discarded and the yolk platelets were washed twice with deionized water.

The yolk platelet pellet, 43 g, was triturated with 100 ml of acetone and stirred further for 15 min at room temperature. The slurry was filtered on a Buchner funnel using Whatman No. 41 paper and the filter cake washed with 15 ml of acetone. The filter cake was resuspended in 100 ml of acetone, stirred for 15 min and filtered as before. The combined filtrates and wash were kept at −20° C. for 1 hr, clarified by filtration through Whatman No. 40 filter paper and concentrated to dryness by flash evaporation and in vacuo over phosphorus pentoxide. An aqueous solution, 8 ml, of the dry acetone extract was adjusted to pH 8 with saturated sodium bicarbonate, and extracted 3 times with 8 ml of ethyl acetate. The yellow ethyl acetate extracts were discarded. The aqueous layer was saturated with sodium chloride and extracted twice with 8 ml of 1-butanol. The combined butanol extracts were flash evaporated and dried over phosphorus pentoxide to yield a green syrup. This product was suspended in 2.5 ml of absolute methanol and the supernatant applied to a 0.9×17 cm Sephadex LH-20 column prepared from 4 g of solid suspended in absolute methanol. Elution of the column with absolute methanol yielded a yellow-orange contaminant at 0.3–0.5, a yellow contaminant at 0.6–1.0 and the desired dark blue-green product at 1.4 to 1.7 column volumes. The pooled fractions were dried by flash evaporation. The samples were submitted to fractionation by the HPLC procedure described above. The pertinent fractions were dried and ammonium acetate removed in vacuo over phosphorus pentoxide and potassium hydroxide pellets. The sample stored at −80° C.

A chromatography station (Waters) equipped with an automatic injector, in-line pump, automatic gradient controller and absorbance detector was used for reversed-phase HPLC. The extracts were dissolved in 1 ml of solvent A (20% acetonitrile, 3 mM ammonium acetate, pH 4.5) and 250 µl aliquots were loaded onto a Phenomenex Jupiter 5 µ $C_{18}$ 300 Å 250×4.6 mm column. Samples applied at 1.5 ml/min and eluted at the same rate with a linear gradient (solvent B, 100% acetonitrile). Peaks were detected at both 340 and 254 nm. Pooled fractions were dried under UHP nitrogen.

Physical-Chemical Characterization

TLC sheets were silica gel 60F from Riedel de HaNn. Absorption spectra were obtained with a Varian Cary Bio 50 Spectrophotometer. Mass spectral analysis was performed in positive ion mode on a ThermoQuest LCQ Classic electro spray ionization/ion trap instrument. Samples, dissolved in 75:25 acetonitrile:water were infused into a 100 µm i.d. capillary with a 10 µm orifice. Aliquots incubated in 99.95 atom % methyl $d_3$ alcohol-d (Aldrich) were similarly analyzed to determine the number of exchangeable protons. Samples for NMR were prepared in the same perdeuterated methanol under dry nitrogen. All NMR experiments were run at 25° C. on a Varian Unity Inova 500 spectrometer equipped with a 5 mm triple resonance 1H{13C, 15N} probe head. Unidimensional proton spectra were acquired with a spectral window of 11 ppm, a recycle time of 4 s, and 64 scans.

The FID contained 16K data points. A TOCSY spectrum was acquired with a spectral window of 8 ppm in t2 and t1. A total of 512 complex FID's were acquired, each with 2048 points, and 32 scans. The TOCSY mixing time was 75 ms, and the recycle time was 2 s. A double quantum filtered COSY experiment was performed with the same parameters as the TOCSY spectrum, except that each FID contained 4096 points. A $^1$H-$^{13}$C DEPT-HMQC spectrum was acquired with a spectral window of 8 ppm in t2, and 160 ppm in t1. A total of 256 complex FID's were acquired, each with 1024 points, and 64 scans. A $^1$H-$^{13}$C HMBC spectrum was acquired with a spectral window of 8 ppm in t2, and 220 ppm in t1. A total of 256 complex FID's were acquired, each with 2048 points, and 128 scans. The delay for multiple bond transfer was 55 ms. The spectra were processed on a Silicon Graphics O2 workstation using VNMR software (Varian Instruments, version 6.1B). All 2D spectra were zero-filled twice in t1 prior to Fourier transformation. Proton NMR assignments were confirmed according to published methodology, and by comparison to spectra of commercial biliverdin IXα. All assignments refer to the numbering scheme in FIG. 6C.

The one-dimensional $^1$H spectrum is consistent with that of biliverdin IXα in terms of chemical shift distribution, and number of protons as determined by integration. The α, β, γ and δ isomers of biliverdin are easily identified by differences in chemical shifts using the observations of Bonnett and McDonagh. For example, only the alpha and beta isomers have a single resonance above 2.0 ppm, and of these two, only the alpha isomer has one triplet due to the equivalent β-methylene protons in the two carboxyethyl side chains. This pattern is clearly evident in both the molecule of interest, and in the spectrum of commercial biliverdin IXα. The vinyl protons were identified from analysis of two-dimensional TOCSY, and DQFCOSY spectra.

84

No attempt was made to assign the NH resonances, or to distinguish between the resonances of individual methyl groups. Of significant value is the comparison of spectra from the molecule of interest and commercial biliverdin IXα. The chemical shifts and coupling patterns are identical, providing further evidence that the molecule is biliverdin IXα. Additionally, the coupling between the carbonyl carbon and the alpha and beta methylene protons of the carboxyethyl side chains were verified from the DEPT-HMQC and HMBC spectra (data not shown).

Biliverdin was purified by HPLC as described above. Aliquots of the purified material were placed in quartz cuvettes and irradiated for 30 minutes with either 366 or 254 nm wavelengths. The source of the monochromatic light was a Varian-Cary Bio 50 Spectrophotometer. The signal read was the absorption at the respective wavelengths and the average integration time for each data point was 10 seconds. The absorbance units of the two wavelength plots were normalized for an initial ratio value of 1 at t = 0 min. The rate of photo transformation expressed by the extinction of the signal or progressive change in the slope of the curve, indicates that biliverdin is photosensitive to at least the two irradiation wavelengths.

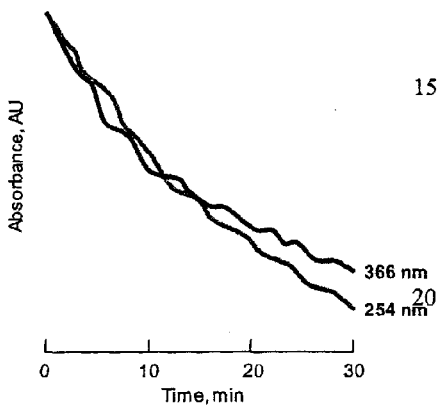

Additional experimental protocols were carried out as follows.

Sources of Bilins. A stock solution of modified Steimberg's buffer (5.8 mM NaCl, 0.67 mM KCl, 0.4 mM $MgSO_4$, 3.4 mM $CaCl_2$, 4.6 mM Tris, 6 mM $HNO_3$, pH 7.4) was prepared with compounds of highest purity, diluted and used as described below. Oocytes at different stages of maturation were obtained from 6-7 cm long female *X. laevis* frogs. Frogs were anesthetized by immersion in 0.1% p-aminobenzoic acid ethyl ester, 0.3% $KHCO_3$, pH 7.5. The abdominal cavity was opened using sterile conditions to remove the ovarian lobes. The fibrous sheath of the ovarian lobes was removed by treatment with 0.57% collagenase for 45 minutes at 37° C. Oocytes at each stage of maturation were collected by first separating smaller stages 1–4 from larger stages 5 and 6 eggs by filtering the total oocyte suspension through a size 30 mesh screen placed in a glass funnel. The screen was fixed at a position 15 cm above the bottom in a glass beaker totally immersed in 20% Steimberg buffer. The eggs were poured into the funnel. Stages 1–4 passed through the screen while stage 5 and 6 remained on the screen. Stages 3, 4, 5, and 6 then were separated on the basis of their size and morphology using Dumont's criteria. The separated oocytes were weighed, snap frozen in liquid nitrogen, and stored at −80° C.

Embryos were obtained by in vitro fertilization techniques well known to those skilled in the art. Fifty units of pregnant mare's serum were injected into the dorsal lymph sac of 6–7 cm female *Xenopus laevis* frogs. 92 hours later, 500 U human chorionic gonadotropin (hCG) were administered again into the dorsal lymph sac. Within 12–14 hours a given frog produced greater than 1000 eggs that were fertilized in vitro. Frog testes were placed in 60×15 mm dishes containing 80% Steimberg's solution, and macerated to prepare a sperm solution. Viability was confirmed by observing motility using a light microscope. The female was induced to shed eggs by massage of the abdomen and the area above the cloacal valves. For fertilization, eggs were deposited directly into the sperm solution. Once this was achieved, all embryos were dejelled using a 2% L-cysteine solution, pH 8.0. The embryos remained in this solution for 5 minutes and were then washed 5× in 20% Steimberg's solution. Embryos were then transferred to 150×25 mm dishes containing 20% Steimberg's solution. The solution was changed daily for the first week after which the embryos were placed in a 10 gallon tank containing aerated Milli-Q water. Progression of embryonic development was scored by light microscopic observation of gross morphological changes according to Nieuwkoop and Faber. Once the embryos reached the desired stage of maturation they were counted, snap frozen in liquid nitrogen, and stored at −80° C.

Approximately 1000 control, unfertilized eggs were shed directly into plastic dishes containing only 20% Steimberg's solution but no sperm. These were dejelled as above, counted, and snap frozen in liquid nitrogen. Eggs from 6–7 cm albino female frogs were similarly collected.

Bilin Extraction. All procedures involving oocyte manipulation, gradient loading, fraction collection and lipid extraction were carried out under subdued amber light or covered in aluminum foil when not possible. Exposure to oxygen and heat was minimized by keeping all samples covered and on ice.

Oocytes at each stage of maturation and embryos at different development points were removed from storage, allowed to thaw, and the one vol. of ice cold stabilizing buffer (5 mg/ml ascorbic acid, 5 mg/ml EDTA in PBS, pH 7.3) was added. Some oocyte and all embryo samples were used for identification of bilins and subsequent purification. These were sonicated maintaining the sample on ice using a VWR Branson Sonifer 450. The duty cycle was set to 40% and the output control was set to 4.5. The samples were sonicated 3× in 15 sec. intervals. Two vol. of extraction buffer (ethyl acetate/methyl acetate 8/1 plus 50 $\mu$g/ml butylated hydroxytoluene) were added to the sonicates. The samples then were placed on a rotator for 20 minutes in the cold room, centrifuged at 1000×g for 10 min. and the organic layer removed and stored on ice. The procedure was repeated and resultant organic layers were pooled. The samples were dried by exposure to a stream of nitrogen in the dark. The dried material was resuspended in 160 $\mu$l methanol an stored at −80° C.

Intracellular localization of bilins by isopycnic fractionation of homogenized *Xenopus laevis* stage VI eggs. Oocytes were homogenized, instead of undergoing sonication, and then fractionated in an isopycnic sucrose gradient as described below. For these experiments, approximately 250 stage VI eggs were used. These oocytes were treated identically as above but the initial stabilizing buffer was first decanted, new buffer added to a final volume of 1.2 ml and then homogenization was carried out manually and gently keeping samples on ice. A stepwise sucrose gradient was prepared with 1 ml layers composed of EDTA 30 mM, butylated OH toluene 0.5 mg/ml (5 $\mu$L/ml from a stock solution of 100 mg/ml in methanol), and sucrose in amounts enough for the fluid to reach the targeted specific gravity. The density of the layers were from the bottom to the top of the tube (in g/ml): 1.26, 1.24, 1.23, 1.22, 1.21, 1.20, 1.18, 1.16, 1.12, 1.08. The gradient was kept at 0° C. One milliliter of the homogenate was carefully loaded on top of the gradient without disturbing the layers. The preparation was spun with an SW40 rotor (Beckman) at 25,000 rpm, 0° C., for 22 hours. Afterwards, eight equal fractions of 1.375 ml were manually collected from the top of the gradient by means of a glass capillary tube and a peristaltic pump. Upon collection, the fractions were immediately blast frozen by submersion in liquid nitrogen and then stored at −80° C. for further processing. The bilins and retinoids in each gradient layer were extracted as described above.

Separation of Bilins and Retinoids by Chromatography. The bilins and retinoids in the oocyte and embryo extracts were separated using HPLC chromatography. Two different systems were used with the same Jupiter 5$\mu$ C 18 300A 250×4.6 column (Phenomenex). The first system used consisted of a Water Model 6000A solvent delivery system, Waters Model 440 absorbance reader, and a Waters automated gradient controller. A number of gradients profiles were used in this system. In all cases, the initial buffer (A) consisted of 10% acetonitrile, ammonium acetate 0.231 g/l, pH 6.5 while final concentration of buffer (B) was 100% acetonitrile. The time to arrive at 100% Buffer B was set to maximize the purification of the bilins and retinoids. Initially, the time was 60 minutes. Subsequently, to optimize isolation of the major bilin and retinoid species in the samples, another gradient profile was used consisting of from 10 to 28% in 12 minutes, then to 68% in 60 min and up to 100% in 62 min. The Waters Maxima 820 software was used to analyze the chromatogram. The samples injected first were vortexed for 1 min. and centrifuged at 1000×g for 2 min. The supernatant was injected into the HPLC. All-trans-retinol, all-trans-retinal, 13-cis-retinoic acid, 9-cis-retinoic acid, and all-trans-retinoic acid were obtained from Sigma. These standards were dissolved in methanol to a concentration of $3.3 \times 10^{-4}$ M. 25–100 $\mu$l of each standard solution was injected into the HPLC instrument. Fractions were collected at one min. intervals.

The second system, used to analyze the extracts from the sucrose gradient fractions, was an Alliance chromatography station (Waters) equipped with an automatic injector, in line vacuum pump, and a diode array detector. The data was collected and processed with a Millennium software (Millipore). Buffer A was composed of ammonium acetate 20 mM, pH 4.6. Buffer B was acetonitrile 100%. It was used for chromatographic separation of the bilins and retinoids obtained by the isopycnic sucrose gradient fractionation. Samples applied were dissolved in 240 $\mu$L of methanol. 100

μL of each solution were loaded to the column. The elution was carried out with the following gradient; 0 to 100% buffer B lineal increase in 45 min, 100% buffer B for 15 min, solvent flow 1 ml per minute, temperature 22° C. The eluate was monitored at 340 nm.

Storage and handling of bilins. The eluted fractions were collected in the dark by encasing the fraction collector in an aluminum foil covered box to prevent exposure to the light. The fractions were dried under a stream of nitrogen and stored at −80° C. After 25 individual fractions of the major bilin peak were collected and dried they were pooled in 3 ml of 100% ethanol. The material was stored as above in 40 μl aliquots. Before submitting samples for analyses, all were checked by rechromatography on HPLC to insure they had not broken down or isomerized.

Fraction analyses. Selected fractions were identified by their retention times corresponding to those of known standards. Unknown peaks were first analyzed on the basis of the absorption spectra using a Varian Cary UV/visible Spectrophotometer. The samples were scanned from 250 nm to 900 nm. Fractions were further analyzed by mass spectroscopy. Eight fractions of the major bilin peak were pooled and dried under nitrogen gas. The dried sample was prepared at a concentration of approximately 5 ng/μl using a buffer of 75:25 acetonitrile:water containing 1 nm ammonium acetate. Samples were analyzed in positive ion mode on the Finnigan LCQ ion trap mass spectrometer, using atmospheric pressure chemical ionization. The sample was also analyzed by IR.

UV Irradiation of pre-cleavage embryos. The effects of UV irradiation on the bilin content of *X. laevis* embryos were studied. Stage VI pigmented eggs were obtained and fertilized as described above. Immediately after fertilization the single-celled embryos were divided into two batches, control and exposed to a source of light emitting at 358 nm. The experimental embryos (approximately 200 per batch) were placed on top of a quartz base filled with 20% Steinberg buffer and exposed from below to 358 nm radiation for 10 min, prior to the first cleavage and all during 0.2 to 0.6 of the first cycle.

After UV irradiation, a set of embryos from each group were collected, dejellied with 2% L-cysteine, 0.16M NaOH and washed extensively in 20% Steinberg's buffer. The embryos then were transferred to a 15 mL test tube filled with stabilizing buffer (PBS, Ascorbic acid 5 mg/mL, EDTA 5 mg/mL, pH 7.3 0° C.) and allowed to settle. The remaining buffer was removed and new stabilizing buffer was added to a final volume of 2 mL. The bilins and retinoids in each batch were extracted, separated and analyzed as described. Another set of embryos were allowed to develop until stages 35–40. The gross morphological appearance of each individual embryo was evaluated by light microscopy. The developmental teratology characteristic of the "UV syndrome," was scored by standard criteria and categorized into the five groups comprising the "index of axis deficiency". Briefly, the published criteria used include a grade of [0] for normal morphology. Index of deficiencies I–V were assigned for [I] microcephalic with reduced size of eyes' [II] microcephalic with fused eyes or cyclopia with some retinal pigment visible; [III] extremely microcephalic, no or minimally visible retinal pigment, at least one optic vesicle present; [IV] acephalic but intact somites identified; [V] no neural or mesodermal structures present.

Results

Figure 2:
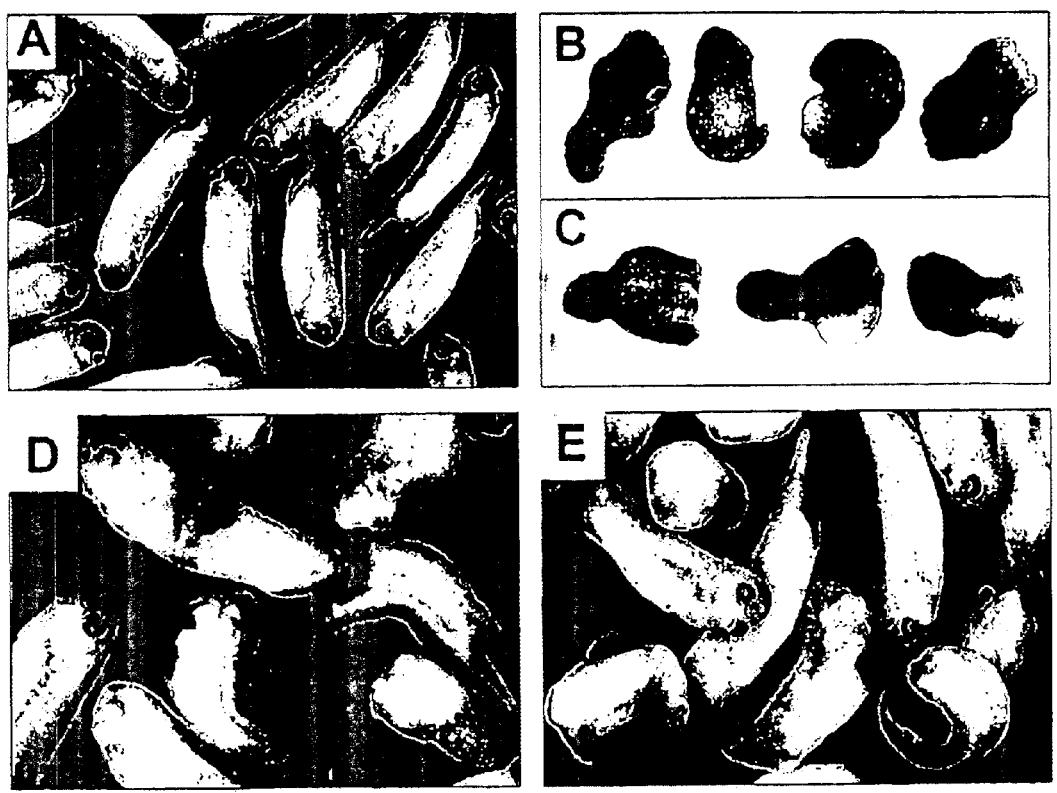
FIG. 2. Morphology of embryos irradiated with UV-light (A) Control embryos after reaching stage 30–35. (B) Adorsal embryos formed following exposure to 254 nm UV light. (C) Adorsal embryos formed following irradiation with 366 nm UV light. (D) Embryos irradiated with either long or short wavelength UV light following addition of frog-biliverdin IXα or (E) commercial biliverdin IXα.

On reaching stage 10.5, control embryos generate dorsal marker mRNAs, such as e.g. goosecoid and chordin, and ventral ones such as Vent 1 (FIG. 1). The presence of dorsal markers is associated with formation of dorsal organs. Thus, over 99% of stages 30–35 embryos form normal dorsal organs including head, body and tail structures with expected quantity and distribution of pigment characteristic of a DAI score of 5 (FIG. 2A). In contrast, the RNA of embryos irradiated with 254 nm UV light does not hybridize with either goosecoid or chordin cDNAs indicating their corresponding mRNAs are absent in these embryos. The absence of dorsal markers in 254 nm UV irradiated embryos is specific since it does not affect ventral markers, such as e.g. Vent 1, that can be detected by hybridization with its cDNA (FIG. 1). On reaching stage 35, most of these embryos lack of dorsal axis scored with a DAI of 0 (FIG. 2B). The rest reveal a full range of dorsal deficient DAI scores from 3–1 (FIG. 3A). From a total of 277 embryos exposed to 254 nm UV light during 5 different experiments, over 83% had scores below 3 with most scoring with a DAI of 0. The effects of irradiating with 366 nm UV light are identical in that their RNA also does not hybridize with either goosecoid or chordin but does with Vent 1 cDNAs (FIG. 1). These embryos also do not form dorsal axes. Their morphological appearance is identical to embryos irradiated with 254 nm UV light (FIGS. 2C, 3B). Of 805 embryos exposed to 366 mn UV light in 9 experiments, over 75% exhibited DAI of less than 2. In 4 of these separate irradiation experiments, nearly all embryos were scored with a DAI of 0.

Figure 4:
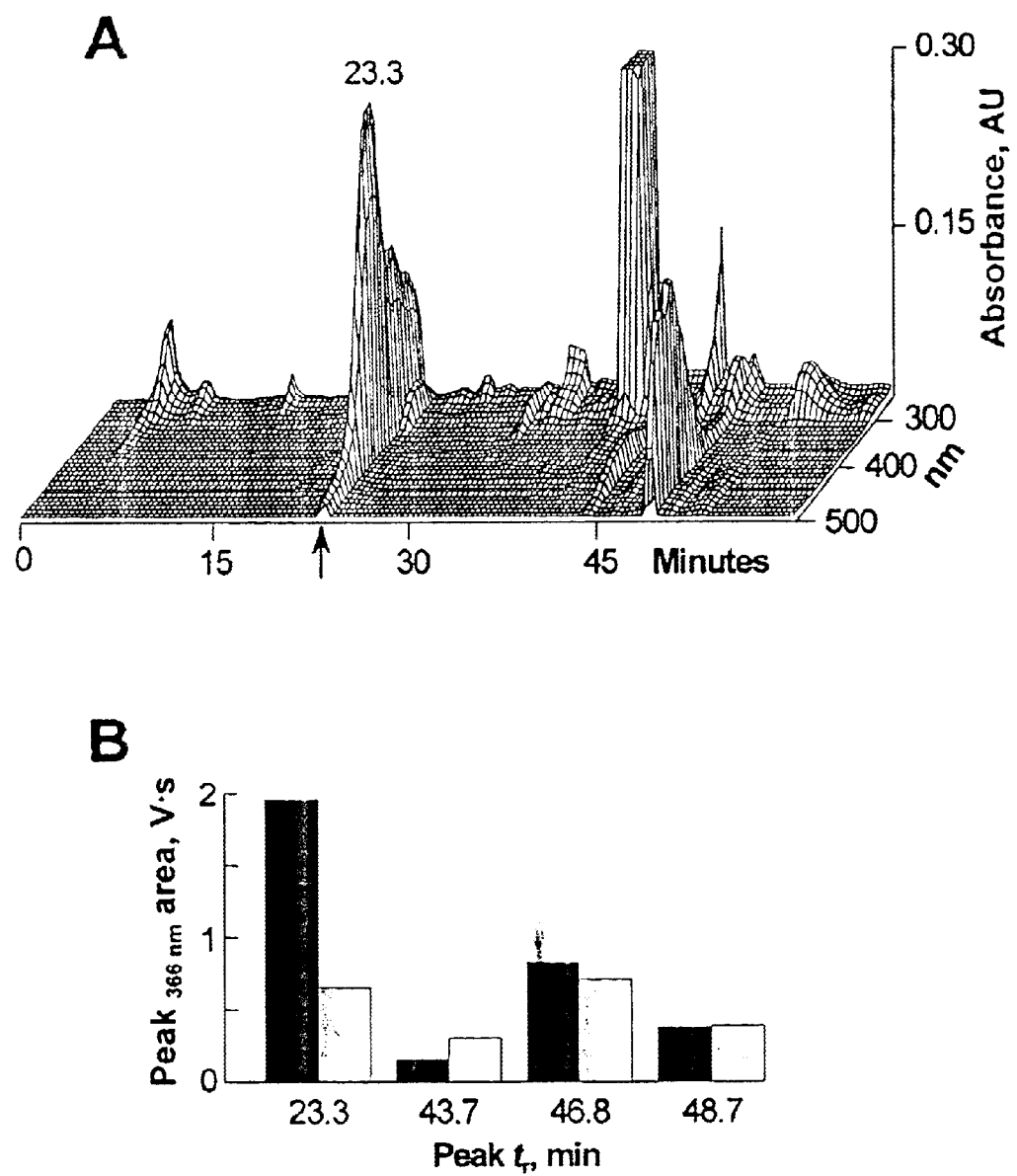
FIG. 4. HPLC elution profile of an extract of eggs or stage 1 embryos. (A) The chromatographic profile exhibits a number of peaks with distinctive characteristics. The peak pertinent to this report elutes with a retention time of 23.3 min (arrow). (B). Comparison of peak areas of the HPLC profiles of extracts from control (black) and of 366 nm UV light irradiated embryos (gray) demonstrate that the 23.3 min peak is the only one that is markedly reduced.
Figure 5:
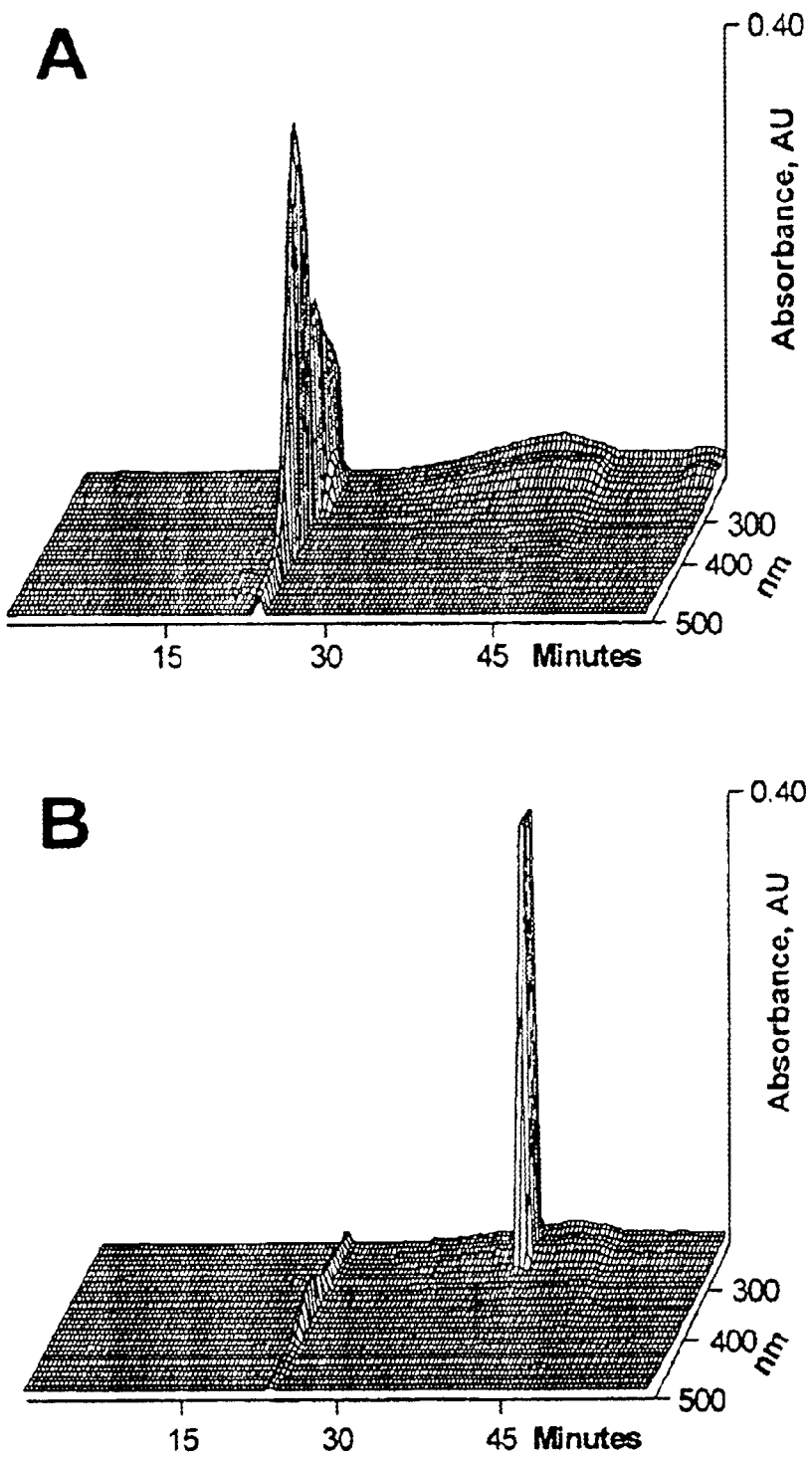
FIG. 5. Re-chromatography of purified 23.3 min fraction before and after UV light irradiation. (A) Before irradiation. (B) Chromatography of the same 23.3 min fraction after 366 nm UV light irradiation in vitro. The 23.3 min fraction is virtually abolished and a major new species is generated. The photo transformation product differs in its elution time (41.6 min) and spectral properties.
Figure 6:
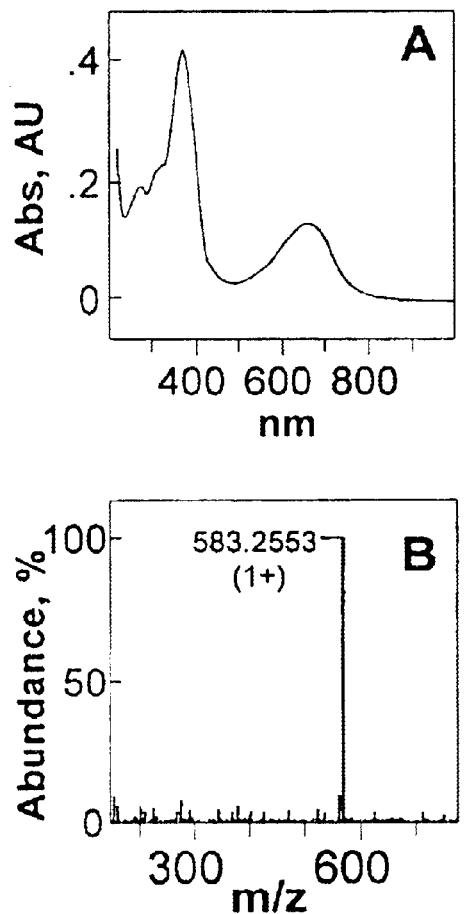
FIG. 6. Physical chemical features of the HPLC fraction 23.3 min identifies it as biliverdin IXα. (A) The 23.3 min HPLC fraction has a unique UV-Vis absorption spectrum with characteristic peaks at 375 and 665 nm in ethanol. (B) On mass spectroscopy positive ion mode analyses of the 23.3 min HPLC fraction yields a single high abundance peak with a mass-to-charge ratio of (1+) 583.2553. The molecule is predicted to have 19 double bond equivalents including all rings and carboxyl groups. There are five exchangeable protons ascertained by the mass increase in the presence of deuterium. These characteristics are identical to those of (1+) biliverdin. This identification was reinforced by the identical thin layer chromatography $R_f$ values (0.85 in a 3:1 chloroform: methanol mixture), co-chromatographic behavior of a commercial biliverdin sample and the yolk platelet material purified on $C_{18}$ with HPLC and by superposition of both absorption and NMR spectra (see FIG. 7). [C] shows the structure of biliverdin and the numbering scheme used for NMR analysis. Note that the one-letter designators for the pyrrolic rings are different from those used for porphyrins.
Figure 6:
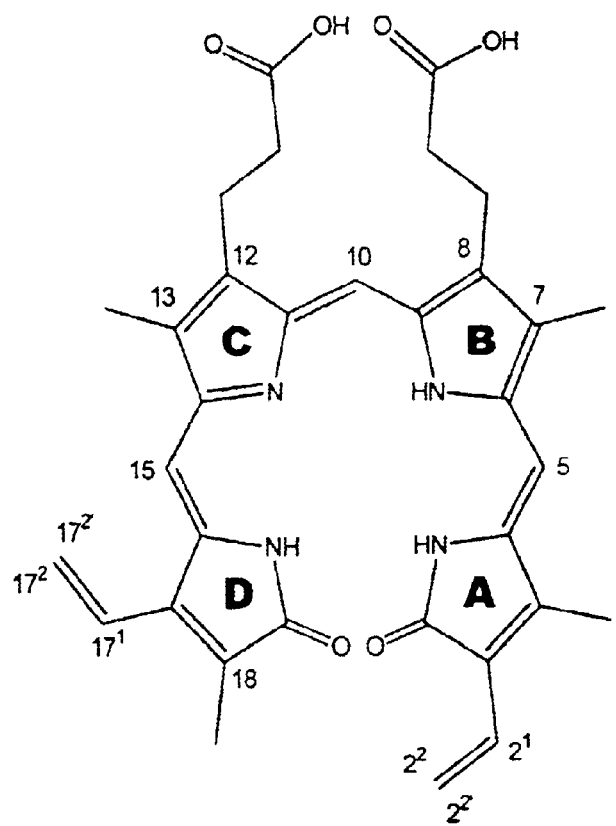
Figure 7:
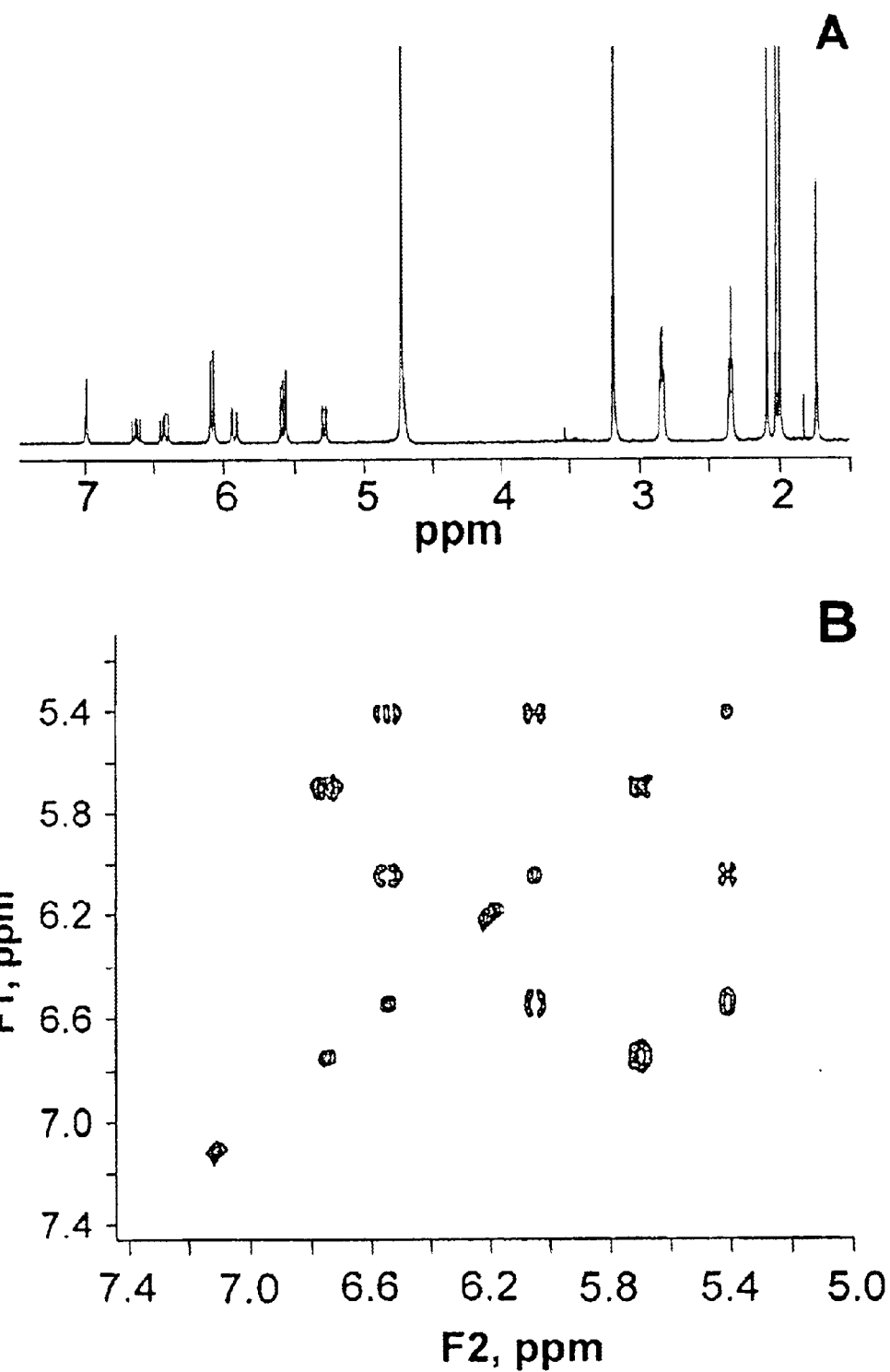
FIG. 7. NMR one-dimensional $^1H$ spectrum and TOCSY spectra of the HPLC fraction 23.3 min identified as biliverdin IXα. (A) The one dimensional $^1H$ spectrum of the pure 23.3 min HPLC fraction is identical to that of commercial biliverdin IXα. Chemical shifts are relative to trimethylsilyl propionate at 0.00 ppm. $^1H$ NMR (Methanol-$d_4$) δ 6.54(m, 1H,H-$2^1$), 5.41(d, 1H,H-$2^2$), 6.05(d, 1H,H-$2^{2'}$), 6.22(s, 1H,H-5), 7.11(s, 1H,H-10), 6.19(s, 1H,H-15), 6.75(m, 1H,H-$17^1$), 5.72(d, 1H,H-$17^2$), 5.68(m, 1H,H-$17^{2'}$), 2.47(t, 4H,H-$8^2$, H-$12^2$), 2.96(t, 4H,H-$8^1$, H-$12^1$), 2.09, 2.02, 2.00, 1.73(s, 12H,H -$3^1$, H$7^1$, H-$13^1$, H-$18^1$) $^{13}C$ NMR (Methanol-$d_4$) δ 173.3(C-1, C-19), 127.1(C-$2^1$), 119.9(C-$2^2$), 100.0(C-5, C-15), 117.1(C-10), 127.6(C-$17^1$), 123.1(C-$17^2$), 21.5(C-$8^1$, C-$12^1$), 38.2(C-$8^2$, C-$12^2$) 177.8(C-$8^3$, C-$12^3$), 139.5(C-8, C-12). (B) Plot of the vinyl region from TOCSY spectrum of the oocyte molecule. The chemical shifts and coupling patterns are identical to commercial biliverdin IXα. Additionally, the coupling between the carbonyl carbon and the α and β methylene protons of the propionic acid side chains were verified from the DEPT-HMQC, and HMBC spectra (data not shown).

The identical dorsal/ventral marker phenotypes and developmental outcomes of embryos irradiated with either short or long wavelength UV light suggested a common target molecule responsible for the ventralization. The molecule is extractable by organic solvents. The extracts separate in a $C_{18}$ HPLC column into a number of peaks that differ in their retention times and wavelength absorption characteristics (FIG. 4A). Comparing the chromatographic recordings of the extracts obtained from irradiated and control eggs/embryos demonstrates that the fraction that elutes at 23.3 min with 44% acetonitrile and exhibits an absorption peak at 375 nm is the only one that decreases significantly (FIG. 4B). In a typical experiment, over two thirds (67%) of the 23.3 min peak area is photo transformed by UV irradiation. The chromatographic behavior and spectral properties of the transformed peak differs from the parent compound in that it elutes later at 41.6 min, has lost the 375 nm peak and demonstrates a characteristic absorption peak at 278 nm (FIG. 5). Exposing the 23.3 min fraction to either 254 or 366 nm UV light in a cuvette also photo transforms it and reduces its absorption comparable to the in vivo observation. The material in that fraction is identified unambiguously as biliverdin IXα by UV-Vis, mass and NMR spectrometry (FIGS. 6 and 7).

Figure 3:
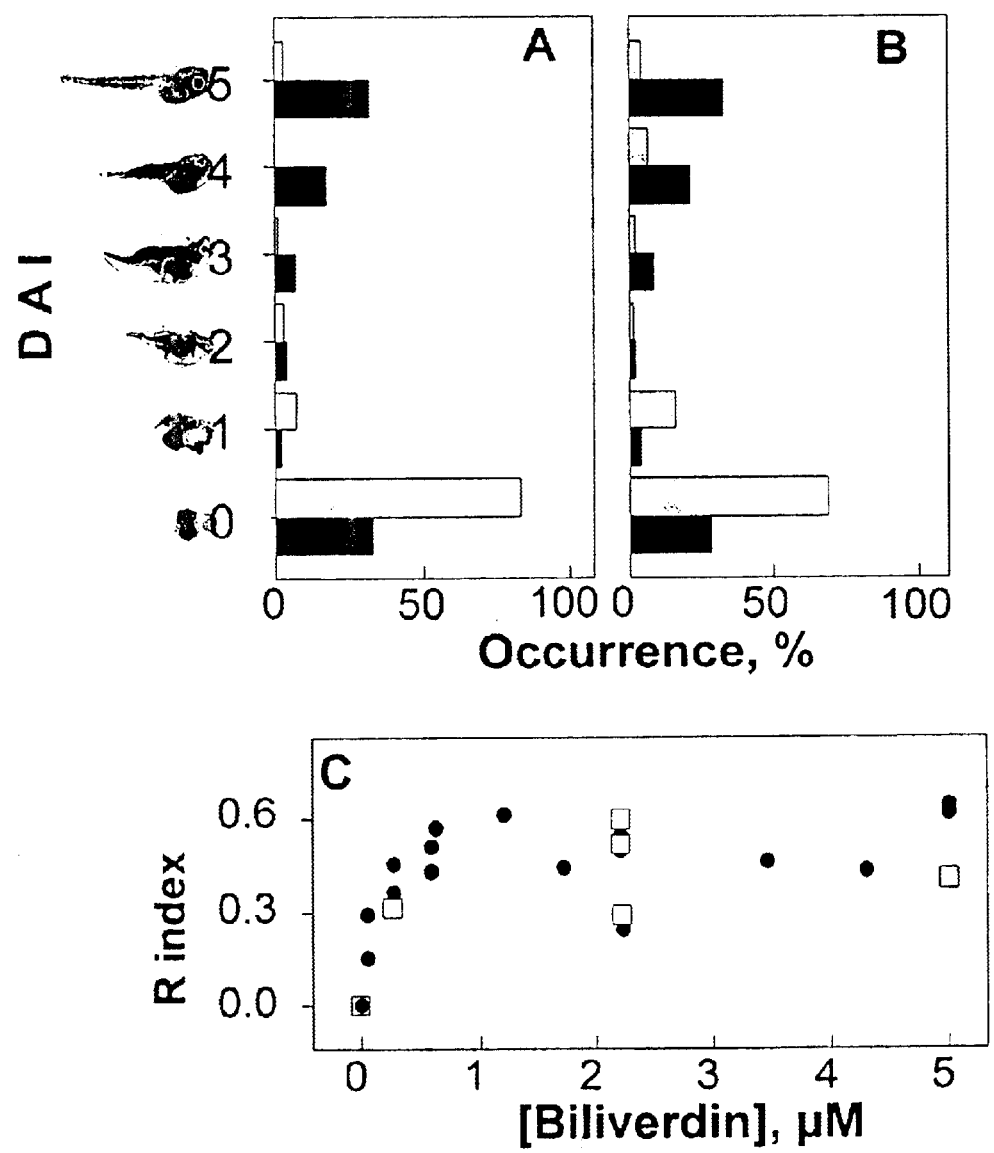
FIG. 3. Biliverdin IXα rescues UV-irradiated embryos from dorsal axis deficiency. (A). Average DAI score of embryos irradiated with 254 nm UV light [gray] is 0.35. About 51% of embryos treated with biliverdin [black] are scored with a DAI between 5–4 with an average DAI score of 2.72. (B). Average DAI score of embryos irradiated with 366 nm UV light [gray] is 0.72. Nearly 55 % of embryos incubated with biliverdin [black] recover and are scored with 4–5 with an average DAI of 3.08 for the total population. The recoveries are statistically significant (paired t with p<0.001). (C) The extent of embryo recovery from 254 nm [□] or 366 nm [●] UV light irradiation is dependent on biliverdin concentration. Recovery was determined with the equation $[R_i=(x-uv)/(c-uv)]$ where $R_i$=recovery index, x=average DAI for embryos incubated with biliverdin, uv=average DAI for embryos exposed to UV and c=average DAI for control embryos.

To demonstrate the correlation between biliverdin photo transformation and dorsal axis deficiency, the UV exposed embryos were incubated with the intact tetrapyrrole. The DAI score of the resultant embryos is shifted from the predominant adorsal, DAI=0 expected from irradiated embryos (FIGS. 2B, C), towards higher values closer to normal (FIGS. 2D, 3A, B). The rescued embryos demonstrate various degrees of dorsal axis development including fully developed head, eyes and tail structures. About 55% tadpoles develop with DAI scores of 5 or 4. Some of the embryos develop less completely exhibiting a range of DAI scores from 3 to 1. From 20 to 30% still do not develop dorsal structures at all and are scored with a DAI of 0. The degree of recovery of dorsal axis formation achieved by incubating embryos with commercially available biliverdin is comparable (FIG. 2E). This effect of biliverdin pertains to embryos irradiated with either 254 or 366 nm UV light (FIG. 3). It is concentration dependent since greater amount leads to greater degrees of recovery with a plateau of recovery is reached at 1.2 µM biliverdin (FIG. 3C). In contrast, there is no recovery with 2.2 µM photo transformed biliverdin or 3.7 µM biliverdin dimethyl ester hydrochloride (not shown). The time during development when biliverdin rescues irradiated embryos is maximal during the period encompassed by the first cleavage (normalized time, fertilization-first mitosis $T_{fm}=1$). The effectiveness decreases rapidly by $T_{fm}=1.75$ and disappears by 3.

Intact biliverdin, photo transformed or dimethyl ester are not dysmorphogens. When control fertilized oocytes unexposed to UV light are incubated with any of these compounds they develop normally with an average DAI of 5. The intact IXα isoform and at least one of the carboxyl groups of its propionic side chains contribute to its biological activity since photo transformed biliverdin or dimethyl ester biliverdin do not induce irradiated embryos to form dorsal structures.

The restoration of the capability of irradiated embryos to form a normal dorsal axis by addition of biliverdin together with the absence of multiple ectopic axes (FIGS. 2D, 2E) suggests that while both 254- and 366 nm UV light affects the biliverdin in the cytoplasmic yolk platelet, neither affect the localization of the cortical determinant to the future dorsal zone. A single normal dorsal axis in biliverdin-rescued embryos can only take place if the cortical determinant is properly localized to the dorso-vegetal zone. Currently, it is believed that the cortical factor attains its ultimate position by means of rotation of the cortex dependent on microtubules. It has also been proposed that 254 nm UV light inhibits this microtubule-driven rotation and, consequently, leads to dorsal axis deficiency. However, the identical adorsal teratology produced by either 254 or 366 nm UV irradiation together with the rescue of dorsal axes by biliverdin, suggest that the UV light perturbation of cortical rotation may be more complex, perhaps differ from the current model, and call for revisiting the subject experimentally.

Figure 8:
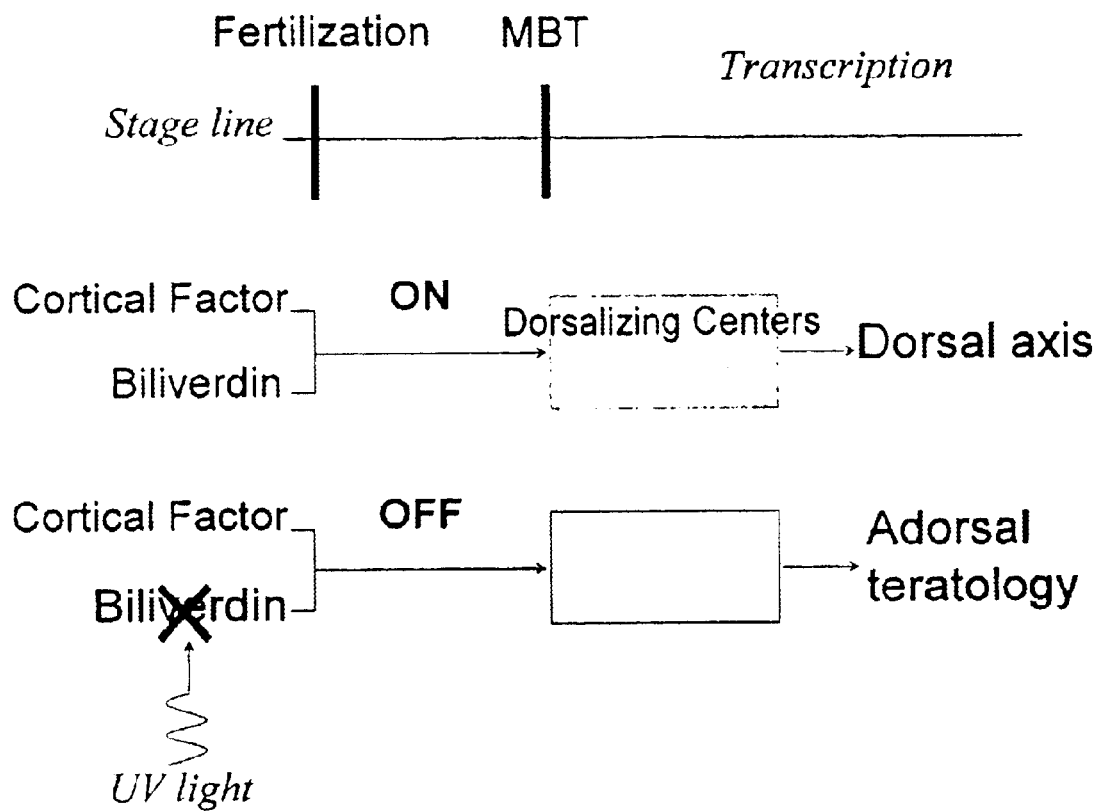
FIG. 8. Molecular switch for induction of dorsal axis. Biliverdin is proposed to interact with a cortical factor to trigger or switch-on the downstream activation of genes. When the chemical switch is turned ON, the Nieuwkoop center and the Spemann-Mangold organizer are sequentially formed. The UV irradiation of biliverdin renders an ineffective photo-product, the chemical switch remains OFF and the dorsalizing gene products that participate in the configuration of the dorsal axis are not formed. The result is adorsal teratology.

Following sperm entry, the yolk platelets are concentrated to the entire vegetal hemisphere of the fertilized eggs. Biliverdin may be released from the organelles to interact with the cortical factor (FIG. 8). The biliverdin-cortical factor complex, localized to the future dorso-vegetal zone, can act as a switch-ON mode to initiate a cascade of events that establish the Nieuwkoop center and the Spemann-Mangold organizer. The dorsalizing signals that are synthesized and/or activated following mid blastula transition (MBT) determine the configuration of the dorsal axis and inhibit the activity of other ventralizing signals. Photo transformation of biliverdin by UV light generates an ineffective product. Therefore, the chemical switch remains OFF, the Nieuwkoop center and the Spemann-Mangold organizer are not formed and dorsalizing signals such as the gene products goosecoid and chordin (FIG. 1) as well as many others, e.g. xSOX3 and siamois, are absent or reduced. Concurrently, the ventral signals act unrestrained. The result is an adorsal embryo.

Mass spectrometric analysis yields a molecular weight of (1+) 583.2553 (FIG. 6b). The predicted (1+) composition is $C_{33}H_{35}N_4O_6$ with 19 double bond equivalents and 5 replaceable protons based on MS analysis in the presence of d-methanol.

NMR analysis of the DCD are summarized in Table 1 which reports the 1H chemical shifts for billiverdin-IX-alpha. All assignments refer to the numbering scheme shown in FIG. 6C. Assignments were made according to the method of (Marko, H., Muller, N., and Falk, H. (1990) Eur. J. Biochem. 193, 573–580), and by comparison to commercially available billiverdin-alpha (Sigma-Aldrich). No attempt was made to distinguish between methyl group and NH resonances.

TABLE 1

Assignments of billiverdin proton signals in methanol-d4. Chemical shifts are relative to trimethylsilylpropionate at 0.00 ppm.

| Position | Chemical shift(ppm) |
|---|---|
| $H-2^1$ | 6.54 |
| $H-2^2$ | 5.41 |
| $H-2^{2'}$ | 6.05 |
| $H-5$ | 6.22 |
| $H-10$ | 7.11 |
| $H-15$ | 6.19 |
| $H-17^1$ | 6.75 |
| $H-17^2$ | 5.73 |
| $H-17^{2'}$ | 5.68 |
| CH3 | 2.09, 2.02, 2.00, 1.73 |

The DCD material was identified as billiverdin-IX-alpha based on NMR and mass spectral data.

Commercially available biliverdin matches the dorsalizing activity of the isolated material. Thus, commercial biliverdin rescues embryos exposed to UV light from the expected dorsal axis deficiency. The spectrum of rescue is comparable to that obtained with oocyte-derived biliverdin.

The elution profile observed when extracts from embryos are chromatographed are quantitatively similar to that of oocytes. The total peak area of biliverdine, however, undergoes changes during each embryonic milestone. During the first 4 hours of embryogenesis, it decreases progressively until 60% of the material has disappeared. In early blastula stage, the fraction is repleted to the point that it returns to a level equal to or exceeding that of state VI oocytes. This is associated with a decrease of those peaks corresponding to carotenes. Over the next 90 hours, the period of organogenesis, the amount of the material decreases once again until it eventually disappears.

When compared with the above quantitative changes in biliverdine, the variation in the total amount of each of the retinoids is minor during embryogenesis. This observation is similar to that noted during oogenesis.

The adult frog liver, lung, and muscle contain a number of retinoids and precursors but do not contain biliverdine. The only adult tissue where this bilin is found is the ovary. Similar findings were obtained with oocyte extracts from albino frogs. Hence, the absence of pigment in the albino frogs did not result in differences in terms of the quantities and presences of biliverdine.

Distribution in Isopycnic Sucrose Gradient. An oocyte homogenate separates on a standard sucrose gradient (1.08–1.24 g/ml) into fractions containing known components (81–83). The cytosol, ribonucleoprotein particles, and small endocytosed vesicles collect at densities between 1.08 to 1.12 g/ml while the multivesicular bodies collect at densities between 1.14 and 1.16 g/ml. The most predominant intracellular organelles are the yolk platelets, constituents that layer at densities of 1.20 to 1.24 g/ml. In general, light yolk platelets are found in the upper zones (1.20 g/ml) and heavier platelets in the lower zone (1.24 g/ml). The densest particles that centrifuge to the bottom of the gradient are the nuclei. The 8 fractions derived from oocyte homogenates fractionated by sucrose gradient centrifugation exhibit different physical characteristics. Fraction 1 was a whitish lipid-containing layer. Fractions 2 and 3 were clear, fraction 4 had a yellow band, fraction 5 was also clear, fractions 6 and 7 had the light beige color of platelets, and fraction 8 contained greenish pigment. The peaks comprising the entire bilin/retinoid profiles generated on chromatography of the homogenate extracts are recovered but now are distributed within the individual fractions of the sucrose gradient. The upper layers of lightest sucrose densities (layers 1–4) contain mostly a single compound that elutes at 33 min. Biliverdine is not cystosolic but rather is entirely distributed in fractions 6, 7 and 8, co-sediment with oocyte vesicles and/or organelles including the light and heavy yolk platelets and nuclei. The relative abundance of this compound is highest in the light yolk platelet region.

TABLE I

Distribution of Biliverdine in Sucrose Gradient Fractions

| FRACTION | OOCYTE CONSTITUENT | Biliverdine |
|---|---|---|
| 1 | LIPIDS | Not Present |
| 2 | CYTOSOL | Not Present |
| 3 | CYTOSOL | Not Present |
| 4 | ENDOCYTOSED VESICLES | Not Present |
| 5 | MULTI VESICULAR BODIES AND MITOCHONDRIA | Not Present |
| 6 | LIGHT YOLK PLATELETS | +++ |
| 7 | HEAVY YOLK PLATELETS | ++ |
| 8 | NUCLEI | + |

Exposure of Embryos to Ultraviolet Light. The data establish that biliverdine is contained within oocyte nuclei, vesicles, granule, and/or yolk platelets. This provided us with the opportunity to examine whether destroying or altering the molecular structure of the bilin would affect embryogenesis. The platelets (and other granules) settle to the ventral hemisphere following fertilization and rotation. Exposure of the ventral surface of the pre-cleavage embryos to UV light is know to induce teratogenesis. To determine if there is a relationship between UV light exposure, biliverdine content in the ventral surface of the embryo, and subsequent teratology, we tested whether this irradiation affected biliverdine content of the exposed embryo.

The retinoid/bilin fractions eluting from the extracts of UV exposed embryos were compared to that of control embryos. Only one compound was found to decrease after UV irradiation, namely biliverdine; its content decreased by 50%. The only other change eluted at 43 min. In contrast, its peak area is increased. The relationship between these two fractions is to be determined. All other peaks were unchanged.

TABLE II

Effect of Ultraviolet Irradiation on Embryo Teratology

| Group | Total | Dead | Alive | Normal | Teratology |
|---|---|---|---|---|---|
| Control | | | | | |
| n | 203 | 10 | 193 | 192 | 1 |
| (%) | (100) | (5) | (100) | (99.5) | (0.5) |
| UV | | | | | |
| n | 190 | 13 | 177 | 80 | 97 |
| (%) | (100) | (7) | (100) | (45) | (55) |

Of 203 control embryos, about 5% died within the first hour post-fertilization. Over 99% of the embryos developed normally; only 1/203 control embryos (0.5%) demonstrated teratology (Table II). In that case, the teratology was scored with an index of axis deficiency of [1], consistent with the expected. In contrast, 97/190 of the UV irradiated embryos (55%) manifested the "UV syndrome" with the majority developing with index of axis deficiency of [4] or [5]. In the irradiated group, the number of embryos that died in the first cell cycle was less than 7%, only slightly higher than the control group.

EXAMPLE II

Effects of the Compounds of the Present Invention on Neoplastic and Normal Cells Biliverdine was the first differeguline isolated from a living cell. It was isolated from *Xenopus laevis* oocytes and characterized as the most predominant differentiation signal in this animal. Unexpectedly, this frog oocyte compound induced terminal differentiation of a human cancer cell, HT29 colon cancer line. Therefore, biliverdine may be effective as a novel agent useful for cancer therapy. The present example, therefore, relates to 1) the purification and characterization of the physical chemical and functional properties of biliverdine from *Xenopus laevis* oocytes and embryos, 2) the demonstration that the biliverdine induces terminal differentiation of human colon cancer cells and can be used as an agent for the treatment of cancer, and 3) adaptations of its chemical synthesis to provide large quantities of the any of the family of bilins that may induce commitment and differentiation of embryo, stem and other undifferentiated cells.

The biological effectiveness of biliverdin in driving the differentiation process forward applies to the known differentiation pathology characteristic of neoplastic adult cells. Thus, biliverdine arrests the proliferation of HT29 human colon cancer cells within 72 hours and causes overproduction of differentiation markers, such as CEA and alkaline phosphatase. The proliferative arrest extends beyond the period of exposure to the compound. Proliferation does resume 12 days later but it occurs at a slower rate (2–3 fold less) than that of control, untreated cancer cells.

The process of differentiation is fundamental to all biological organisms. It takes place at all stages of development from the embryo to the adult, The embryo is the product of a single cell, the egg, that is fertilized by a single sperm. The resultant embryonic cell then undergoes a series of divisions that produce many daughter cells with distinct and powerful properties. These cells are the primordial germ lines that are committed to form the three distinct categories of tissues ectodermal, mesodermal and endodermal. The differentiation of these germ lines results in the establishment of multiple tissues that organize into organs. The adult preserves some precursor, undifferentiated cells that retain the capability to form committed stem cells that terminally differentiate. These cells serve to replenish the ones that have undergone the normal aging process and died, for example in bone marrow, gonads, bowel, skin cells, and others. Periodically, therefore, these precursor cells initiate the normal process of ordered change from a primitive to a mature cell through progressive differentiation that results in the formation of a terminally differentiated white blood cell, brush border intestinal cell, etc.

The normal differentiation process of these cells can be altered for diverse reasons during carcinogenesis. Thus, exposure to radiation, chemical carcinogens, viral infections, etc., can interrupt and block the differentiation events resulting in the accumulation of partially differentiated cancer cells, as for example, in leukemia. The pathology can be localized to any level in the differentiation process resulting in histological and biochemical phenotypes characteristic of that stage.

Reversal of the pathology described above is a feasible objective encompassed by the term cancer differentiation therapy and reviewed in 1986. The neoplastic phenotype is usually stable within an adult animal. For example, mouse teratocarcinoma, cells implanted into adult mice will maintain their malignant phenotype for hundreds of passages. However, exposure of these, and other, cancer cells to particular chemical environments, such as those found in the early embryo, can reverse the neoplastic process. Thus, when teratocarcinoma cells from a black mouse are injected into the blastula of a white mouse, a chimeric animal is formed that is composed of normal black and white cells. The same teratocarcinoma cells, as well as acute promyelocytic leukemia cells, can be induced to terminally differentiate by all-trans retinoic acid. Similarly, erythroleukemias and other forms of leukemia cells, neuroblastoma cells, mammary cancer cells and rhabdomyosarcoma cells have been shown to differentiate by exposure to chemicals such as hexamethylenebisacetamide, dimethyl sulfoxide, retinyl methyl ether, and N,N-dimethylformamide. Metastases to the lung of embryonal carcinoma have differentiated into mature teratomas following cytotoxic chemotherapy. More recently, liposarcoma, colon, and breast cancer cells were found to terminally differentiate when exposed to troglitazone (liposarcoma, colon and breast cancers) or butyric acid (colon cancer cells).

The above considerations make it apparent that the reversal of pathological conditions of differentiation that result in a progression of a cancer cell to a fully differentiated benign state is a major challenge whose achievement will be clearly aided by understanding the molecular processes that regulate as well as those that interrupt or alter differentiation itself.

Molecular messages and specific gene products are thought to participate in the differentiation processes in both the embryo and adult many of the pertinent molecules and genes have been identified. These include molecules believed to be components of the classical "organizer" or to be directed by them, such as Vg1, activin, Wnt, Lim1, Gsc, Xnot HNF3, chordin, noggin, follistatin, as well as Hox, Kr, Krox20, scratch, castor, spalt, cKr2, zic, etc. However, most of these molecules are not available in sufficient quantities, if at all, to test their capability to induce terminal differentiation of cancer cells. Moreover, many of these molecules are themselves products of other pleiotropic, master signals such as the retinoids and other hormone ligands of the nuclear receptor superfamily of proteins. Therefore, these master switch molecules, differegulines, are the ones that act at the earliest, decisive steps in differentiation and are most likely to act on cancer cells to drive their differentiation forward. If these master chemical signals did exhibit such properties with neoplastic cells and could be obtained in large quantities, they could serve as agents useful in the area of cancer treatment.

Biliverdin causes human colon adenocarcinoma to accumulate $p21^{(Cip1)}$ and $p27^{(Kip1)}$, increase the number of cells in $G_1$ and arrest their proliferation when incubating the cells with biliverdin. Subsequently, the contents of the differentiation markers, alkaline phosphatase, carcinoembryonic antigen and triacyl glycerol, are markedly increased. The dimethyl biliverdin ester is inactive indicating the propionic side chains are essential for the effects. The inhibitory effect on proliferation also applies to human liposarcoma, thyroid carcinoma cells and two mouse lymphomas. Concurrently, triacyl glycerol is upregulated in liposarcoma cells and 3T3 fibroblasts. The proliferative arrests are reversed when biliverdin is removed.

The translation of in vitro observations to in vivo conditions is greatly facilitated by a number of animal models that are currently in use to evaluate the efficacy of agents in the treatment of cancer. Some use animals that are immunodeficient (athymic) and others, ones with a fully functional immune system. The former allows for xenogeneic and syngeneic tumors to be grown and tested while the latter are best for syngeneic tumors grown under conditions where the animal's immunological system participates in the response to therapy. Since the issue of pertinence here is the capability of biliverdine and its derivatives to induce terminal differentiation of human tumors of various origins, the initial model of choice would be the athymic mouse model for which there is experience in growing tumors as either primary subcutaneous tumors or as metastatic models. In the former case, the HT29 human colon cancer cell line has been used extensively while for the latter there are now several established models with other human colon and prostate cancer cells. These can be tested with biliverdine for responsiveness to terminal differentiation in vivo.

In addition to those described above, the following experimental protocols were followed.

Cell Culture Conditions. Human HT 29 colon cancer cells were purchased from the American Type Culture Collection. Cells were maintained in Dulbecco's Modified Eagle's Medium (DME) supplemented with 5% heat-inactivated fetal bovine serum, 2 mM glutamine, and antibiotics (DME/5%). All cell lines were incubated in a humidified 5% $CO_2$/air environment. They were maintained at 37° C. in 5% $CO_2$ covered in aluminum foil to prevent exposure to the light. A total of $1\times10^6$ cells were incubated per flask and allowed to attach overnight. Media was changed every third day. Cell counts were performed on a Coulter Counter following detachment of cells by standard trypsinization procedures. Only those preparation exhibiting cell viability greater than 95% were used. The cells were incubated with 0.4 $\mu$M biliverdine, a concentration that did not induce apoptosis but arrested cell proliferation, as described below. The period of exposure was followed by incubation in the absence of biliverdine. Cell numbers were monitored until proliferation resumed. The production of CEA and alkaline phosphatase was measured as described below.

Expression of differentiation markers. Carcinoembryogenic antigen in cell supernatants collected each three days was assayed by standard ELISA determinations using an $IM_X$ assay for quantitative measurement of the antigen. Cellular triacyl glycerol content was measured spectrophotometrically by enzymatic hydrolysis and analysis of the amount of glycerol released using a standard assay, Triglyceride (INT) 10 (Sigma Diagnostics). Cellular alkaline phosphatase activity was determined by measuring the fluorescence change induced by the hydrolysis of 4-methylumbelliferylphosphate. The fluorescence is detected at 450 nm with an excitation of 365 nm, using a Jobin Ivon-Spex Fluoro Max-2 fluorimeter. The alkaline phosphatase activity detected was expressed in units of $\mu$mol/mg protein/min.

The HT29 colon cancer cells were incubated with different concentrations of biliverdine and their response studied to identify the concentration ranges required to elicit a biological and/or a toxicological response (Table III).

TABLE III

Effects of Biliverdine on Cellular Proliferation and Viability.

| Concentration, $\mu M$ | Effect |
|---|---|
| 0.01 | None |
| 0.1 | Proliferative Arrest |
| 0.30 | Proliferative Arrest |
| 0.40 | Proliferative Arrest |
| 1.00 | Apoptosis |

The effects of biliverdine on cell proliferation and production of two differentiation markers, CEA and alkaline phosphatase activity, were analyzed, CEA was assayed by standard ELISA determinations while alkaline phosphatase activity was determined by measuring the fluorescence change induced by the hydrolysis of phosphate from 4-methylumbelliferylphosphate as follows. To measure CEA production, cell supernatants were collected at the first cycle of change of media (third day) and on day 12. Cell counts were obtained. The supernatant was dried under vacuum using a Savant Speed Vac Plus. The residue was resuspended in 400 $\mu l$ Milli-Q water. This was diluted 1:1 and assayed for CEA using an Imx assay for quantitive measurement of the antigen. The kit reagents were added to the sample and incubated to bind the CEA to anti-CEA coated micro particles. An aliquot was transferred to a glass matrix that binds the micro particles irreversibly. After washing, anti-CEA conjugated to alkaline phosphatase was added forming an additional complex to the CEA present in the reaction mixture. Following washing, the alkaline phosphatase substrate, 4-methylumbelliferyl phosphate, was added and the resultant fluorescence was read by a Micro particle Enzyme optical assembly.

Alkaline phosphatase activity was assayed at the same periods as above but with different sets of cells. Treated and control cells were detached with trypsin and counted. One half of the cells were used to maintain the culture while the other half were used to measure alkaline phosphatase activity. The cells were trypsinized and washed with phosphate buffered saline three times and lysed in 200 $\mu l$ of Milli-Q water. Ten $\mu l$ of the cell lysate were taken for determination of protein concentration using a Bio-Rad Protein Assay Kit (Bio-Rad). The aliquot was added to 800 and 190 $\mu l$ of Milli-Q water and Coomassie blue dye, respectively. Absorbance was detected at 595 mm on a Varian Cary UV-Visible Spectrophotometer. The absorbance was compared against a standard curve created with bovine serum albumin from 2.5 to 25 $\mu g/ml$. Two hundred $\mu l$ of incubation buffer containing the alkaline phosphatase substrate, 4-methylumbelliferyl phosphate in diethanolamine, 0.5 M, pH 10.4, was added to the remaining cell lysate. The mixture was incubated at 37° C. for 4 hrs after which 5.5 ml of ice cold amino-methyl propanol (AMP) buffer, pH 12, was added. The fluorescence generated is detected at 450 nm with an excitation of 365 nm, using a Jobin Ivon-Spex Fluoro Max-2 fluorimeter. The calibration curve was be generated from 0.05 to 50 $\mu M$. The alkaline phosphatase actively detected was expressed in units of $\mu mol$ product/mg protein/min.

HT 29 Colon Carcinoma

Biliverdin IXα exerts powerful effects on human colon cancer HT 29 cells. Normally, the contents of p21 and p27, known inhibitors of the CDK system, increase as control HT 29 cells become confluent and reach stationary phase. However, when these cells are incubated at a lower density in fresh culture medium, their p21 and p27 contents become nearly undetectable, CDK system is activated, Rb protein is phosphorylated and they resume cycling in log phase proliferation. In contrast, addition of $4 \times 10^{-7}$ M biliverdin to the incubation medium of the low-density cultures, results in persistence and/or progressive increase in p21 and p27 content starting as early as 16 hs. This effect on p21 induction is dependent on one or both of the propionic acid side chains of biliverdin. When the dimethyl ester biliverdin analog, with its blocked propionic acid side chains, is used, p21 becomes nearly undetectable, identical to that of a control culture that has entered log phase. The effects of biliverdin on p21 and p27 content in HT 29 colon cancer cells is summarized in the tables below.

TABLE IV

The effects of biliverdin on p 21 content in HT 29 Colon Cancer Cells

| Treatment | 0 | 16 | 30 | 40 |
|---|---|---|---|---|
| No Biliverdin | +++ | ++ | + | ND |
| (+) Biliverdin | +++ | +++ | +++ | ++++ |

TABLE V

The effects of biliverdin on p 27 content in HT 29 Colon Cancer Cells

| Treatment | 0 | 16 | 30 | 40 |
|---|---|---|---|---|
| No Biliverdin | +++ | ++ | + | ND |
| (+) Biliverdin | +++ | +++ | +++ | ++++ |

The presence of the CDK-inhibitors leads to under phosphorylation of Rb protein. As a consequence, the cells are removed from cycling and the number of cells in $G_1$ increases while those in S and $G_2$ decrease, compared with control, untreated ones. This response of cell cycle kinetics is quite similar to those reported for other agents known to cause a $G_1$, block e.g. troglitazone. Ultimately, proliferation ceases within one to three days. During the next 35 days, they resume division but at a very reduced rate exhibiting a doubling every 103 hours. This decreased rate persists even after the tetrapyrrole is no longer added to the incubation medium. Finally, twelve days after its removal, proliferation resumes at a brisker rate dividing every 41 hrs. This rate is still slower than that of the control cells that double every 18 hrs. Ten-fold higher amounts than the optimal biliverdin concentration, for example 5 $\mu M$, also arrests proliferation though there is an associated decrease cell numbers in the first three days. In contrast, cellular survival or proliferation is not affected by amounts lower than $10^{-7}$ M biliverdin (not shown).

Figure 9:
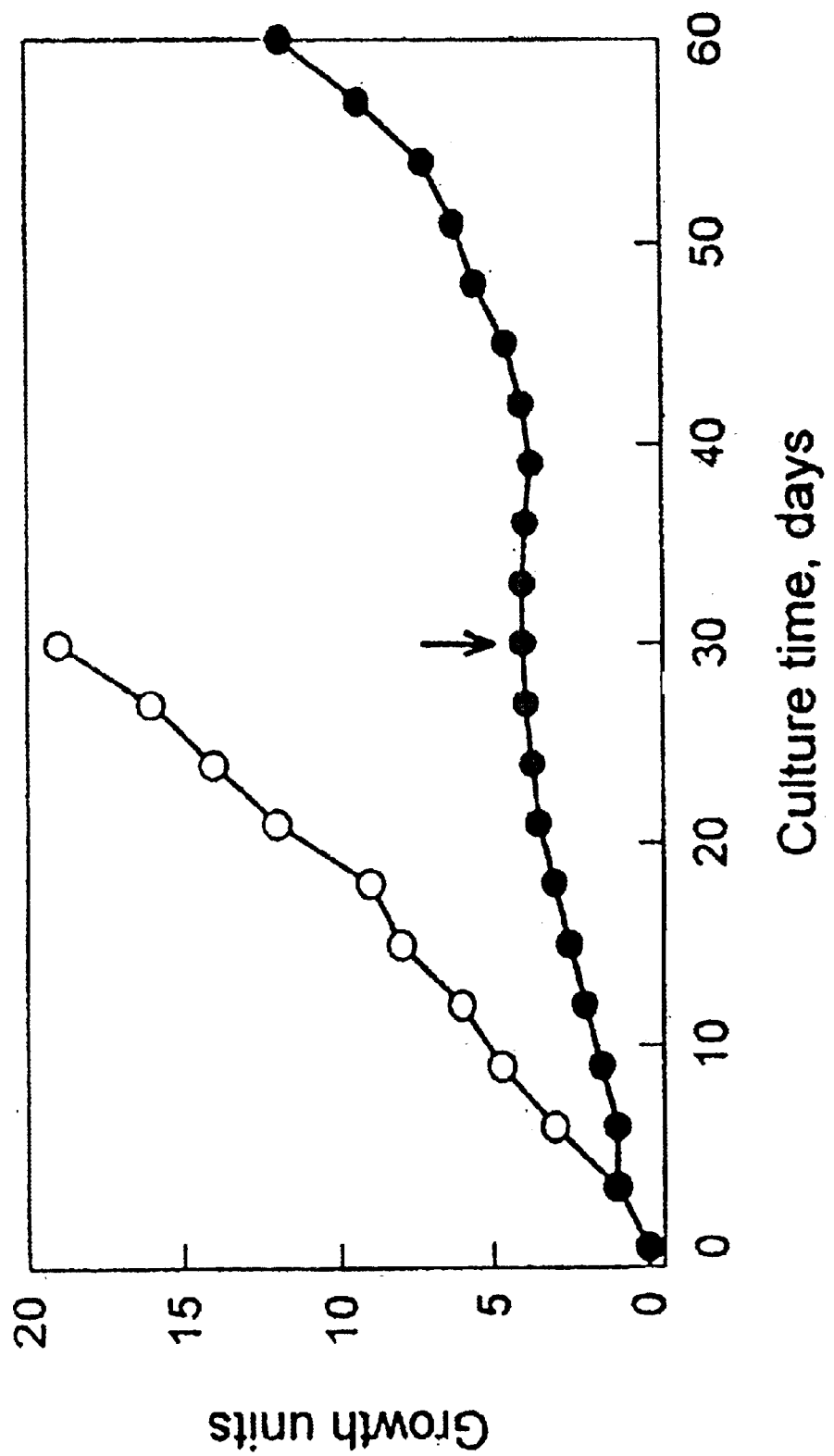
FIG. 9. Biliverdin arrests proliferation of HT29 colon cancer cells. Control HT29 cells incubated without biliverdin (○). Within 1 day of exposure to biliverdin, proliferation is arrested (●). On day 30, treatment is discontinued. Twelve days later, proliferation resumes at a rate that is 43% of that of the control. The effects on proliferation by biliverdin purified from frog eggs are identical to those obtained with a commercial biliverdin preparation. Therefore, biliverdin is the active species in the egg preparation and not an undetected contaminant.

At concentrations of 1 $\mu M$ and above, biliverdine causes apoptosis while below 0.1 $\mu M$ it has no effect on either survival or proliferation. Cells incubated with concentrations between 0.1 and 0.4 $\mu M$ exhibit a proliferative arrest within the first 72 hours followed by a nearly complete inhibition of cell division (FIG. 9). The marked reduction in proliferation persists throughout exposure to the compound and for about 12 days after release of exposure. Only then does brisk proliferation resume, but at a rate that is much slower than that of control, untreated cells. Thus, control cells have a doubling rate of about 18 hrs, i.e., in a three-day period the number of cells increases about 15 times. The treated and released cells divide every 41 hrs, i.e., in a three-day period their number increases only 3.4 times, a five-fold reduction compared to the controls.

Figure 11:
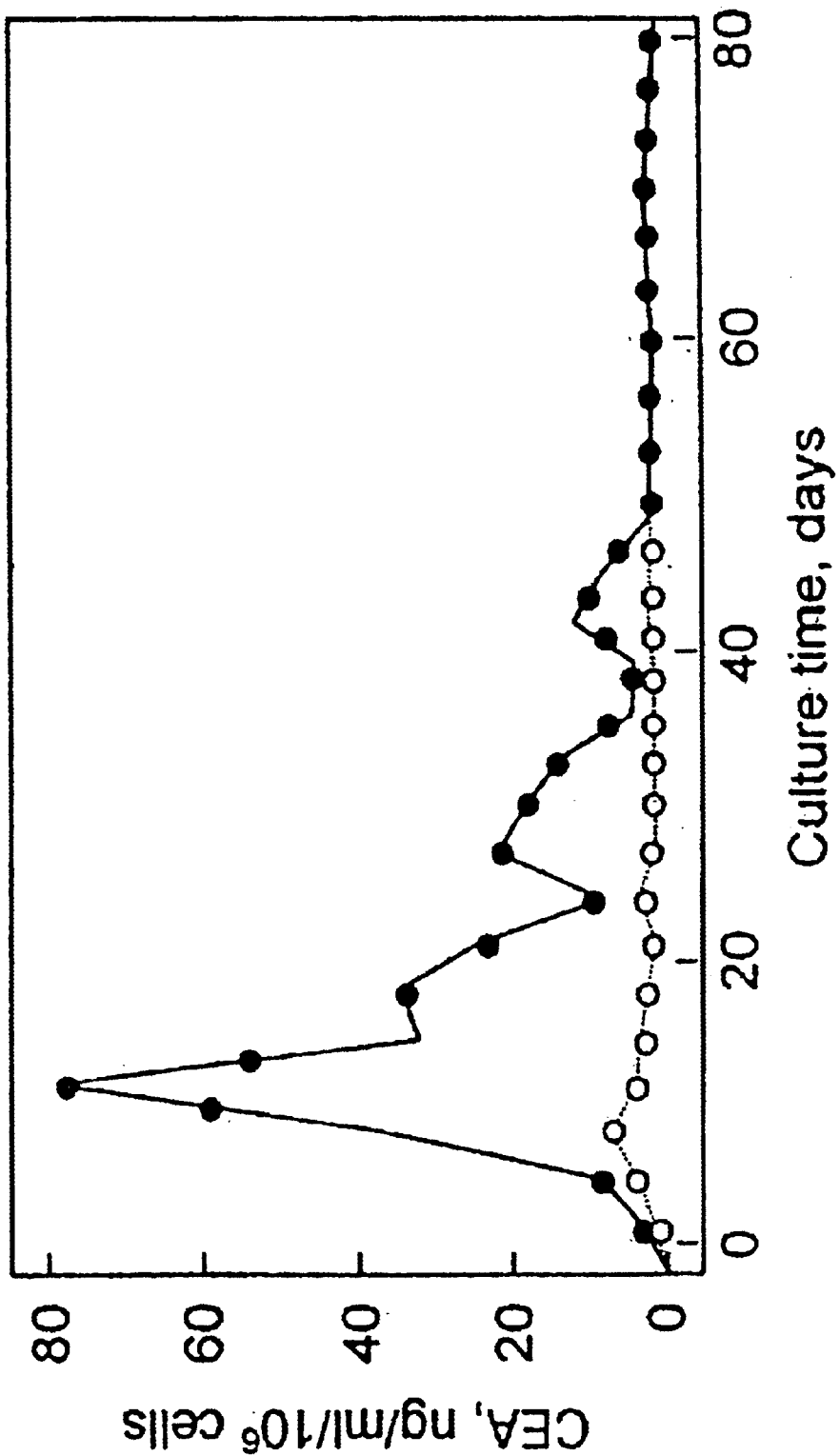
FIG. 11. CEA content of HT 29 colon cancer cells. During the quiescent proliferative period (days 3–40), there is over a 25-fold overproduction of the differentiation marker CEA (dark lines). Its production returns to control values (dotted line) when cell division resumes.

While HT 29 cell proliferation is markedly reduced, the cells are not metabolically quiescent since the contents of a number of differentiation markers that are either secreted into the medium or remain within the cells are increased. Within the first three days of exposure to biliverdin, the amount of CEA secreted into the medium by HT 29 cells increases from that of its constitutive production of slightly below 3 to over 80 ng/ml/$10^6$ cells by days 9–12 (FIG. 11). Thereafter, CEA content in the medium decreases progressively even though biliverdin is still present in the medium. Beyond day 45, when cell division resumes, the CEA marker content returns to the level of control cells. This lower production persists for the entire observation period of over a month.

Figure 12:
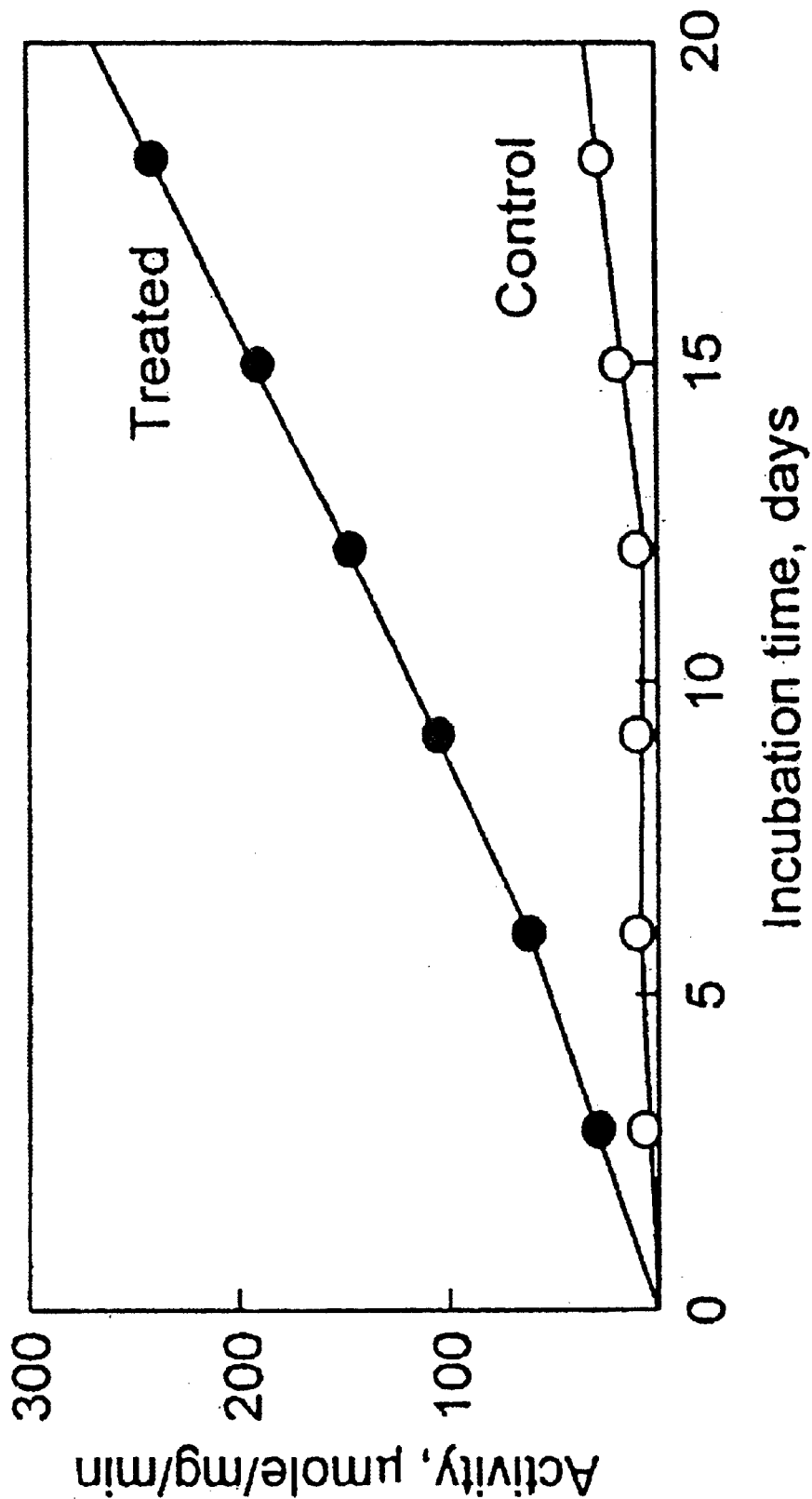
FIG. 12. Effect of biliverdin on alkaline phosphatase activity. Cellular alkaline phosphatase activity in treated cells (dark line) increases during the entire exposure to biliverdin compared to that of untreated control cells (thin line) that remain constant.

The control alkaline phosphate activity is nearly constant during the entire study period (FIG. 12). By the sixth day of incubation with biliverdin, the enzyme activity increases progressively reaching a fifteen-fold peak by day 20. Biliverdin also induces an over expression of triacyl glycerol (Table VII). The cytoplasm becomes filled with fat droplets that visibly changes the morphology of the cells and are readily seen by staining the cells with oil red O.

Figure 10:
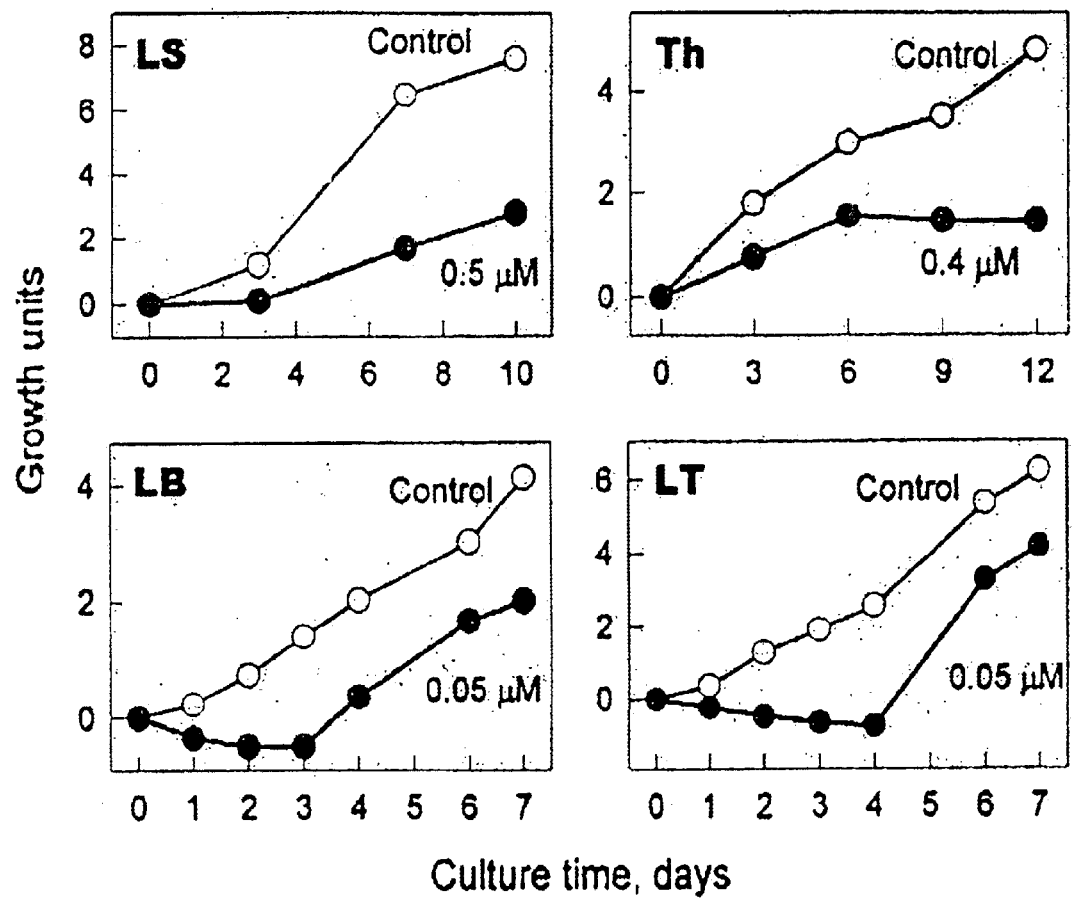
FIG. 10. Effect of biliverdin on proliferation of liposarcoma (LS), thyroid cancer (Th), B-lymphoblast (LB) and T-lymphoblast (LT) cells. Growth curves for treated cultures (●) and for control (○). The LB, LT and LS cells are arrested in their proliferation within one day while the Th cells respond after 6 days.

Other cancer cells. Biliverdin also affects the proliferative rate of liposarcoma, thyroid carcinoma and two lymphoblast cell lines (FIG. 10). The liposarcoma and lymphoblasts cease proliferating within one day while that of thyroid carcinoma requires six days. The liposarcoma cells resume division after day 3, but compared with control populations, at a markedly reduced rate (FIG. 10, LS). The thyroid carcinoma did not recover its proliferative rate at all for the 12-day observation period (FIG. 10, Th). Compared with their respective controls, liposarcoma and thyroid carcinoma divide 3.3 and 4.7 times slower, respectively. The lymphoblasts resume cell division within 3–4 days at nearly the same rate of control despite remaining exposed to the tetrapyrrole (FIG. 10, LB, LT).

TABLE VI

Distribution of Cell Cycle Stages of HT 29 Cancer Cells, %

| Conditions | $G_1$ | S | $G_2$ |
|---|---|---|---|
| Control | 42 | 47 | 11 |
| Biliverdin | 63 | 30 | 7 |
| Troglitazone[26] | 67 | 13 | 16 |

Liposarcoma cells also accumulate triacyl glycerol in response to biliverdin. The extent of the accumulation is determined by the composition of the incubation media. Triacyl glycerol is induced in liposarcoma cells by insulin alone. The amount increases when bovine pituitary extract is added with the insulin. The highest production is achieved, however, when biliverdin is combined with insulin plus bovine pituitary extract.

TABLE VII

EFFECT OF BILIVERDIN ON CELLULAR TRIACYL GLYCEROL (TAG) CONTENT

| Cell Type | TAG, mg/$10^6$ cells | % Change |
|---|---|---|
| Colon Adenocarcinoma | | |
| 1) Control | 68 | — |
| 2) Biliverdin (4 × $10^{-7}$ M) | 105 | 154 |
| Liposarcoma | | |
| 1) Control | 12.3 | — |
| 2) Insulin (5 µg/ml) | 17.1 | 139 |
| 3) Insulin (5 µg/ml), Pituitary Extract (20 µg/ml) | 20.7 | 168 |
| 4) Insulin (5 µg/ml), Pituitary Extract (20 µg/ml) and Biliverdin (4 × $10^{-7}$ M) | 33.5 | 272 |
| Normal Fibroblast | | |
| 1) Control | 9.3 | — |
| 2) Insulin (5 µg/ml) | 28.3 | 304 |
| 3) Insulin (5 µg/ml) and Biliverdin (4 × $10^{-7}$ M) | 54.5 | 586 |

These compounds also affect the timing for the fat accumulation. After 9 days of incubation with insulin and bovine pituitary extract, but without biliverdin, the fat droplets in the cells are small and scattered diffusely throughout the cell. These globules continue to enlarge to fill most of the cytoplasmic space by day 14. In contrast, by day 7 the cells incubated in the presence of biliverdin already contain large, grouped and prominent droplets. While the triacyl glycerol content increases in both HT 29 and liposarcoma cells, the fat droplets in HT 29 cells are smaller than those that fill the cytoplasm of the liposarcoma cells. 3T3-L1 fibroblasts differentiate into adipocytes in the presence of insulin (Table VII). In the absence of biliverdin, this hormone increases the triacylglycerol content of 3T3-L1 fibroblasts by 3-fold relative to control. When biliverdin is added, a progressively greater content of triacyl glycerol is achieved at day 9. The increase is dependent on the biliverdin concentration. At the highest concentration used, 4×$10^{-7}$ M, there is a 5.8-fold increase of triacyl glycerol content over that of the undifferentiated fibroblasts (Table VII). This almost doubles the amount in the cells incubated with differentiation medium alone and is nearly as high as observed with troglitazone. At a lower biliverdin concentration, $10^{-8}$ M, there is a 3.5-fold increase compared to control values. Remarkably, the amounts of biliverdin required to achieve the effects on proliferation, cell cycle and differentiation marker up-regulation, i.e. $10^{-7}$–$10^{-06}$ M, are the same as those needed to re-establish the capacity of embryos depleted of the tetrapyrrole by treatment with UV-light to form a dorsal axis.

HT 29 colon adenocarcinoma and liposarcoma were studied since criteria for their differentiation are known. The criteria include persistence of the CDK inhibitors p21 and p27, underphosphorylation of Rb protein, proliferative arrest associated with accumulation in $G_1$ stage of the cell cycle and increases in differentiation markers such as CEA, alkaline phosphatase and triacyl glycerol (for HT29 colon adenocarcinoma cells) and triacyl glycerol (for liposarcoma cells). These and other phenomena of the differentiation process have been described following exposure of stem cells and/or cancer cells to retinoids, troglitazone, vitamin $D_3$ derivatives and bistremide-A.

Biliverdin is a biological active molecule capable of inducing differentiation on a broad number of targets including embryos and adult normal and malignant cells. This is a novel conclusion since biliverdin is considered to be a breakdown product of heme without a metabolic function. However, biliverdin is present normally in the embryo, not as a byproduct of heme metabolism to be discarded once converted into bilirubin, but as a primary product synthesized in the maternal liver following estrogen stimulation, loaded onto vitellogenin, secreted into plasma, taken up by the oocyte and stored for years in the yolk platelets. Once fertilization has taken place, the biliverdin is used up within hours as a necessary pre-requisite to establishing a dorsal axis. This first indication that the tetrapyrrole has a function is now extended by the current findings and is supported by at least one other independent study. In that latter study, the phorbol ester TPA and hemin are each shown to induce differentiation of a leukemic cell. An associated biochemical phenomenon in cells exposed to TPA is the up-regulation of heme oxygenase 1 (HO-1), the enzyme that catabolizes the conversion of heme to biliverdin. As a consequence, the biliverdin content of TPA-exposed and differentiating cells is increased. The up-regulation of HO-1 appears to be a necessary step for induction of the differentiation since inhibition of the oxygenase activity by tin protoporphyrin, suppresses both the conversion of heme to biliverdin and the differentiation by TPA. These findings, together with the present results suggest, therefore, that the differentiation process produced by TPA needs to be examined in the context of the possible role of cellular biliverdin content as a mediating agent. The confirmation of this possibility has intriguing implications to the corresponding differentiating effect of hemin itself, a molecule that differs from heme, the precursor of biliverdin, only in the oxidation state of its iron. Since both hemin and biliverdin induce differentiation, we propose that it is the protoporphyrin molecular structure that is the active principle for both of them. Furthermore, the iron species in hemin, absent in biliverdin, is not necessary for hemin-induced differentiation.

The molecular mechanism of action for these effects of biliverdin (and that of one of its possible precursor hemin) on cancer and normal cells is currently unknown. However, biliverdin may act as a ligand to one or more intracellular receptor(s) that then activate (or repress) many genes that are required for differentiation and development. This latter mechanism is descriptive of the nuclear receptor family where diverse ligands, such as retinoids, prostaglandins and other hormones, interact with specific receptors that bind to and activate sets of genes containing common response elements. A well-studied example is troglitazone, a ligand for PPARγ that differentiates fibroblasts and liposarcoma cells. These ligand dependent reactions encompass particular differentiation pathways yet to be fully elucidated. We already know that biliverdin does not use either the retinoid signaling system (RAR or RXR) or the peroxisome proliferator-activated receptor (PPARγ) system. Therefore, if the biliverdin effect on cancer cells reported here is mediated by a receptor-activated mechanism, it is a hitherto unrecognized system that represents a novel differentiation pathway. The aryl hydrocarbon receptor is activated by biliverdin at the concentrations used here. Similarly, protoporphyrin IX and hemin appear to be endogenous ligands for mitochondrial benzodiazepine receptors. The search for the putative receptors that function in developmental and differentiation processes following binding to biliverdin is under active study.

Other mechanisms both at the level of transcription and/or translation need to be considered. Biliverdin could act directly as an inhibitor of proteolytic or lipolytic processes that increase the amounts of varied cellular proteins and lipids. Alternatively, other effects on e.g. mRNA degradation or stimulation could pertain.

EXAMPLE III

Transport and Storage of Biliverdin

Biliverdin is a constituent of vitellogenin and lipovitellin, and therefore, the material contained in the oocyte/egg/embryo originates in the maternal liver. Vitellogenin transports biliverdin in the maternal plasma and carries it into the oocyte. Biliverdin is stored for years as a complex within the yolk platelet protein lipovitellin. In contrast to this long period of storage during oogenesis, once the embryo is formed, biliverdin exerts its fimction within the first cell cycle. Then, the total content of biliverdin in the embryo decreases progressively in the first five hours after fertilization and prior to the rnid blastula transition.

The distribution of biliverdin within the egg was determined by establishing its presence in separated cell compartments. Freshly spawned eggs were dejellied and then manually homogenized in 5 vol of 0.25 M sucrose, 20 mM Tris, 50 μM leupeptin, pH 7.5, 2° C. (buffer A). One ml of the homogenate was loaded onto a stepwise sucrose gradient and spun in an SW40 rotor (Beckman) at 25 000 rpm, 0° C., for 22 hours as described previously (Montorzi et al, 1995; Falchuk et al. 1995). Five egg fractions were separated into the following densities (in g/ml): <1.07, 1.08–1.15, 1.16–1.20, 1.21–1.26, 1.27–1.30. The biliverdin content of each fraction was analyzed after extraction with two volumes of the organic extraction solvent mix composed of 8 parts ethyl acetate, 1 part methyl acetate and 50 μg/ml butylated hydroxy toluene. The fraction that retained the green color characteristic of biliverdin was recovered and dried.

The dried extracted non-volatile green residuals obtained from each extract were dissolved in 10% acetonitrile, 10 mM ammonium acetate, pH 6.5. Aliquots of 250 μL were loaded onto a Jupiter 5 μ $C_{18}$ 300 Å 250×4.6 mm column (Phenomenex) connected to a Waters 510 HPLC pump and a Waters Automated Gradient Controller. The eluate was monitored at 340 nm with a Waters 440 Absorbance Detector and the data recorded with a Hewlett Packard 3390 Integrator using a binary solvent system. The initial solvent was ammonium acetate 10 mM, pH 6.5, and the final buffer was 100% acetonitrile. The gradient design was: 0–100% ending solvent with a linear increment from 5 to 45 min, then 100% ending solvent from 45 to 60 min. A wavelength absorbance scan was performed on selected fractions with a Varian-Cary 50 Bio UV-Vis spectrophotometer. A control sample of previously purified commercial biliverdin (Sigma, St. Louis, Mo.) was treated similarly with organic solvents, chromatographed under the same conditions and used as a standard (Falchuk 2001). Selected HPLC samples were dissolved in equal volumes with methanol and submitted to mass spectrometric analysis with a Finnigan LCQ ion trap mass spectrometer.

The time course for biliverdin appearance and accumulation in oocytes during oogenesis and its utilization during early embryogenesis was examined. Oocytes at different stages of maturation were selected according to standard morphological criteria (Dumont 1972). Stage I and II oocytes were obtained directly from the ovaries of 2–3 cm length young female frogs. Stages III–VI oocytes were obtained by dissection of adult 6–7 cm frog ovaries as previously described (Nomizu 1993). Spawned eggs were fertilized in vitro and the embryos were staged according to the standard *X. laevis* developmental table (Nieuwkoop 1967). Oocytes and embryos selected at targeted stages of development were homogenized in one volume of ice cold stabilizing buffer composed of EDTA 30 mM, ascorbic acid 30 mM, Tris 20 mM, pH 7.4. Oocyte and embryo homogenates were extracted and their biliverdin content analyzed as described above.

Vitellogenin was purified from the serum of adult female *X. laevis* frogs according to previously reported methods (Montorzi 1995). The animals were injected in the dorsal lymph sac with 2 mg of estradiol valerate (Bristol-Myers-Squibb Co, NJ). Twenty-one days later the frogs were anesthetized and their blood extracted by direct heart puncture. The serum was diluted 1:1 with 20 mM Tris, pH 7.5. One ml was chromatographed in an HR 5/5 column packed with 1 cm$^3$ of Source 15Q resin (Amersham-Pharmacia Biotech, New Jersey) using an FPLC® system (Pharmacia) at a flow rate of 2 mL/min. Initial buffer was Tris 20 mM, pH 7.5 and final buffer was 1 M NaCl, Tris 20 mM, pH 7.5. The gradient design was 0 to 50% final buffer with a linear increment from 5 to 20 min. The eluate was recorded at 284 nm. The absorption at 375 nm was determined in selected fractions with a Varian-Cary 50 Bio UV-Vis spectrophotometer. The fractions with high absorbance at 375 nm were extracted with organic solvents using a ternary system consisting of one part of chloroform and two parts of methanol added to 0.8 part of either the serum or the selected fractions (Bligh 1959).

The yolk platelet proteins, products of vitellogenin processing, were purified from solubilized organelles (Falchuk 1995, Montorzi 1995). Yolk platelets were dissolved in 2 vol of 1.5 M NaCl, 30 mM Tris, pH 7.5, 2° C. (buffer B). The solubilized proteins were separated by selective precipitation with ammonium sulfate to a final concentration of 66% of the saturated concentration. The resultant ammonium sulfate suspension was spun at 30 000 rpm in a Beckman Ti80 rotor for 60 min at 2° C. The supernatant contains phosvitin while the pellet is composed principally of lipovitellin. The latter was redissolved in buffer B and then precipitated again with ammonium sulfate as described above. Finally, lipovitellin was dissolved in two vol of buffer B (Montorzi 1995, Falchuk 1995). One ml of the lipovitellin solution was loaded onto a glass column 120×1 cm (Bio Rad) packed with Sephacryl S-300 resin (Pharmacia), previously equilibrated with 1 M NaCl, 30 mM Tris, pH 7.5 (buffer C) at room temperature. The flow rate was 4.5 mL per hour and fractions of 2 mL each were collected. Fractions were individually read for their absorption at 280 and 375 nm with a Varian-Cary 50 Bio UV-Vis spectrophotometer. Standard SDS polyacrylamide gel electrophoresis and amino acid analyses were performed as described (Montorzi 1995).

Figure 13:
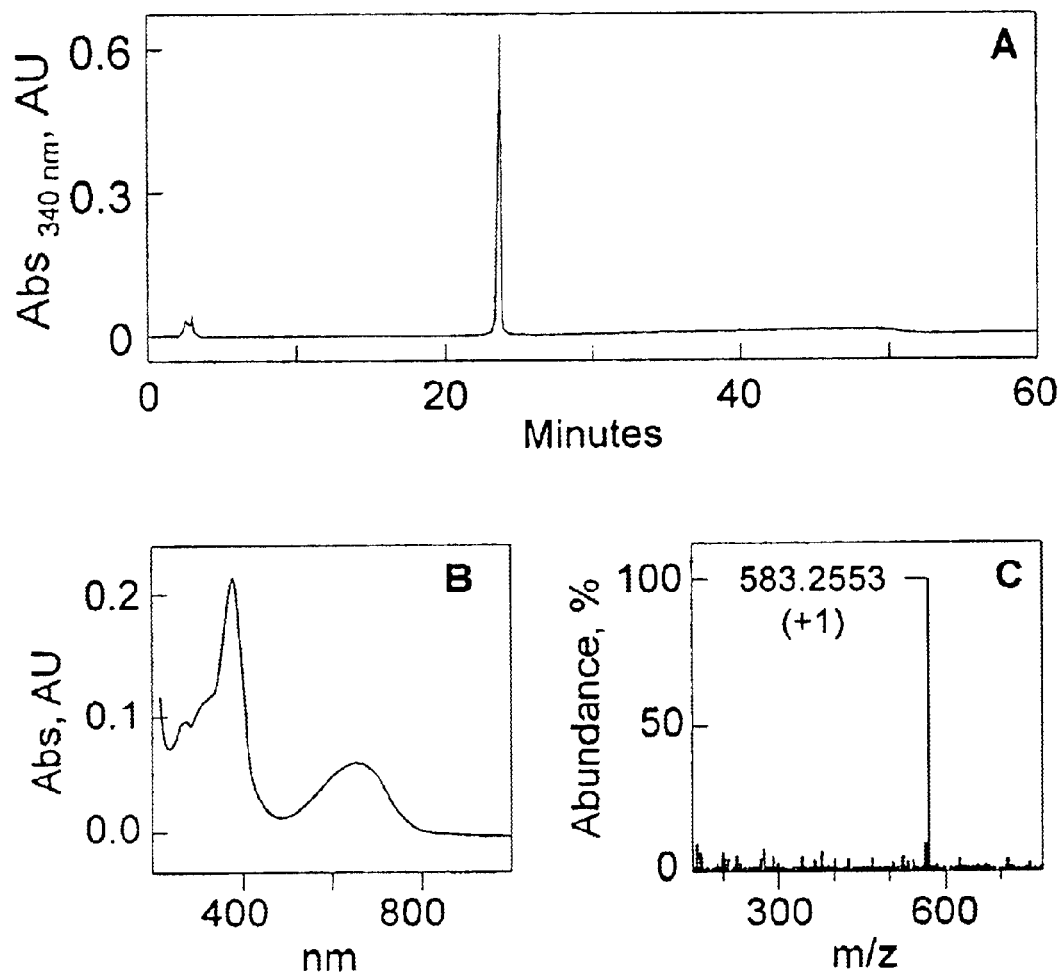
FIG. 13. HPLC purification and analysis of an organic solvent extract of serum, vitellogenin, lipovitellin and yolk platelets. (a) A fraction eluting at 23.3 min is present in the HPLC chromatogram of each extract. (b) The UV-Vis $_{200-1000}$ nm spectrometric analysis of the 23.3 min fraction has characteristic absorption peaks at 375 and 665 mn. (c) Its mass spectrometric analysis generates a high abundance signal of 583.2553 m/z. The chromatographic behavior and spectrometric results are identical to that of biliverdin standard. Biliverdin is present in all samples and accounts for their blue-green color.

The fractions with high absorbance at 375 nm were extracted with the same ethyl acetate/methyl acetate mixture as was carried out with the oocyte and embryo homogenates. The resultant extracts were chromatographed by reversed phase HPLC as described. The HPLC fractions eluting at 23.3 min from the lipovitellin and vitellogenin extracts were analyzed by mass spectrometry and compared with the spectrum of a commercial biliverdin standard sample that was treated previously in a similar way, by organic solvents and HPLC separation. FIG. 13.

Figure 14:
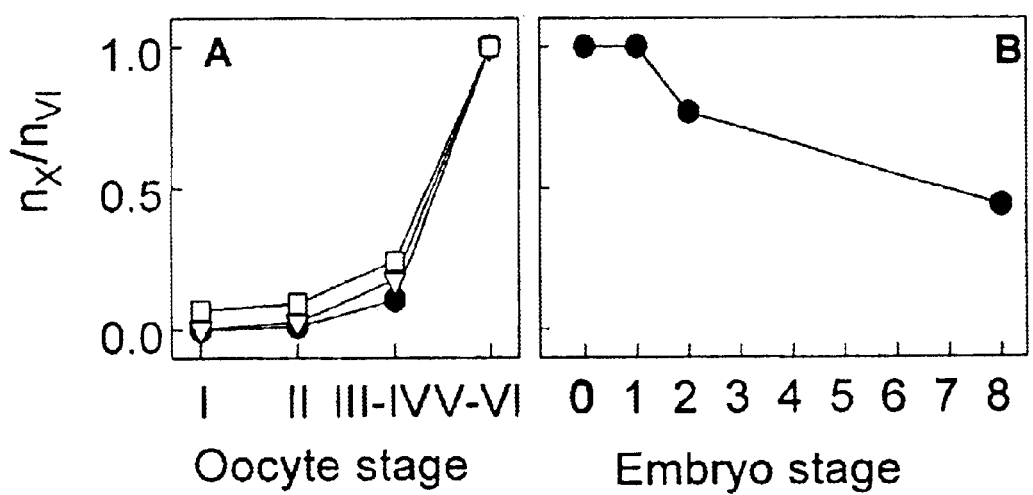
FIG. 14. (a) Normalized values for oocyte volume and their biliverdin and zinc content at different stages of maturation. The ratios represent the value of the measured variable at any given stage ($n_x$) divided by the value at stage VI ($n_{VI}$). Zinc and volume values for each oocyte maturation stage were adapted from previous publications Nomizu 1993, Tanabe 1974, Hausen 1991). The biliverdin content increases progressively during oogenesis [●]. Its incremental accumulation correlates with that of zinc (□) and volume [▽]. (b) In the embryo, the biliverdin content [●] decreases steadily after fertilization. At stage 8, it is decreased to less than a half of the original amount in the egg.

The presence of biliverdin in mature eggs allowed the examination of the time course of biliverdin accumulation in oocytes and utilization in embryos during oocyte maturation and embryogenesis, respectively. The tetrapyrrole is barely detectable in stage I–II oocytes but increases significantly and progressively in stages III–VI (FIG. 14), the so-called vitellogenic phases. These changes during the vitellogenic phase of oogenesis are reminiscent of those observed for zinc (Nomizu 1993, Montorzi 1995, Falchuk 1995) and for volume increase (Wall 1987, Danilckik 1987, Hausen 1991). Thus, the oocyte volume and zinc content also increase during oogenesis and the curves of their incremental accumulation correlate closely with that of biliverdin (FIG. 14). This correlation suggests a possible common mechanism for their individual increases. We had previously demonstrated that zinc incorporation by the oocyte depends on the import of zinc-vitellogenin and its processing into the predominant proteins of yolk platelets, zinc-lipovitellin and phosvitin. Thus, one mole of vitellogenin contains one mole of zinc (Montorzi 1995). Zinc in vitellogenin accounts for well over 95% of the zinc in the oocyte (Falchuk 1995). Hence, any increase of zinc corresponds to an increase in vitellogenin. As greater quantities of vitellogenin are taken in and processed within yolk platelets, these organelles increase both in size and density leading to an increase in oocyte volume (Danilchik 1987). Since the time course of biliverdin accumulation during oogenesis correlates to these other two variables it suggests that its accumulation in the oocyte also may be governed by internalization of vitellogenin and yolk formation.

Figure 15:
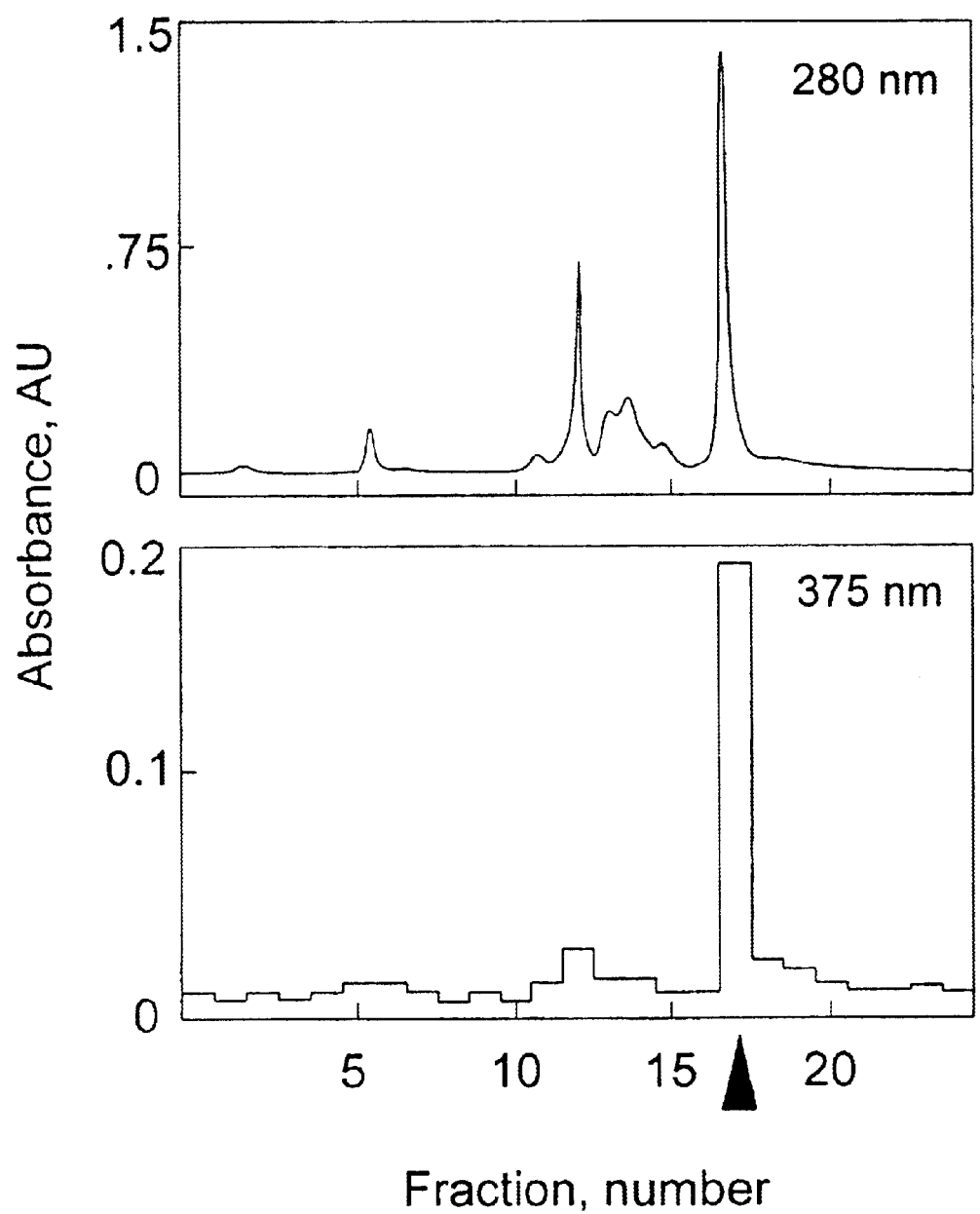
FIG. 15. Vitellogenin purification from frog serum by Fast Protein Liquid Chromatography®. A source 15Q resin was used for the chromatography of the serum. (a) The serum contains a number of proteins that are resolved into distinctive peaks monitored at 280 nm (b) Only one fraction (arrow) contains biliverdin with its absorption peak at 375 nm and retains the blue-green color of the serum.

This premise is now confirmed by the finding that biliverdin is an intrinsic component of vitellogenin. Subsequent to estrogen administration, vitellogenin synthesis is induced in the frog's liver and secreted into the blood stream. The normally yellow plasma acquires an intense green color. Protein components of the green serum are fractionated by chromatography with a Source 15Q resin. Many of the eluting fractions absorb at 280 nm but only fractions 17 and 18 also absorb significantly at 375 nm (FIG. 15). These fractions are the only ones that retain the green color of the serum loaded onto the column. The amino acid composition of the peak fraction 17 (FIG. 16) is comparable to literature values for vitellogenin (Montorzi 1995) and confirms that fractions 17 and 18 contain pure vitellogenin. The green chromophore was extracted separately with organic solvents from serum and from purified vitellogenin. In both cases, the green chromophore had a retention time and spectral characteristics identical to those of biliverdin extracted from oocytes and eggs (FIG. 13). Therefore, the presence of a biliverdin-vitellogenin complex in the serum of estrogen-stimulated frogs contributes to its green color.

The isopycnic fractionation of egg homogenates separates cytosol, mitochondria, light and dense yolk platelets, nuclei and peroxisomes (Montorzi, 1995). Analysis of the biliverdin content in these egg constituents demonstrates that the tetrapyrrole is found principally in layers with densities between 1.21 and 1.23 g/ml. These are the layers that concentrate and separate yolk platelets. Therefore, the majority of biliverdin is localized to yolk platelets. A smaller amount of biliverdin appears in the heavier fractions that typically contain peroxisomes and nuclei, but may also contain the heaviest and densest yolk platelets or represent a carry-over phenomenon of yolk platelets as the fractions are collected.

Figure 16:
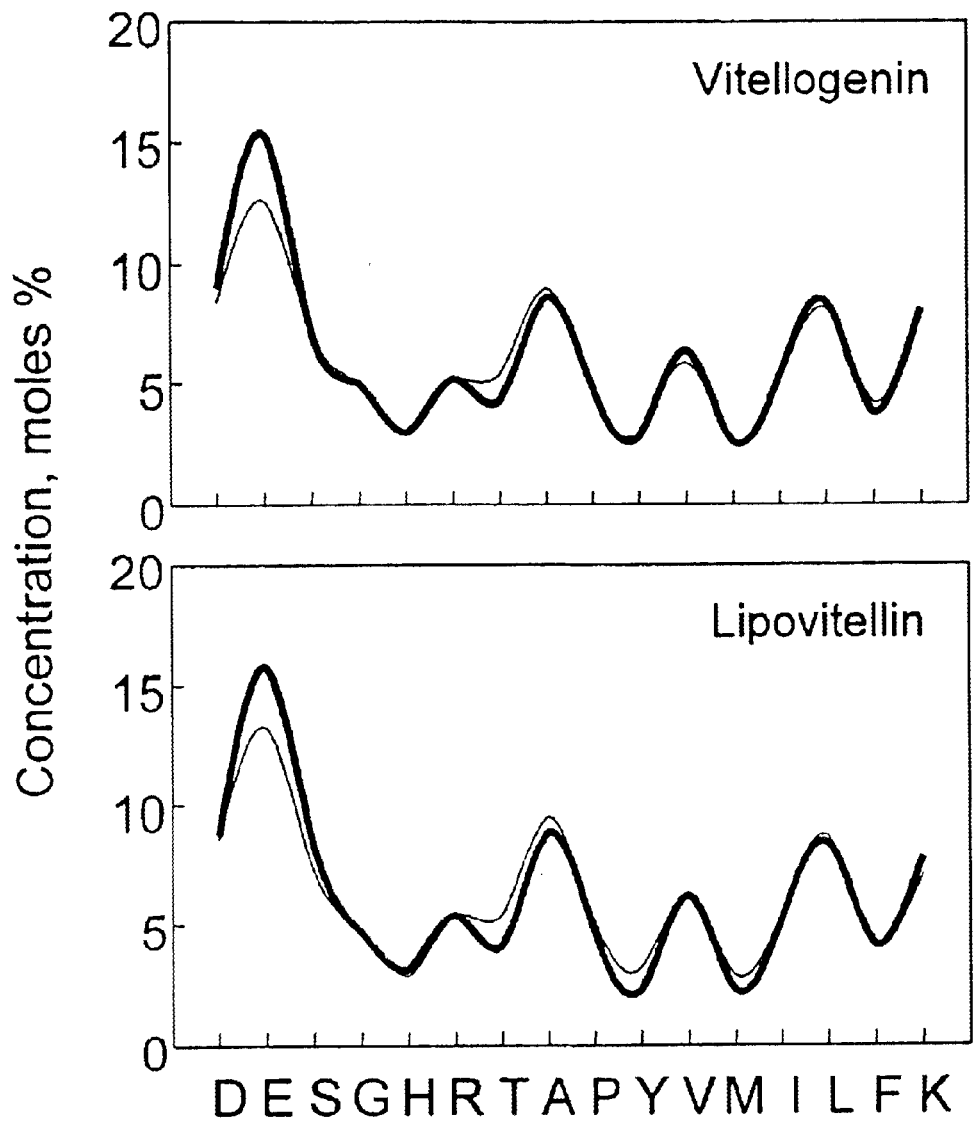
FIG. 16. Amino acid analysis. The abundance of each amino acid analyzed was calculated and plotted in percent of the total moles measured. The data point values for each amino acid where linked with a smoothed (spline) line for ease of display and comparative purposes. The present values obtained for this report (heavy lines) were compared to reference ones (light lines) of either vitellogenin or lipovitellin (Montorzi 1995). (a) Comparison of fraction 17 (see FIG. 3) with vitellogenin reference. (b) Comparison of fraction 15 (see FIG. 5) with lipovitellin reference.
Figure 17:
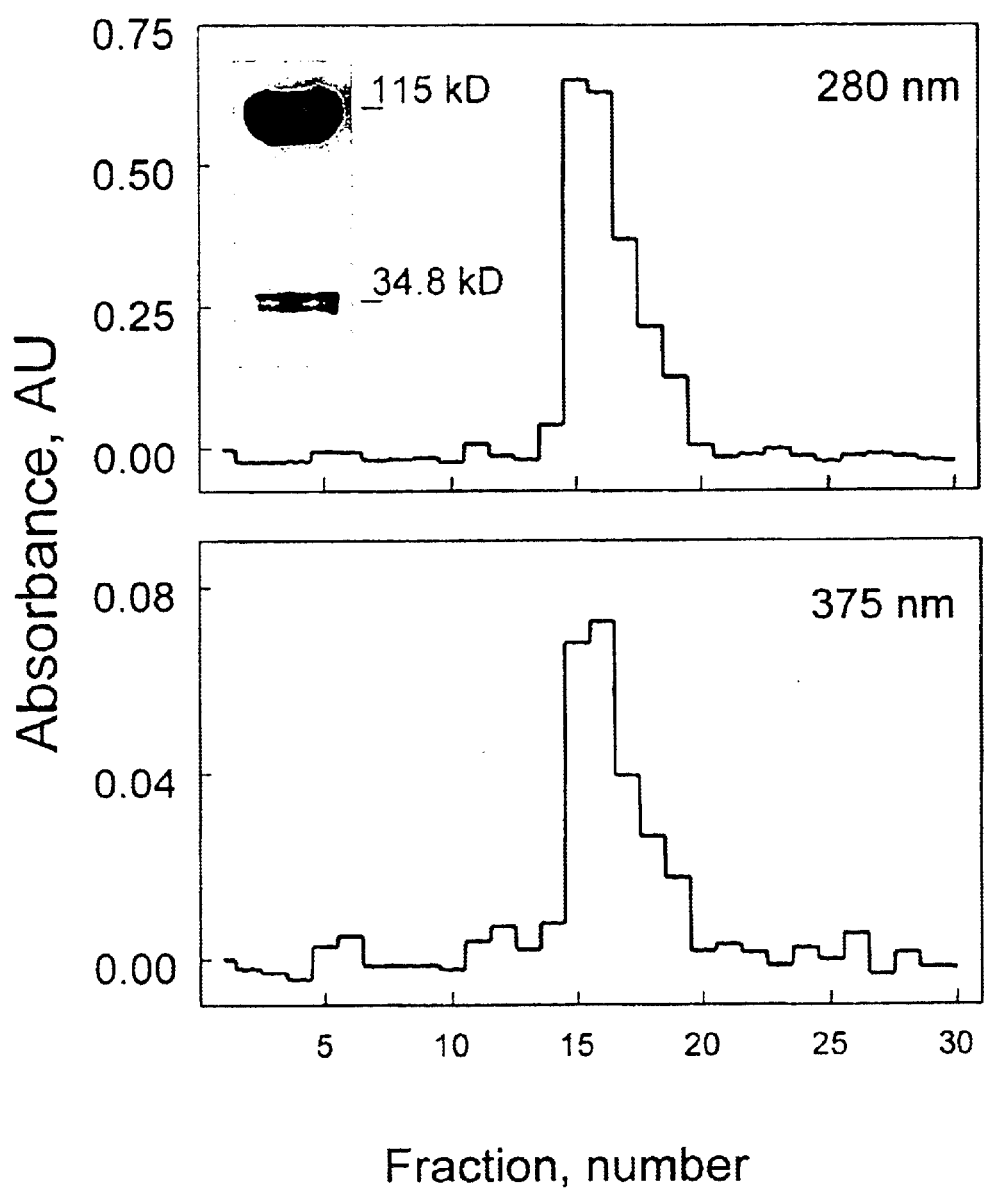
FIG. 17. Size exclusion Sephacryl S-300 column chromatography of lipovitellin. A single predominant peak (fractions 14–18) absorbs significantly at (a) 280 and (b) 375 nm. Insert: SDS polyacrylamide gel electrophoresis of fraction 15 (peak). Three separate bands are resolved, consistent with LV1, LV2α and LV2β. The marks next to the gel correspond to the relative mobilities of the molecular weight standards.

In the yolk platelets, biliverdin is associated with lipovitellin. The yolk platelet proteins are solubilized with NaCl. Lipovitellin can be separated from phosvitin by treatment with ammonium sulfate because the former is selectively precipitated while the latter remains in the supernatant after ultracentrifugation. The pellet containing lipovitellin is green and exhibits absorption peaks at 375 nm and 665 nm characteristic of biliverdin. The phosvitin-containing ammonium sulfate supernatant is not green and does not absorb at this wavelength. Size exclusion chromatography on Sephacryl S-300 column further purifies lipovitellin by separating smaller peptide fragments from the LV1–LV2 complex (FIG. 17). Fractions 14–18 collected from the size exclusion chromatography experiment absorb both at 280 nm and 375 nm. The peak fraction 15 resolves into three bands on SDS gel electrophoresis (FIG. 17 insert). The bands are identified with Coomassie blue staining. The larger one displayed an electrophoretic migration close to the 115 kDa marker ($\beta$-galactosidase) and the two smaller ones migrate close to the 34.8 kDa marker (carbonic anhydrase). These values, in conjunction with the morphology of the bands, are consistent with the reported molecular weight of lipovitellin 1 (~115 kDa), lipovitellin $2\alpha$ (~35 kDa) and of lipovitellin $2\beta$ (~32 kDa) (Ohlendorf 1977, Wiley 1981, Montorzi 1995). The amino acid composition of fraction 15 confirms the assignment of the identity of the protein as lipovitellin and certifies the peak as pure (FIG. 16). The amino acid content (mole %) is comparable to the reference amino acid composition of lipovitellin (Montorzi 1995). Therefore, the peaks recorded at 280 and 375 nm co-elute in the same fractions and contain lipovitellin 1 and lipovitellin 2 in complex form.

The green chromophore of lipovitellin was extracted with organic solvents and the extracted material was resolved by HPLC on a $C_{18}$ column. The BPLC elution profile of the lipovitellin extract recorded at 340 nm disclosed one main peak with a retention time of 23.3 min, identical to the retention time of the extracts from vitellogenin, the oocytes and eggs. The UV-Vis $_{200-1000\ nm}$ wavelength scan of this fraction demonstrated the characteristic absorption spectrum of biliverdin confirmed by its molecular weight of (+1) 583.2553. Both results also are identical to the characteristics of purified commercial biliverdin used as standard. Jointly, these results indicate that biliverdin is bound to lipovitellin in the yolk platelets.

Whereas biliverdin increases progressively during oogenesis (FIG. 14), once the egg is fertilized, its content in the embryo decreases. From its maximum in the mature egg, it falls to less than half by stage 8 of development or approximately 5 hours after fertilization (FIG. 14).

Figure 18:
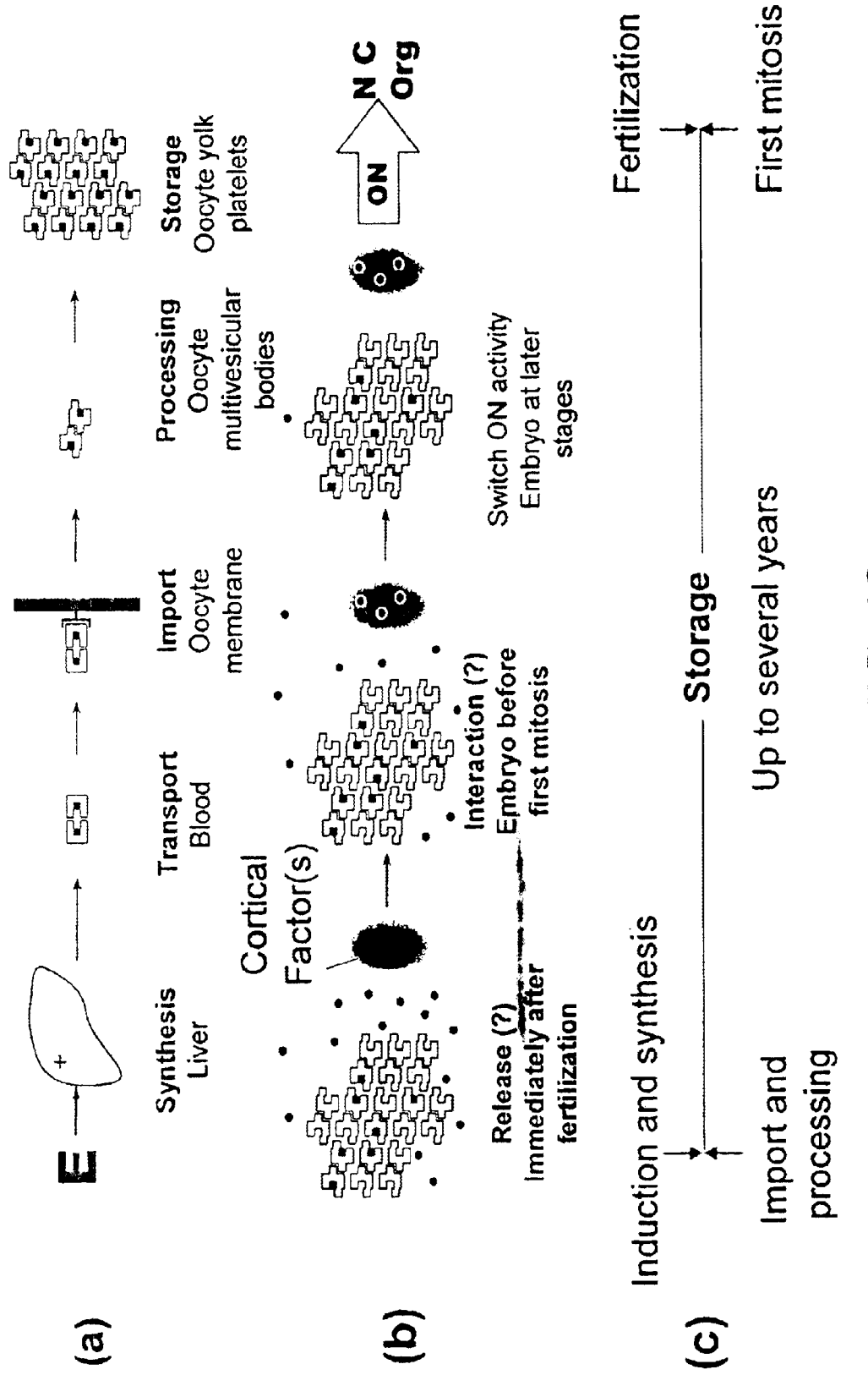
FIG. 18. Model of metabolic pathway of *Xenopus laevis* biliverdin. (a) Estrogen induces the hepatocytes to synthesize vitellogenin. Since biliverdin is a constituent of this protein, estrogen must induce the synthesis of the former as well. Once the tetrapyrrole is incorporated into vitellogenin, the complex is excreted into and transported in the frog plasma. Biliverdin is the signal molecule and vitellogenin is the carrier. The carrier, vitellogenin, binds to receptors expressed on the cell membrane surface of oocytes and it is internalized with the signal molecule, biliverdin, inside. Once in the oocyte, vitellogenin is processed to lipovitellin/phosvitin complexes. These complexes aggregate in a modular arrangement in yolk platelets. Lipovitellin binds the biliverdin molecule. (b) After fertilization, biliverdin interacts with a cortical factor(s) to establish sequentially the dorsalizing centers (Falchuk 2001). We propose that biliverdin is released from lipovitellin to exert its action. Biliverdin in conjuction to the cortical factor(s) switch-on downstream events that determine the sequential formation of the dorsalizing centers, the Nieuwkoop center [NC] and the Speeman-Mangold organizer [Org]. (c) Time line for biliverdin production, storage and activity. The first phase of biliverdin production and export lasts from few hours to few days. It comprises induction by estrogen of the maternal hepatocyte, synthesis of the biliverdin-vitellogenin complex, release of the complex to the circulation, import by the oocyte and processing. The second phase is the storage of biliverdin bound to lipovitellin in the oocyte. It could last up to three or more years, that is over 99.99% of the molecule's existence. Biliverdin integrity has to be protected and guaranteed during all this time. The third phase is the time when biliverdin exerts it activity. It happens in the first cell cycle of the embryo (usually in the first 100 minutes post fertilization). Biliverdin acts in a different organism than the one where the molecule originated.

Biliverdin is linked intimately to that of vitellogenin, including its upregulation in the liver by estrogens, its secretion into the plasma, its uptake by oocytes and its processing in yolk platelets (FIG. 18). Vitellogenin is a 220 kDa protein synthesized by hepatocytes following estrogen activation of its genes. The holo-protein contains zinc, calcium, phosphate, carbohydrate and lipid. All of these intrinsic constituents of vitellogenin are incorporated into the protein during its synthesis (Montorzi 1994, Montorzi 1995, Dolphin 1971, Wallace 1970). Vitellogenin also contains biliverdin $IX\alpha$. As with the other intrinsic constituents, it is likely that the tetrapyrrole, is incorporated into the protein during its synthesis in the hepatocyte. This requires the generation of sufficient amounts of biliverdin to associate with the nascent vitellogenin. A point of departure to begin to understand how the tetrapyrrole might be formed and how its metabolism might be linked to that of vitellogenin is to review the available information on biliverdin biochemistry and place it in context with vitellogenin synthesis in the liver and processing in the oocyte (FIG. 18). In those species studied, biliverdin is formed as a product of heme breakdown in mononuclear phagocytes. In these cells, the microsomal enzyme heme-oxygenase catalyzes the oxidation of heme to $\alpha$-OH-hemin with a ferric ($Fe^{+3}$) cation (Tenhunen 1969, Ishizawa 1983). Then, in a subsequent non-enzymatic step, biliverdin is formed after the release of $Fe^{+3}$ and a molecule of CO (King 1978). Biliverdin binds to albumin (Blauer 1975) and the protein-tetrapyrrole complex is internalized by hepatocytes expressing receptors for the protein (Ockner 1983). Once in the liver, biliverdin binds to ligandins and undergoes further processing (Wooley 1976). If these biochemical processes pertain to estrogen stimulated frogs, then the hormone might regulate heme breakdown directly. Alternatively, since in the frog, biliverdin is an essential metabolite, its formation cannot be considered to be solely a heme degradation product. Therefore, other pathways for making biliverdin in the liver may be operative in the frog, including hitherto unrecognized synthetic ones.

Estrogens stimulate the microsomal fraction (Sergeev 1975) and induce changes in the architecture subcellular organelles including the Golgi apparatus (Lewis 1976). Conceivably, biliverdin synthesis could be induced or favored by estrogen and vitellogenin could be modified post translationally to include the tetrapyrrole in its structure. In any case, once the biliverdin-vitellogenin complex is formed, the protein acts as the vehicle to transport biliverdin in the plasma from its site of origin, the liver, to its site of storage in the oocyte. Normally, the frog's plasma is yellow, but following high dose estrogen administration, it becomes green owing to the high amount of biliverdin-vitellogenin product induced by the over stimulation and secreted into the blood stream.

Biliverdin is brought into the oocyte when the biliverdin-vitellogenin complex in the plasma is internalized by the oocyte after binding to membrane receptors on coated pits (Opresko 1987). Once in the oocyte, vitellogenin is processed within endocytosed vesicles that fuse with multivesicular bodies and then to yolk platelets. In these organelles, vitellogenin is hydrolyzed into various fragments that comprise lipovitellin 1 (LV1, ~115 kDa), lipovitellin 2 (LV$2\alpha$~35 kDA, LV$2\beta$~32 kDa) and phosvitin (PV, ~39 kDa). The resulting protein fragments (LV1, LV2 and PV) remain together in the form of a complex (Ohlendorf 1978). This complex, itself a trimer, binds to another trimer to form an aggregation unit. Inside the yolk platelets, these bi-trimer units polymerize in a quite characteristic microcrystalline array that has been examined by electron microscopy (Leonard 1972).

The biliverdin associated with vitellogenin is located in the domain that is processed into lipovitellin. This is consistent with finding that when yolk platelet proteins are solubilized and separated, the one that contains biliverdin is lipovitellin. The yolk platelets, therefore, become the storage site for biliverdin. The lipovitellin-tetrapyrrole complexes are stored in these organelles for several years, the period of time that it takes for an oocyte to develop from stage I to VI (Gilbert 2000).

A possible binding site of biliverdin to lipovitellin has been proposed. A series of studies conducted on lamprey lipovitellin by means of X-ray crystallography, $^{31}P$ $^{2}H$ NMR, neutron diffraction analysis and computer modeling, revealed a funnel shaped, lipid-rich cavity of 28,000 $Å^3$ buried inside the LV complex. Tentatively, one molecule of biliverdin was modeled inside this cavity (Anderson 1998). Hydrophobic amino acid residues are somewhat uniformly distributed over the lipid cavity surface that is bordered by two β-sheets. Based on the cavity volume, it has been estimated that it might contain 32 molecules of phospholipids (Timmins 1992) organized in a condensed fluid monolayer with weak and non-specific interaction with the protein (Anderson 1998). In the model proposed, the phospholipid hydrophilic heads form the aqueous interface at the mouth of the cavity and interact with the ring of polar amino acid residues, while the non-polar hydrocarbon tails almost fill the remaining hydrophobic cavity. These tails leave a space at the bottom narrow end of the cavity that could accommodate the neutral lipids.

A noteworthy implication for the presumed positioning of biliverdin in the bottom of the lipid cavity surrounded by a hydrophobic environment could be protection of its structural integrity from reactive hydrophilic molecules. A neutron diffraction study carried out on lipovitellin supports this speculation. In the study, a negative signal was detected when using $D_2O$ as a solvent and ascribed to represent the interior of the lipid cavity (Timmins 1992). Biliverdin is sensitive to variations in the redox state. Bilirubin is an immediate product after reduction of biliverdin, in a reaction that is catalyzed by biliverdin reductase (Schmid 1975, Seifried 1976). This reaction could take place non-enzymatically over the long time (up to several years) that yolk platelets are in storage in the maturing oocyte and slowly transform biliverdin. Considering the low aqueous/lipid partition coefficient of several compounds with redox activity and the characteristics of lipovitellin, this protein could provide an optimal chemical protection environment for biliverdin over the oocyte maturation period. The intra-compartmental pH of yolk platelets has been estimated to be 5.7 during maturation and 5 or less during embryogenesis (Fagotto 1994). Therefore, given a pKα of the propionic acid groups of biliverdin in that pH range (Lightner 1996), it may be predicted that in this chemical environment the molecule could be protonated and therefore lipophilic. This state could assure the permanence of the molecule in the hydrophobic cavity.

This model is consistent with the observation that even mild organic solvents can extract the biliverdin from lipovitellin and suggests a non-covalent binding of biliverdin to lipovitellin. This explanation could account for the easy extractability of biliverdin from lipovitellin and yolk platelets in our experiments and others (Redshaw 1971). While vitellogenin and its processed product lipovitellin, both contain biliverdin, the conditions required to extract the tetrapyrrole from each protein differ, indicating the presence of distinct chemical environments. The organic solvent extraction protocol used to extract biliverdin from lipovitellin, whether as found within oocytes, yolk platelets or as the purified protein, fails to extract the green pigment from the parent vitellogenin. An alternative ternary system (chloroform, methanol and the aqueous sample) was required to extract biliverdin from vitellogenin as a pure molecule or as found in serum. This difference in requirements for organic solvent extraction suggests that the particular protein structure of vitellogenin and lipovitellin impacts the exposure of the biliverdin-carrying site to the surrounding solvent.

Once the egg is fertilized, the embryo utilizes its stored biliverdin as one of the components required to generate a dorsal axis (Falchuk 2001). Toward that end, following fertilization the majority of the yolk platelets settle into the vegetal hemisphere of the embryo (Hausen 1991). This places yolk rich biliverdin in the region that will rotate toward the dorsal equatorial segment. Biliverdin then could be released in the operative dorsal region from its storage location in the lipovitellin complex during the narrow window of time before the first mitosis that occurs about 70 to 90 minutes after fertilization. Subsequent to its release, biliverdin triggers a series of events that result in the formation of the dorsal axis in the embryo (Falchuk 2001). The lipovitellin structure and architecture must have evolved to respond to specific signal(s) by allowing biliverdin to act at the proper time and place following fertilization (FIG. 18).

The release of biliverdin from lipovitellin could be accomplished through a number of possible mechanisms. One could be direct unloading from the lipid cavity following a conformational modification of the protein. Structural analysis of lipovitellin indicated that the lipid cavity could be flexible, allowing the content to be unloaded (Anderson 1998). In this setting then a transformation of the protein structure induced perhaps by an allosteric mechanism, could modify the cavity with subsequent release of biliverdin. Another possibility could be the release of biliverdin from the lipid cavity following proteolysis initiated immediately after fertilization. To date, no proteolytic enzyme has been demonstrated to exist inside yolk platelets. Protease inhibitors have been isolated and demonstrated to be associated to these vesicles (Slaughter 1976, Ezquieta 1986). These findings triggered speculation on the potential presence of a proteolytic enzyme in yolk platelets.

Once released from its complex with lipovitellin, we propose that biliverdin interacts with a cortical factor(s) as a required step of the signaling cascade that determines the dorsal axis (Falchuk 2001), a critical event in morphogenesis. This important role of biliverdin in dorsal axis formation requires that its storage protein and vesicle be conserved. This is consistent with the observation that the yolk proteins are highly conserved among a significant group of species —fish, teleosts, amphibians—whose common ancestor before the divergence of these species, might have existed 400 million years ago (Lange 1983, Stark 1978). Indeed, phylogenetic reconstructions of vitellogenin based on amino acid sequence identities indicate that this protein and other related ones from several phyla (insects, nematodes, vertebrates) are homologous (Chen 1997). Sequence analyses of vitellogenins indicate that the phosvitin domain has undergone a much faster evolutionary transformation than the lipovitellin domain (Byrne 1989, La fleur 1995). The high interspecies conservation and evolutionary stability of vitellogenin and in particular the lipovitellin domain, is consistent with the expectation that this protein has an intrinsically critical biological function highly dependent on its sequence, its three-dimensional structure and its physico-chemical properties. This is confirmed in part by the finding that the binding site for the vitellogenin receptor on the oocyte membrane is in the lipovitellin 1 domain of the molecule (Stifani 1990).

Other developmentally important molecules to that are associated with yolk proteins have been described. Eggs of the insect *Locusta migratoria*, contain molecules with cell induction properties that are bound to a yolk protein. These are molting hormones in the form of conjugates of ecdysone and 2-deoxyecdysone that are bound to vitellin, a 520 KDa yolk protein related to vitellogenin. In this system, ecdysone and vitellin are synthesized exogenously to the egg and then exported via the hemolymph to the oocyte (Lagueux 1981). This phenomenon also applies to other insect species, e.g. *Ixodes scapularis* (James 1997) and *Dysdercus koenigii* (Venugopal 2000).

In summary, oocytes require several years to mature prior to ovulation (Gilbert 2000). During that time biliverdin is stored in yolk platelets and must be protected from structural chemical modifications. In fact, biliverdin spends greater than 99.99% of its existence time in storage inside lipovitellin (FIG. 6). Biliverdin is a molecule of maternal extra-oocyte origin, imported and stored in the oocyte to act much later in a different organism, the embryo, immediately after fertilization to initiate morphogenesis. The finding of biliverdin bound normally by vitellogenin and lipovitellin increases the number of proteins known to associate with this tetrapyrrole. As already mentioned above, albumin is another example. In addition, the aryl hydrocarbon receptor (AhR) protein binds and is activated by biliverdin in the $\mu$M range (Phelan 1998). All of these findings are consistent with the view that biliverdin is a functional molecule.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for promoting cell differentiation, comprising treating a cell with a bilin, wherein the cell is selected from the group consisting of liposarcoma cell, thyroid carcinoma cell and lymphoblast cell.

2. A method for promoting differentiation of a cell, comprising treating the cell with a bilin represented by the general formula (I):

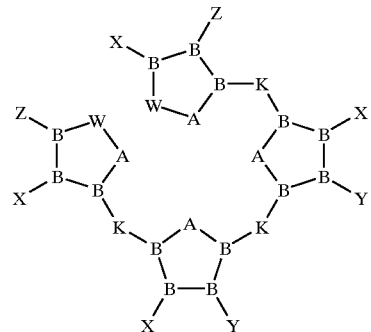

wherein
W, independently for each occurrence, represents —$CL_2$—, —C(=O)—, —C(=S)—, —C(=NH)—, or =CL—;
X, independently for each occurrence, represents a substituted or unsubstituted alkyl, alkenyl, or alkynyl group;
Y, independently for each occurrence, represents a substituted or unsubstituted alkyl, alkenyl, or alkynyl group;
Z, independently for each occurrence, represents a substituted or unsubstituted alkyl, alkenyl, or alkynyl group;
A, independently for each occurrence, represents —NH— or —N=;
B, independently for each occurrence, represents a trisubstituted, $sp^2$-hybridized carbon atom;
K, independently for each occurrence, represents =CL— or —$CL_2$—; and
L, independently for each occurrence, represents H or lower alkyl, wherein the cell is selected from the group consisting of liposarcoma cell, thyroid carcinoma cell and lymphoblast cell.

3. The method of claim 2, wherein the cell is contacted with the bilin in vitro.

4. The method of claim 2, wherein the cell is contacted with the bilin in vivo.

5. The method of claim 2, wherein at least one occurrence of Y includes a carboxyl group.

6. The method of claim 1, wherein the bilin is bilirubin or biliverdine.

7. The method of claim 2, wherein the bilin is bilirubin or biliverdine.

* * * * *